US012578321B2

(12) United States Patent
Savagian et al.

(10) Patent No.: US 12,578,321 B2
(45) Date of Patent: Mar. 17, 2026

(54) POLYPEPTIDE NANOPORES SYNTHETICALLY FUNCTIONALIZED WITH POSITIVELY CHARGED SPECIES, AND METHODS OF MAKING AND USING THE SAME

(71) Applicant: Illumina, Inc., San Diego, CA (US)

(72) Inventors: Lisa Savagian, San Diego, CA (US); Burton Simpson, San Diego, CA (US); Sang Park, San Diego, CA (US); Boyan Boyanov, San Diego, CA (US); Jeffrey G. Mandell, Rancho Santa Fe, CA (US); Seth M. McDonald, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 218 days.

(21) Appl. No.: 18/552,532

(22) PCT Filed: Mar. 10, 2022

(86) PCT No.: PCT/US2022/019802
§ 371 (c)(1),
(2) Date: Sep. 26, 2023

(87) PCT Pub. No.: WO2022/211998
PCT Pub. Date: Oct. 6, 2022

(65) Prior Publication Data
US 2024/0280557 A1 Aug. 22, 2024

Related U.S. Application Data

(63) Continuation-in-part of application No. PCT/US2022/018371, filed on Mar. 1, 2022.
(Continued)

(51) Int. Cl.
*G01N 33/487* (2006.01)
*B82B 1/00* (2006.01)
(Continued)

(52) U.S. Cl.
CPC ....... *G01N 33/48721* (2013.01); *B82B 1/008* (2013.01); *B82B 3/0038* (2013.01); *C12Q 1/6869* (2013.01)

(58) Field of Classification Search
None
See application file for complete search history.

(56) References Cited

U.S. PATENT DOCUMENTS 5,795,782 A 8/1998 Church et al.
7,939,249 B2 5/2011 Parthasarathy et al.
(Continued)

FOREIGN PATENT DOCUMENTS

WO 2005105272 A1 11/2005
WO 2012138357 A1 10/2012
(Continued)

OTHER PUBLICATIONS

Y. Astier, et al. "Toward Single Molecule DNA Sequencing: Direct Identification of Ribonucleoside and Deoxyribonucleoside 5'-Monophosphates by Using an Engineered Protein Nanopore Equipped with a Molecular Adapter", Journal of the American Chemical Society, 128: p. 1705-1710 (Year: 2006).*
(Continued)

*Primary Examiner* — J. Christopher Ball
(74) *Attorney, Agent, or Firm* — Sheppard, Mullin, Richter & Hampton LLP; Jaime D. Choi

(57) ABSTRACT

Polypeptide nanopores synthetically functionalized with positively charged species, and methods of making and using the same, are provided herein. In some examples, a polypeptide nanopore includes a first side, a second side, a channel extending through the first and second sides, and a mutated amino acid residue. The mutated amino acid residue
(Continued)

may be synthetically functionalized with a positively charged species that inhibits translocation of cations through the channel.

18 Claims, 18 Drawing Sheets

Related U.S. Application Data

(60) Provisional application No. 63/168,646, filed on Mar. 31, 2021.

(51) Int. Cl.
*B82B 3/00* (2006.01)
*C12Q 1/6869* (2018.01)

(56) References Cited

U.S. PATENT DOCUMENTS

| | | | | |
|---|---|---|---|---|
| 8,324,360 | B2 | 12/2012 | Kokoris et al. | |
| 8,349,565 | B2 | 1/2013 | Kokoris et al. | |
| 8,586,301 | B2 | 11/2013 | Kokoris et al. | |
| 8,592,182 | B2 | 11/2013 | Kokoris et al. | |
| 9,670,526 | B2 | 6/2017 | Kokoris et al. | |
| 9,708,655 | B2 | 7/2017 | Mandell et al. | |
| 9,771,614 | B2 | 9/2017 | Kokoris et al. | |
| 9,920,386 | B2 | 3/2018 | Kokoris et al. | |
| 10,301,345 | B2 | 5/2019 | Kokoris et al. | |
| 10,457,979 | B2 | 10/2019 | McRuer et al. | |
| 10,676,782 | B2 | 6/2020 | McRuer et al. | |
| 10,745,685 | B2 | 8/2020 | Kokoris et al. | |
| 10,774,105 | B2 | 9/2020 | Kokoris et al. | |
| 10,851,405 | B2 | 12/2020 | Kokoris et al. | |
| 10,866,230 | B2 | 12/2020 | Grinstaff et al. | |
| 2010/0099198 | A1 | 4/2010 | Zhao et al. | |
| 2017/0369944 | A1 | 12/2017 | Barrall et al. | |
| 2018/0364214 | A1* | 12/2018 | Maglia ................. | C07K 14/001 |
| 2020/0132664 | A1 | 4/2020 | Boyanov et al. | |
| 2021/0263011 | A1 | 8/2021 | Meller et al. | |

FOREIGN PATENT DOCUMENTS

| | | | |
|---|---|---|---|
| WO | 2013153359 | A1 | 10/2013 |
| WO | 2014022365 | A1 | 2/2014 |
| WO | 2016187519 | A1 | 11/2016 |
| WO | 2018236906 | A2 | 12/2018 |
| WO | 2019160925 | A1 | 8/2019 |
| WO | 2020068400 | A2 | 4/2020 |
| WO | 2020247472 | A1 | 12/2020 |

OTHER PUBLICATIONS

S. Borsley, et al. "In Situ Synthetic Functionalization of a Transmembrane Protein Nanopore", ACS Nano, 12: p. 786-794 (Year: 2018).*

M.M. Haugland, et al. "Synthetically Diversified Protein Nanopores: Resolving Click Reaction Mechanisms", ACS Nano, 13: p. 4104-4110 (Year: 2019).*

An et al., "Crown ether-electrolyte interactions permit nanopore detection of individual DNA abasic sites in single molecules," Proceedings of the National Academy of Sciences (PNAS) 109(29): pp. 11504-11509 (2012).

Besanceney-Webler et al., "Increasing the Efficacy of Bioorthogonal Click Reactions for Bioconjugation: A Comparative Study," Angewandte Chemie—International Edition 50(35): pp. 8051-8056 (2011).

Besanceney-Webler et al., "Increasing the Efficacy of Bioorthogonal Click Reactions for Bioconjugation: A Comparative Study," Angewandte Chemie—International Edition 50(35): pp. 8051-8056 (2011) Supplemental Information.

Butler et al., "Single-molecule DNA detection with an engineered MspA protein nanopore," Proc. Natl. Acad. Sci., 105(52): pp. 20647-20652 (2008).

Cao et al., "Discrimination of oligonucleotides of different lengths with a wild-type aerolysin nanopore," Nature Nanotechnology 11: 713-718 (2016).

Cao et al., "Discrimination of oligonucleotides of different lengths with a wild-type aerolysin nanopore," Nature Nanotechnology 11: 713-718 (2016) Supplemental Information.

Cheng et al., "Synthesis of a novel fluorescent ruthenium complex by an appended Ac4GlcNAc moiety by click reaction," Molecules, 23(7): 1649, 10 pages (2018).

Cohen et al.,"An Umpolung Approach for the Chemoselective Arylation of Selenocysteine in Unprotected Peptides," Journal of the American Chemical Society 137(31): pp. 9784-9787 (2015) DOI: 10.1021/jacs.5b05447.

Derrington et al., "Nanopore DNA sequencing with MspA," Proceedings of the National Academy of Sciences (PNAS) 107(37): pp. 16060-16065 (2010).

Griffiths et al., "Site-Selective Modification of Peptides and Proteins via Interception of Free-Radical-Mediated Dechalcogenation," Angewandte Chemie International 59(52): pp. 23659-23667 (2020).

International Search Report and Written Opinion for PCT/US2022/018371 dated May 23, 2022; 12 pages.

International Search Report and Written Opinion for PCT/US2022/019802 dated Jun. 21, 2022; 12 pages.

Jou et al., "Effects of Nanopore Charge Decorations on the Translocation Dynamics of DNA," Biophysical Journal 113(8): pp. 1664-1672 (2017) XP085222497 DOI: 10.1016/J.BPJ.2017.08.045.

Krall et al., "Site-selective protein-modification chemistry for basic biology and drug development," Nat Chem. 8(2): pp. 103-113 (2016) doi: 10.1038/nchem.2393.

Li et al., "Copper-free Sonogashira cross-coupling for functionalization of alkyne-encoded proteins in aqueous medium and in bacterial cells," J Am Chem Soc. 133(39): pp. 15316-15319 (2011) doi: 10.1021/ja2066913.

Maglia et al., "Enhanced translocation of single DNA molecules through alpha-hemolysin nanopores by manipulation of internal charge," Proceedings of the National Academy of Sciences (PNAS) 105(50): pp. 19720-19725 (2008) XP002568390 DOI: 10.1073/PNAS.0808296105.

Qi et al., "Synergic Effects of the Nanopore Size and Surface Charge on the Ion Selectivity of Graphene Membranes," J. Phys. Chem. 125(1): pp. 507-514 (2020).

Sato et al., "Site-Selective Protein Chemical Modification of Exposed Tyrosine Residues Using Tyrosine Click Reaction," Bioconjugate Chem. 31(5): pp. 1417-1424 (2020).

Sato et al., "Site-Selective Protein Chemical Modification of Exposed Tyrosine Residues Using Tyrosine Click Reaction," Bioconjugate Chem. 31(5): pp. 1417-1424 (2020) Supplemental Information.

Spicer et al., "Selective chemical protein modification," Nature Communications 5(4740): pp. 1-14 (2014) https://doi.org/10.1038/ncomms5740.

Tay et al., "Targeted Activation in Localized Protein Environments via Deep Red Photoredox Catalysis," ChemRxiv pp. 1-23 (2021) 10.33774/chemrxiv-2021-x9bjv.

Van Der Verren et al., "A dual-constriction biological nanopore resolves homonucleotide sequences with high fidelity," Nature Biotechnology 38(12): pp. 1415.1420 (2020).

Vantourout et al., "Serine-Selective Bioconjugation" Journal American Chemistry Society 142(41): pp. 17236-17242 (2020) https://doi.org/10.1021/jacs.0c05595.

Vinogradova et al., "Organometallic palladium reagents for cysteine bioconjugation," Nature 526(7575): pp. 687-691 (2015) doi: 10.1038/nature15739.

Wang et al., "Single-molecule DNA detection using a novel SP1 protein nanopore," Chem. Commun., 49: pp. 1741-1743 (2013).

Wang et al., "Single-molecule DNA detection using a novel SP1 protein nanopore," Chem. Commun., 49: pp. 1741-1743 (2013) Supplemental Information.

(56) References Cited

OTHER PUBLICATIONS

Wloka et al., "Alpha-helical Fragaceatoxin C nanopore engineered for double-stranded and single-stranded nucleic acid analysis," Angewandte Chemie Int'l Ed. 55(40): 12494-12498 (2016).

* cited by examiner

POLYPEPTIDE NANOPORES SYNTHETICALLY FUNCTIONALIZED WITH POSITIVELY CHARGED SPECIES, AND METHODS OF MAKING AND USING THE SAME

CROSS-REFERENCE TO RELATED APPLICATIONS

This application is a U.S. national phase application under 35 U.S.C. § 371 of International Patent Application No. PCT/US2022/019802 filed on Mar. 10, 2022 and entitled "Polypeptide Nanopores Synthetically Functionalized with Positively Charged Species, and Methods of Making and Using the Same," the entire contents of which are incorporated by reference herein, and which claims the benefit of the following applications, the entire contents of each of which are incorporated by reference herein:

International Patent Application No. PCT/US2022/018371, filed Mar. 1, 2022 and entitled "Nanopore Sensor Devices," and U.S. Provisional Patent Application No. 63/168,646, filed Mar. 31, 2021 and entitled "Nanopore Sensor Devices."

FIELD

This application relates to polypeptide nanopores, and sensors using polypeptide nanopores.

BACKGROUND

Various polynucleotide sequencing techniques involve performing a large number of controlled reactions on local support surfaces or within predefined reaction chambers. The designated reactions may then be observed or detected, and subsequent analysis may help identify or reveal properties of the polynucleotide involved in the reaction. Another polynucleotide sequencing technique has been developed that utilizes a nanopore, which can provide a channel for an ionic electrical current. A polynucleotide or label/tag of an incorporated nucleotide is driven into the nanopore, changing the resistivity of the nanopore. Each nucleotide (or series of nucleotides) or each label/tag (or series of labels/tags) yields a characteristic electrical signal, and the record of the signal levels corresponds to the sequence of the polynucleotide. In prior nanopore sensor devices (at t=0), the current is equally carried by the electrolyte translocating through the nanopore in opposite directions between a cis well and a trans well. However, such nanopore sequencing devices may suffer from lifetimes that are insufficient for commercial use.

SUMMARY

Polypeptide nanopores synthetically functionalized with positively charged species, and methods of making and using the same, are provided herein.

Some examples herein provide polypeptide nanopore including a first side, a second side, a channel extending through the first and second sides, and a mutated amino acid residue which is synthetically functionalized with a positively charged species that inhibits translocation of cations through the channel.

In some examples, the positively charged species is coupled to an interior surface of the nanopore.

In some examples, the mutated amino acid residue includes a natural amino acid residue or an unnatural amino acid residue.

In some examples, the natural amino acid residue includes cysteine, serine, tyrosine, lysine, phenylalanine, tryptophan, methionine, or selenocysteine.

In some examples, the unnatural amino acid residue includes an alkyne, azide, or alkene.

In some examples, the polypeptide nanopore includes MspA, Fragaceatoxin C, α-hemolysin, aerolysin, CsgG, or CsgG/CsgF. In some examples, the polypeptide nanopore includes MspA, and the mutated amino acid residue is located at residue 90, 91, or 93.

In some examples, the positively charged species includes a nonmetal cation. In some examples, the nonmetal cation includes $NR_4^+$, where each R group independently includes hydrogen, a saturated alkyl group, an unsaturated alkyl group, an aromatic species, oxygen, nitrogen, silicon, sulfur, boron, phosphorous, a thiol, an ester derivation, an amide derivation, an amine derivation, a carbonyl derivation, a heterocycle, oligo(siloxane), oligo(ethylene oxide), an amino acid, a nucleobase, a reactive handle for further bioconjugation, a photoactive label, a photoactive dye, a redox-active label, or a redox-active dye, and at least one of the R groups is covalently linked to the mutated amino acid residue through at least one bond. In some examples, the nonmetal cation includes $C_5H_4R(NR)^+$, $C_3H_2R(NH)(NR)^+$, $C_8H_7R(NR_2)^+$, $C(NR_2)_3^+$, $SR_3^+$, $PR_4^+$, $BR_2^+$, $C_3R_3^+$ (cyclopropenium), $C_3R_3(NR)S^+$ (thiozonium), or $C_3R_3(NR)O^+$ (oxazonium), and where each R group independently includes hydrogen, a saturated alkyl group, an unsaturated alkyl group, an aromatic species, oxygen, nitrogen, silicon, sulfur, boron, phosphorous, a thiol, an ester derivation, an amide derivation, an amine derivation, a carbonyl derivation, a heterocycle, oligo(siloxane), oligo(ethylene oxide), an amino acid, a nucleobase, a reactive handle for further bioconjugation, a photoactive label, a photoactive dye, a redox-active label, a redox-active dye, a nitrogenous aromatic and pi-conjugated species, a pyridinium, an imidazolium, an indolium, a guanidinium, a carbazolium, a quinolinium, a functionalized derivative of a pyridinium, or a functionalized derivative of a purinium, and at least one of the R groups is covalently linked to the mutated amino acid residue through at least one bond.

In some examples, the positively charged species includes a cationic metal coordination complex. In some examples, the cationic metal coordination complex includes at least one metal ion complexed to one or more nonmetal ligands. In some examples, the at least one metal ion includes a transition metal cation. In some examples, the transition metal ion includes a nickel cation, a manganese cation, an iron cation, a cobalt cation, or a copper cation. In some examples, the at least one metal ion includes a noble metal cation. In some examples, the noble metal cation includes a ruthenium cation, a palladium cation, an osmium cation, an iridium cation, or a platinum cation.

In some examples, the one or more nonmetal ligands include carbon, nitrogen, sulfur, oxygen, hydrogen, or a halide. In some examples, the at least one of the one or more nonmetal ligands is covalently bound to the mutated amino acid residue.

In some examples, the positively charged species includes an ionophore. In some examples, the ionophore includes a (macro)cyclic polyamine or a (macro)cyclic polyether. In some examples, the ionophore includes a crown ether, a cryptand or a calixarene. In some examples, the crown ether includes 18-crown-6. In some examples, the ionophore includes valinomycin, nystatin A, or monensin A. In some examples, the ionophore is covalently bound to the mutated amino acid residue.

In some examples, the polypeptide nanopore includes multiple polypeptide subunits. In some examples, at least one of the multiple polypeptide subunits does not include the mutated amino acid residue. In some examples, at least two of the polypeptide subunits are cross-linked to one another. In some examples, the at least two of the polypeptide subunits are crosslinked through the positively charged species. In some examples, each of the polypeptide subunits is coupled to a respective positively charged species.

In some examples, the positively charged species has a net charge of +1. In some examples, the positively charged species has a net charge of +2.

Some examples include a plurality of the positively charged species. Some examples have an overall net charge of greater than +2. Some examples have an overall net charge of between about +2 and +18.

Some examples herein provide method of making a nanopore. The method may include providing a polypeptide nanopore including a first side, a second side, a channel extending through the first and second sides, and a mutated amino acid residue. The method may include synthetically functionalizing the mutated amino acid residue with a positively charged species.

In some examples, providing the polypeptide nanopore includes providing a plurality of polypeptide nanopore subunits, at least one of which includes the mutated amino acid residue. In some examples, providing the polypeptide nanopore further includes assembling the plurality of polypeptide nanopore subunits into a nanopore.

In some examples, the mutated amino acid residue includes a thiol group.

In some examples, the positively charged species includes a product of a Michael addition, a radical thiol-ene "click" reaction, aminoethylation, disulfide bond formation, a reaction including iodoacetamides, a reaction including maleimides, a reaction including glutathione, a reaction yielding docosahexaenoic acid as a byproduct, a reaction including the desulfurization of disulfides, a reaction including oxidation, a reaction including metal-mediated cross-coupling, a reaction including radical-mediated dehalogenation.

In some examples, the synthetic functionalization includes a reaction with an oxidizing or reducing agent, treatment with an acid or base, nucleophilic addition, metal-mediated cross-coupling, photocatalyzed homolysis, photocatalyzed heterolysis, redox-catalyzed homolysis, redox-catalyzed heterolysis, metathesis, etherification, esterification, amination, amidation, aromatic substitution, dehydroalanination, ligation, cycloaddition, condensation, or a light-mediated reaction.

In some examples, the reactive amino acid residue includes an unnatural amino acid residue. In some examples, the unnatural amino acid residue includes an azide group. In some examples, the unnatural amino acid residue includes azidohomoalanine. In some examples, the synthetic functionalization includes a product of Cu(I)-catalyzed click chemistry.

In some examples, the unnatural amino acid residue includes an alkyne. In some examples, the unnatural amino acid residue includes hydroxyphenylglycine or homopropargylglycine. In some examples, the synthetic functionalization includes a product of Cu(I)-catalyzed click chemistry or Sonogashira coupling.

In some examples, the unnatural amino acid residue includes an alkene. In some examples, the unnatural amino acid residue includes homoallylglycine. In some examples, the synthetic functionalization includes a product of chemical oxidation or Heck-type coupling.

Some examples herein provide a method of using a nanopore. The method may include providing a polypeptide nanopore including a first side, a second side, a channel extending through the first and second sides, and a mutated amino acid residue which is synthetically functionalized with a positively charged species. The method may include inhibiting, using the positively charged species, translocation of cations through the channel. The method may include translocating anions through the channel.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1:
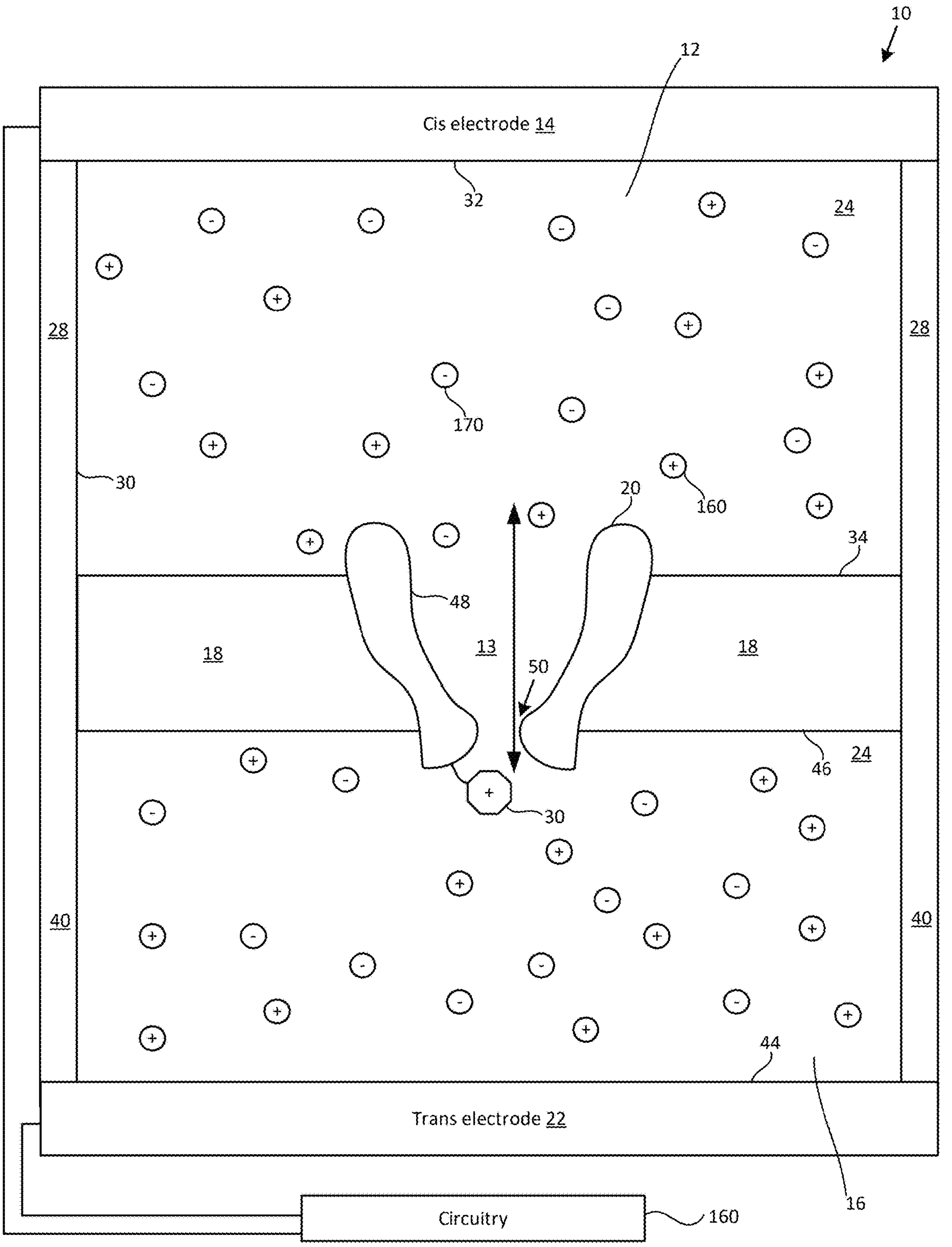
FIG. 1 schematically illustrates a cross-sectional view of an example composition and nanopore sensor device including a polypeptide nanopore synthetically functionalized with a positively charged species.

Polypeptide nanopores synthetically functionalized with positively charged species, and methods of making and using the same, are provided herein.

The technique of nanopore sequencing uses variations in electrical signal to distinguish nucleotide bases. Nanopore sensor devices include a cis well, a cis electrode, a trans well, and a trans electrode. The trans well is separated from the cis well by a barrier having a nanopore therein. Faradaic current between the cis electrode and trans electrode is established by redox species with or without an electrolyte buffer.

In nanopore-based sequencing platforms, the volume of the wells in the device is reduced so as to enhance data output and efficiency. However, shrinking the trans well volume may result in accelerated electrolyte depletion. During this process, the current signal may gradually decay to a level that is too low for sequencing. The origin of this electrolyte depletion may stem from an imbalance in the consumption and supply of the redox-active species in the trans well.

In certain examples, the electrodes are chemically active (i.e., the electrodes actively participate in the redox reaction), and the reactive electrolyte species (i.e., redox anions) are consumed by being plated out at the trans electrode in a positive polarity to support Faradaic current through the system. In certain examples, the electrodes are passive (i.e., the electrodes do not actively participate in the redox reaction), and the reactive electrolyte species (i.e., redox couple ions) are consumed by being oxidized at the trans electrode in a positive polarity to support Faradaic current through the system. In these examples, the redox couple is suspended or dissolved in a redox-inactive electrolyte buffer. The trans electrode is located in a confined compartment with a limited volume and thus, in these instances, the replenishment of the reactive electrolyte species in the trans well is dependent upon the transport of the species through the nanopore from the cis well. In prior nanopore sensor devices, the concentration of reactive electrolyte within the trans well may become partially depleted, which reduces the operability of the nanopore sensor device.

In an example of an Ag/Cl redox system with active electrodes, chloride anions may be partially depleted on the trans side due to plating out onto the trans electrode and may not be fully replaced by transport of chloride anions through the nanopore. For example, when two chloride ions are consumed by plating out at the trans electrode, one chloride ion transits through the nanopore into the trans well. If the concentration of chloride ions is low in the trans well, there is reduced reactive electrolyte species in the trans well. This reduces the ability to carry ionic current, and thus results in reduced signal level and detection by the nanopore sensor device.

In anion-mediated redox systems such as Ag/AgCl, where the $Cl^-$ anion is the redox-active charge carrying species, the translocation of the electrolyte cation (e.g., $K^+$) through the nanopore contributes to charge imbalance and resulting depletion. The present inventors have recognized that suppressing the translocation of cations through the nanopore may reduce or inhibit electrolyte depletion, thus enhancing signal stability and allowing the size of the nanopore sensor device to be further reduced.

Because the reactive electrolyte species is replenished at a fraction of how much is plated out in prior nanopore sensor devices, depletion or partial consumption of the electrochemically active electrolyte species in the trans well occurs over time. The partial consumption of the reactive electrolyte species depends on several factors, including the current that passes through the nanopore, and the size of the trans well (e.g., larger wells are generally associated with less reagent consumption and smaller chambers are generally associated with more reagent consumption). The time to complete depletion of the reactive electrolyte species in the trans well of prior nanopore sensor devices can be estimated from equation 1:

$$t_{max} \sim 2\frac{VCN_A}{1000}\frac{q}{i} \qquad \text{(equation 1)}$$

where V (e.g., in units of $cm^3$) is the trans well volume, C (e.g., in units of mol/L) is the reactive electrolyte species concentration at t=0 in the trans well, NA is Avogadro's number, q (e.g., in units of Coulomb or C) is the elementary charge of the reactive electrolyte species, and i (e.g., in units of A) is the nanopore current.

In prior nanopore sensor devices, partial consumption may be evidenced by a reduction in the initial reagent concentration, where the reduction is greater than a factor of 10. In some instances, the reduction ranges from a factor of 20 to a factor of 100. For example, the chloride concentration of an electrolyte solution having an initial chloride concentration of about 300 mM in a 10 μm trans well can be depleted to about 10 mM, and thus the initial concentration is reduced by a factor of about 30. For another example, the chloride concentration of an electrolyte solution having an initial chloride concentration of about 10 mM in a 10 μm trans well can be depleted to about 0.1 mM, and thus the initial concentration is reduced by a factor of about 100. It is to be understood that the partial consumption/depletion can approach 100% (i.e., the partially consumed electrolyte species remaining in the system approaches 0%), but an equilibrium will establish between the electrolyte anions and cations, even at such low levels of the partially consumed species.

In an example of an ferrocyanide/ferricyanide redox couple in an electrolyte buffer with passive electrodes, ferrocyanide ions (e.g., $Fe(CN)_6^{4-}$) are oxidized to ferricyanide ions (e.g., $Fe(CN)_6^{3-}$) at the trans electrode in a forward polarity. Because the redox couples are both negatively charged, counterions may be included to maintain the overall electrical neutrality of the solution. Examples of suitable counterions include sodium, lithium, calcium, and potassium. The reactive electrolyte species may be partially depleted on the trans side due to being consumed at the trans electrode and may not be fully replaced by transport of reactive electrolyte species through the nanopore.

Certain examples of the nanopore sensor device and method disclosed herein reduce the depletion of the reactive electrolyte species at the trans well(s) of the nanopore sensor device. In these examples, a reduction in the initial reactive electrolyte species concentration at the trans well(s) may still occur; however, the reduction is less than 10% and likely less than 1%. As such, more of the reactive electrolyte species is present over time (e.g., compared to the prior nanopore sensor devices provided above), and thus depletion of the reactive electrolyte species is reduced. In certain examples, depletion of the reactive electrolyte species is reduced by inhibiting the transport of cations through the nanopore(s) of the nanopore sensor device. In these certain examples, the reduction of the transport of the nonreactive cations is accomplished using unbalanced electrolyte concentrations, modified nanopores, and/or charge induced in the nanopores, for example nanopores that are mutated and functionalized with positively charged species. In these certain examples, the reduction of the transport of nonreactive cations may be accomplished using unbalanced electrolyte concentrations and/or utilizing a bulky buffer cation. Reducing the transport of the nonreactive ion (e.g. buffer cations) through the nanopore results in a higher amount of the ionic charge to be carried by the reactive electrolyte species. Thus, an increased amount of reactive electrolyte species is transported into the trans well from the cis well. As a result, reactive electrolyte species depletion from trans well(s) of the nanopore sensor device is reduced and the lifetime of the nanopore sensor device is extended.

As mentioned above, the technique of nanopore sequencing uses variations in electrical signal to distinguish nucleotide bases. A depletion in the reactive electrolyte species in the trans wells reduces ionic current and lowers the signal detected by the nanopore sensor device. By increasing the replenishment of reactive electrolyte species from the cis well into the trans well, the lifetime of the nanopore sensor device may be increased.

Definitions

It is to be understood that terms used herein will take on their ordinary meaning in the relevant art unless specified otherwise. Several terms used herein and their meanings are set forth below.

The singular forms “a”, “an”, and “the” include plural referents unless the context clearly dictates otherwise.

The terms comprising, including, containing and various forms of these terms are synonymous with each other and are meant to be equally broad.

The terms top, bottom, lower, upper, on, etc. are used herein to describe the nanopore sensor device and/or the various components of the nanopore sensor device. It is to be understood that these directional terms are not meant to imply a specific orientation, but are used to designate relative orientation between components. The use of directional terms should not be interpreted to limit the examples disclosed herein to any specific orientation(s).

The terms first, second, etc. also are not meant to imply a specific orientation or order, but rather are used to distinguish one component from another.

It is to be understood that the ranges provided herein include the stated range and any value or sub-range within the stated range, as if such values or sub-ranges were explicitly recited. For example, a range from about 50 mM to about 500 mM should be interpreted to include not only the explicitly recited limits of from about 50 mM to about 500 mM, but also to include individual values, such as about 100 mM, about 335 mM, about 400.5 mM, about 490 mM, etc., and sub-ranges, such as from about 75 mM to about 475 mM, from about 200 mM to about 300 mM, etc. Furthermore, when “about” and/or “substantially” are/is utilized to describe a value, this is meant to encompass minor variations (up to +/−10%) from the stated value.

As used herein, the terms “fluidically connecting,” “fluid communication,” “fluidically coupled,” and the like refer to two spatial regions being connected together such that a liquid or gas may flow between the two spatial regions. For example, a cis well may be fluidically connected to a trans well or a plurality of trans wells, such that at least a portion of an electrolyte solution may transit between the connected wells. The two spatial regions may be in fluid communication through a nanopore, or through one or more valves, restrictors, or other fluidic components that are to control or regulate a transit of ions through a system.

As used herein, the term “membrane” refers to a non-permeable or semi-permeable barrier or other sheet that separates two liquid/gel chambers (e.g., a cis well and a trans well) which can contain the same compositions or different compositions therein. The permeability of the membrane to any given species depends upon the nature of the membrane. In some examples, the membrane may be non-permeable to ions, to electric current, and/or to fluids. For example, a lipid membrane may be impermeable to ions (i.e., does not allow any ion transport therethrough), but may be at least partially permeable to water (e.g., water diffusivity ranges from about 40 μm/s to about 100 μm/s). For another example, a synthetic/solid state membrane, such as silicon nitride, may be impermeable to ions, electric charge, and fluids (i.e., the diffusion of all of these species is zero). Any membrane may be used in accordance with the present disclosure, so long as the membrane can include a transmembrane nanoscale opening (e.g., a nanopore) and can maintain a potential difference across the membrane. The membrane may be a monolayer or a multilayer membrane. A multilayer membrane includes two or more layers, each of which is a non-permeable or semi-permeable material.

The membrane may be formed of materials of biological or non-biological origin. A material that is of biological origin refers to material derived from or isolated from a biological environment such as an organism or cell, or a synthetically manufactured version of a biologically available structure (e.g., a biomimetic material).

An example membrane that is made from the material of biological origin includes a monolayer formed by a bolalipid. Another example membrane that is made from the material of biological origin includes a lipid bilayer. Suitable lipid bilayers include, for example, a membrane of a cell, a membrane of an organelle, a liposome, a planar lipid bilayer, and a supported lipid bilayer. A lipid bilayer can be formed, for example, from two opposing layers of phospholipids, which are arranged such that their hydrophobic tail groups face towards each other to form a hydrophobic interior, whereas the hydrophilic head groups of the lipids face outwards towards the aqueous environment on each side of the bilayer. Lipid bilayers also can be formed, for example, by a method in which a lipid monolayer is carried on an aqueous solution/air interface past either side of an aperture which is perpendicular to that interface. The lipid is normally added to the surface of an aqueous electrolyte solution by first dissolving it in an organic solvent and then allowing a drop of the solvent to evaporate on the surface of the aqueous solution on either side of the aperture. Once the organic solvent has at least partially evaporated, the solution/air interfaces on either side of the aperture are physically moved up and down past the aperture until a bilayer is formed. Other suitable methods of bilayer formation include tip-dipping, painting bilayers, and patch-clamping of liposome bilayers. Any other methods for obtaining or generating lipid bilayers may also be used.

A material that is not of biological origin may also be used as the membrane. Some of these materials are solid state materials and can form a solid state membrane, and others of these materials can form a thin liquid film or membrane. The solid state membrane can be a monolayer, such as a coating or film on a supporting substrate (i.e., a solid support), or can be a free-standing element. The solid state membrane can also be a composite of multilayered materials in a sandwich configuration. Any material not of biological origin may be used, as long as the resulting membrane can include a transmembrane nanoscale opening and can maintain a potential difference across the membrane. The membranes may include organic materials, inorganic materials, or both. Examples of suitable solid state materials include, for example, microelectronic materials, insulating materials (e.g., silicon nitride ($Si_3N_4$), aluminum oxide ($Al_2O_3$), hafnium oxide ($HfO_2$), tantalum pentoxide ($Ta_2O_5$), silicon oxide ($SiO_2$), etc.), some organic and inorganic polymers (e.g., polyamide, plastics, such as polytetrafluoroethylene (PTFE), or elastomers, such as two-component addition-cure silicone rubber), and glasses. In addition, the solid state membrane can be made from a monolayer of graphene, which is an atomically thin sheet of carbon atoms densely packed into a two-dimensional honeycomb lattice, a multilayer of graphene, or one or more layers of graphene mixed with one or more layers of other solid state materials. A graphene-containing solid state membrane can include at least one graphene layer that is a graphene nanoribbon or graphene nanogap, which can be used as an electrical sensor to characterize the target polynucleotide. The solid state membrane can be made by any suitable method. As examples, the graphene membrane can be prepared through either chemical vapor deposition (CVD) or exfoliation from graphite. Examples of suitable thin liquid film materials that may be used include diblock copolymers, triblock copolymers, such as amphiphilic PMOXA-PDMS-PMOXA ABA triblock copolymers.

As used herein, the term "nanopore" is intended to mean a hollow structure discrete from and extending across the membrane that permits ions, electric current, and/or fluids to cross from one side of the membrane to the other side of the membrane. For example, a membrane that inhibits the passage of ions or water soluble molecules can include a nanopore structure that extends across the membrane to permit the passage (through a nanoscale opening/channel extending through the nanopore structure) of the ions or water soluble molecules from one side of the membrane to the other side of the membrane. The diameter of the nanoscale opening/channel can vary along its length (i.e., from one side of the membrane to the other side of the membrane), but at any point is on the nanoscale (i.e., from about 1 nm to about 100 nm, or to less than 1000 nm). Examples of the nanopore include, for example, biological nanopores, and biological and solid state hybrid nanopores.

As used herein, the term "diameter" is intended to mean a longest straight line inscribable in a cross-section of a nanoscale opening through a centroid of the cross-section of the nanoscale opening. It is to be understood that the nanoscale opening may or may not have a circular or substantially circular cross-section (the cross-section of the nanoscale opening being substantially parallel with the cis/trans electrodes). Further, the cross-section may be regularly or irregularly shaped.

As used herein, the term "biological nanopore" is intended to mean a nanopore whose structure portion is made from materials of biological origin. Biological origin refers to a material derived from or isolated from a biological environment such as an organism or cell, or a synthetically manufactured version of a biologically available structure. Biological nanopores include, for example, polypeptide nanopores and polynucleotide nanopores.

As used herein, the terms "polypeptide nanopore" and "protein nanopore" are intended to mean a polypeptide that permits ions and/or fluids to flow therethrough. For example, when a polypeptide nanopore extends across a membrane, ions and/or fluids may flow from one side of the membrane to the other side of the membrane. A polypeptide nanopore can be a monomer, a homopolymer, or a heteropolymer. Structures of polypeptide nanopores include, for example, an α-helix bundle nanopore and a β-barrel nanopore. Example polypeptide nanopores include α-hemolysin (aHL). *Mycobacterium smegmatis* porin A (MspA), gramicidin A, maltoporin, OmpF, OmpC, PhoE, Tsx, F-pilus, CsgG, CsgG/CsgF, Fragaceatoxin C, Aerolysin, and the like. The protein α-hemolysin is found naturally in cell membranes, where it acts as a channel for ions or molecules to be transported in and out of cells. *Mycobacterium smegmatis* porin A (MspA) is a membrane porin produced by Mycobacteria, which allows hydrophilic molecules to enter the bacterium. MspA forms a tightly interconnected octamer and transmembrane beta-barrel that resembles a goblet and contains a central channel/pore.

For further details regarding α-hemolysin, see U.S. Pat. No. 6,015,714, the entire contents of which are incorporated by reference herein. For further details regarding SP1, see Wang et al., Chem. Commun., 49:1741-1743 (2013), the entire contents of which are incorporated by reference herein. For further details regarding MspA, see Butler et al., "Single-molecule DNA detection with an engineered MspA protein nanopore," Proc. Natl. Acad. Sci. 105: 20647-20652 (2008) and Derrington et al., "Nanopore DNA sequencing with MspA," Proc. Natl. Acad. Sci. USA, 107:16060-16065 (2010), the entire contents of both of which are incorporated by reference herein. Other nanopores include, for example, the MspA homolog from *Nocardia farcinica*, and lysenin. For further details regarding lysenin, see PCT Publication No. WO 2013/153359, the entire contents of which are incorporated by reference herein. For further details regarding CsgG and CsgG/CsgF, see Van der Verren et al., "A dual-constriction biological nanopore resolves homonucleotide sequences with high fidelity," Nature Biotechnology 38: 1415-1420 (2020), the entire contents of which are incorporated by reference herein. For further details regarding Fragaceatoxin C (FraC), see Wloka et al., "Alpha-helical Fragaceatoxin C nanopore engineered for double-stranded and single-stranded nucleic acid analysis," Angewandte Chemie Int'l Ed. 55(40): 12494-12498 (2016), the entire contents of which are incorporated by reference herein. For further details regarding aerolysin, see Cao et al., "Discrimination of oligonucleotides of different lengths with a wild-type aerolysin nanopore," Nature Nanotechnology 11: 713-718 (2016), the entire contents of which are incorporated by reference herein.

A polypeptide nanopore can be synthetic. A synthetic polypeptide nanopore includes a protein-like amino acid sequence that does not occur in nature. The protein-like amino acid sequence may include some of the amino acids that are known to exist but do not form the basis of proteins (i.e., non-proteinogenic amino acids). The protein-like amino acid sequence may be artificially synthesized rather than expressed in an organism and then purified/isolated.

As used herein, the term "polynucleotide nanopore" is intended to include a polynucleotide that extends across the membrane, and permits ions and/or fluids to flow from one side of the membrane to the other side of the membrane. A polynucleotide nanopore can include, for example, a polynucleotide origami (e.g., nanoscale folding of DNA to create the nanopore).

Also as used herein, the term "solid state" is intended to mean including materials of non-biological origin (i.e., not of biological origin).

The nanopores disclosed herein may be hybrid nanopores. A "hybrid nanopore" refers to a nanopore including materials of both biological and non-biological origins. An example of a hybrid nanopore includes a polypeptide-solid state hybrid nanopore and a polynucleotide-solid state nanopore.

As used herein, the term "nanopore sensor device" or "nanopore sequencer" refers to a device that uses a nanopore to sequence a polynucleotide. In the examples disclosed herein, during nanopore sequencing, the nanopore is provided within a membrane between two liquids, and a potential difference is applied across the membrane. In an example, the potential difference is an electric potential difference or an electrochemical potential difference. An electrical potential difference can be imposed across the membrane via a voltage source that injects or administers current to at least one of the ions of the electrolyte contained in the cis well or trans well. An electrochemical potential difference can be established by a difference in ionic composition of the cis and trans wells in combination with an electrical potential. The different ionic composition can be, for example, different ions in each of the cis and trans wells or different concentrations of the same ions in each of the cis and trans wells.

The application of the potential difference across the nanopore may cause the movement of one or more elements, such as one or more nucleotides, reporter regions, or labels relative to the nanopore. One or more signals are generated that correspond to the position(s) of the element(s) relative the nanopore, and that correspond to the identity of a nucleotide in a polynucleotide that is being sequenced. For example, as ions translocate through the nanopore, the current across the membrane may change due to base-dependent blockage of the constriction. The signal from that change in current can be measured using any of a variety of methods. Each signal is unique to the species of nucleotide(s) in a sequence, such that the resultant signal can be used to determine a characteristic of the polynucleotide. For example, the identity of one or more species of nucleotide(s) that produces a characteristic signal can be determined.

As used herein, a "nucleotide" includes a nitrogen containing heterocyclic base, a sugar, and one or more phosphate groups. Nucleotides are monomeric units of a nucleic acid sequence. Examples of nucleotides include, for example, ribonucleotides or deoxyribonucleotides. In ribonucleotides (RNA), the sugar is a ribose, and in deoxyribonucleotides (DNA), the sugar is a deoxyribose, i.e., a sugar lacking a hydroxyl group that is present at the 2' position in ribose. The nitrogen containing heterocyclic base can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. The phosphate groups may be in the mono-, di-, or tri-phosphate form. These nucleotides are natural nucleotides, but it is to be further understood that non-natural nucleotides, modified nucleotides or analogs of the aforementioned nucleotides can also be used.

As used herein, the term "signal" is intended to mean an indicator that represents information. Signals include, for example, an electrical signal and an optical signal. The term "electrical signal" refers to an indicator of an electrical quality that represents information. The indicator can be, for example, current, voltage, tunneling, resistance, potential, conductance, capacitance, frequency, or other changes in an electrical waveform.

The term "substrate" refers to a rigid, solid support that is insoluble in aqueous liquid and is incapable of passing a liquid absent an aperture, port, or other like liquid conduit. In the examples disclosed herein, the substrate may have wells or chambers defined therein. Examples of suitable substrates include glass and modified or functionalized glass, plastics (including acrylics, polystyrene and copolymers of styrene and other materials, polypropylene, polyethylene, polybutylene, polyurethanes, polytetrafluoroethylene (PTFE) (such as TEFLON® from Chemours), cyclic olefins/cyclo-olefin polymers (COP) (such as ZEONOR® from Zeon), polyimides, etc.), nylon, ceramics, silica or silica-based materials, silicon and modified silicon, carbon, metals, inorganic glasses, and optical fiber bundles.

A "stimulus source" refers to an electronic device that is to provide a stimulus that causes ionic current to flow through the nanopore. In one example, the stimulus source may be a current source or a voltage source coupled to the cis electrode and/or trans electrode. In another example, the stimulus source may be any source creating an electric field between the cis well and the trans well.

As used herein, the terms "well", "cavity" and "chamber" are used synonymously, and refer to a discrete feature defined in the device that can contain a fluid (e.g., liquid, gel, gas). A "cis well" is a common chamber that contains or is partially defined by a cis electrode, and is also fluidically connected to a trans well through a respective nanopore. Examples of an array of the present device may have one cis well or multiple cis wells, and may have one trans well or multiple trans wells. A "trans well" is a single chamber that contains or is partially defined by its own trans electrode, and is also fluidically connected to at least one cis well. Each trans well may be electrically isolated from any other trans wells. In some examples, each trans well is connected to a respective stimulus source, and to a respective amplifier (e.g., Axopatch 200B amplifiers) to amplify electrical signals passing through respective nanopores associated with each of the trans wells. In other examples, trans wells are connected to a single stimulus source which individually addresses the trans wells via multiplexing. Further, it is to be understood that the cross-section of a well taken parallel to a surface of a substrate at least partially defining the well can be curved, square, polygonal, hyperbolic, conical, angular, etc.

As used herein, the term "ionophore" is meant to refer to an entity that reversibly binds an ion, such as a cation or an anion, via covalent or noncovalent interactions. In examples such as described herein, ionophores that reversibly bind cations may be used to inhibit the translocation of other cations through a channel of a nanopore, while permitting the translocation of anions through the channel of the nanopore.

The aspects and examples set forth herein and recited in the claims can be understood in view of the above definitions.

Nanopore Sensor Device

Referring now to FIG. 1, an example of a nanopore sensor device 10 is depicted. The nanopore sensor device 10 includes a cis well 12, a cis electrode 14, a trans well 16, barrier 18 (such as a lipid membrane, polymer membrane, or solid-state membrane) having a nanopore 20 therein and separating trans well 16 separated from cis well 12, and trans electrode 22. The example nanopore sensor device 10 also includes an electrolyte solution 24 in the cis and trans wells 12, 16. The membrane 18 may supported by a substrate (not specifically illustrated) that partially extends between the cis well 12 and the trans well(s) 16, and the nanopore(s) 20 may be positioned in, and extend through the membrane 18 to establish the fluidic connection between the cis well 12 and the trans well(s) 16.

In a manner such as will be described in greater detail below, nanopore 20 may be a polypeptide nanopore that includes a mutated amino acid residue which is synthetically functionalized with positively charged species 30. For example, trans well 16 is fluidically connected to cis well 12 by nanopore 20, such that fluid 24 may flow from the trans well to the cis well, or from the cis well to the trans well, via opening/channel 13 of the nanopore. Illustratively, nanopore 20 may have a first side located on the cis side 12 of device 10, and a second side located on the trans side 16 of device 10, and channel 13 may extend through the first and second sides. The fluid communication through the channel 13 of nanopore 20 is indicated by the arrow in FIG. 1.

Although fluid 24 may flow through channel 13, positively charged species 30 coupled to nanopore 20 may inhibit translocation of one or more cations through channel 13 while permitting anions to translocate through the channel. For example, fluid 24 may include any suitable electrolyte(s) (salt(s)), e.g., ranging from common salts to ionic crystals, metal complexes, ionic liquids, or even water-soluble organic ions. For example, the salt may include any suitable combination of cations 160 (such as, but not limited to, $H^+$, $H_3O^+$, $Li^+$, $Na^+$, $K^+$, $NH_4^+$, $Ag^+$, $Ca^{2+}$, $Ba^{2+}$, $Cs^+$, $Mg^{2+}$, $Mn^{2+}$, $Sr^{2+}$, $BF^{4+}$, phosphonium, ammonium, diazonium, formamidium, and/or polyanions) with any suitable combination of anions 170 (such as, but not limited to, $OH^-$, $Cl^-$, $Br^-$, $I^-$, $NO_3^-$, $ClO_4^-$, F, $SO_4^{2-}$, and/or $CO_3^{2-}$). In some examples, positively charged species 30 may inhibit translocation of any such cations 160 through channel 13, while permitting any of such anions to translocate through the channel. It will also be appreciated that fluid 24 optionally may include any suitable combination of other solutes. Illustratively, fluid 24 may include an aqueous buffer (such as N-(2-hydroxyethyl)piperazine-N'-2-ethanesulfonic acid (HEPES), commercially available from Fisher BioReagents). In one nonlimiting example, the salt includes potassium chloride (KCl), e.g., potassium cations 160 which the positively charged species 30 inhibits from translocating through the channel, and chloride anions 170 which are not inhibited from translocating through the channel.

Further details regarding positively charged species 30 and the manner in which it may be coupled to nanopore 20 are provided further below with reference to FIGS. 3A-3C, 4A-4B, 5A-5C, 6A-6C, 7A-7C, 8A-8C, 9A-9C, 10, and 11. Nonlimiting examples of the manner in which nanopore 20 and positively charged species may be used are provided further below with reference to FIGS. 12-16.

Referring again to FIG. 1, the cis well 12 is a fluid chamber that is at least partially defined by sidewall(s) 28 which may be connected to a substrate (not specifically illustrated). In some examples, the sidewall(s) 28 and the substrate may be integrally formed such that they are formed from a continuous piece of material (e.g., glass or plastic). In other examples, the sidewall(s) 28 and the substrate may be separate components that are coupled to each other. In an example, the sidewall(s) 28 are photo patternable polymers.

In the example shown in FIG. 1, the cis well 12 has interior walls 30 that are defined by the sidewall(s) 28, an upper surface 32 that is defined by the cis electrode 14, and a lower surface 34 that is defined by the membrane 18. Thus, the cis well 12 is formed within the space defined by the cis electrode 14, the sidewalls 28, and the membrane 18. It is to be understood that the lower surface 34 has opening/channel 13 through the nanopore(s) 20 that are positioned in the membrane 18. The cis well 12 may have any suitable dimensions. In an example, the cis well 12 ranges from about 1 mm×1 mm to about 5 mm×5 mm. The cis electrode 14, whose interior surface is the upper surface 32 of the cis well 12, may be physically connected to the sidewall(s) 28. The cis electrode 14 may be physically connected to the sidewall(s) 28, for example, by an adhesive or another suitable fastening mechanism. The interface between the cis electrode 14 and the sidewall(s) 28 may seal the upper portion of the cis well 12.

The cis electrode 14 that is used depends, at least in part, upon the electrolyte species in the electrolyte solution 24. In some examples, the cis electrode 14 may be an active electrode that takes part in the chemical reaction with an electrochemically active electrolyte species, and can be oxidized or reduced in the half-cell reaction. Examples of active electrodes include silver (Ag), copper (Cu), zinc (Zn), lead (Pb), etc. In other examples, the cis electrode 14 may be an inactive (or inert) electrode that transfers electrons rather than exchange ions with the electrolyte solution 24. Examples of inactive electrodes include platinum (Pt), carbon (C) (e.g., graphite, diamond, etc.), gold (Au), rhodium (Rh), etc. In an example in the nanopore sensor 10 utilizing an electrolyte solution 24 with an electrically active anion (e.g., chloride, $Cl^-$), the cis electrode 14 may be a silver/silver chloride (Ag/AgCl) electrode.

As illustrated in FIG. 1, the nanopore sensor device 10 includes trans well 16. Trans well 16 is a fluid chamber that may be defined in a portion of a substrate (not specifically illustrated). In the example shown in FIG. 1, trans well 16 has sidewalls 40 that may be contiguous with sidewalls 28 of cis well 12 and/or may be defined by the substrate, a lower surface 44 that is defined by a trans electrode 22, and an upper surface 46 that is defined by the membrane 18. Thus, each trans well 16 is formed within the space defined by the trans electrode 22, sidewalls 40, and the membrane 18. It is to be understood that the upper surface 46 has opening/channel 13 through the nanopore(s) 20 positioned in the membrane 18.

The trans electrode 22, whose interior surface is the lower surface 44 of the trans well 16, may be physically connected to a substrate (not specifically illustrated). The trans electrode 22 may be fabricated in the process of forming the substrate (e.g., during the formation of the trans well 16). Microfabrication techniques that may be used to form the trans well 16 and the trans electrode 22 include lithography, metal deposition and liftoff, dry and/or spin on film deposition, etching, etc. The interface between the trans electrode 22 and any underlying substrate may seal the lower portion of the trans well 16.

The trans electrode 22 that is used depends, at least in part, upon the electrolyte species in the electrolyte solution 24. The trans electrode 22 may be an active electrode that takes part in the chemical reaction with an electrochemically active electrolyte species, and can be oxidized or reduced in the half-cell reaction. Any of the examples of the active electrodes set forth herein for the cis electrode 14 may be used as the trans electrode 22. In other examples, the trans electrode 22 may be an inactive (or inert) electrode that transfers electrons rather than exchange ions with the electrolyte solution 24. Any of the examples set forth herein for the cis electrode 14 may be used as the trans electrode 22. In an example in the nanopore sensor 10 utilizing an electrolyte solution 24 with an electrically active anion (e.g., chloride, $Cl^-$), the trans electrode 22 may be a silver/silver chloride (Ag/AgCl) electrode.

While one cis well 12 and one trans well 16 are shown in FIG. 1, it is to be understood that the nanopore sensor device 10 may include one or several cis wells 12 that are fluidically isolated from one another and are fluidically connected to respective trans wells 16. Multiple cis wells 12 may be desirable, for example, in order to enable the measurement of multiple samples in a single device.

The nanopore 20 has two open ends and an opening/channel 13 (which also may be referred to as a hollow core or hole) that connects the two open ends. The walls of the opening/channel 13 are an inner surface 48 of the nanopore 20. When inserted into the membrane 18, one of the open ends of the nanopore 20 faces the cis well 12 and the other of the open ends of the nanopore 20 faces the trans well 16 and is aligned with at least a portion of the opening of trans well 16. The hollow opening/channel 13 of the nanopore 20 enables the fluidic connection between the wells 12, 16. The diameter of the opening/channel 13 may range from about 1 nm up to 1 μm, and may vary along the length of the nanopore 20. In some examples, the open end that faces the cis well 12 may be larger than the open end that faces the trans well 16. In other examples, the open end that faces the cis well 12 may be smaller than the open end that faces the trans well 16.

The nanopore(s) 20 may be inserted into the membrane 18, or the membrane 18 may be formed around the nanopore(s) 20. In an example, the nanopore 18 may insert itself into a formed membrane 18 (such as a lipid bilayer, which is one nonlimiting example of the membrane 18). For example, a nanopore 20 in its monomeric form or polymeric form (e.g., an octamer) may insert itself into the membrane (e.g., lipid bilayer) and assemble into a transmembrane nanopore. In another example, the nanopore 20 may be added to a grounded side of a membrane (e.g., lipid bilayer) at a desirable concentration where it will insert itself into the membrane. In still another example, the membrane (e.g., lipid bilayer) may be formed across an aperture in a polytetrafluoroethylene (PTFE) film and positioned between the cis and trans wells. The nanopore 20 may be added to the grounded cis compartment, and may insert itself into the membrane at the area where the PTFE aperture is formed. In yet a further example, the nanopore 20 may be tethered to a solid support (e.g., silicon, silicon oxide, quartz, indium tin oxide, gold, polymer, etc.). A tethering molecule, which may be part of the nanopore 20 itself or may be attached to the nanopore 20, may attach the nanopore 20 to the solid support. The attachment via the tethering molecule may be such that a single nanopore 20 is immobilized (e.g., between two chambers/wells). A membrane (e.g., lipid bilayer) may then be formed around the nanopore 20.

The nanopore sensor device 10 also includes electronics to address trans electrode 22. As mentioned herein, trans well electrode 22 is associated with a respective trans well 16 and a respective nanopore 20. Some of the electronics are schematically shown in the form of circuitry 160 in FIG. 1. The electronics include at least a stimulus source and a controller. The stimulus source is coupled to trans electrode 22 and is to cause an ionic current to flow through nanopore 20 responsive to actuation by the controller. Circuitry 160 may also include an amplifier to amplify the electrical signal passing through nanopore.

Further details regarding nanopore 20, positively charged species 30, and options thereof, will be described below.

Example Modifications to Nanopores

Figure 2:
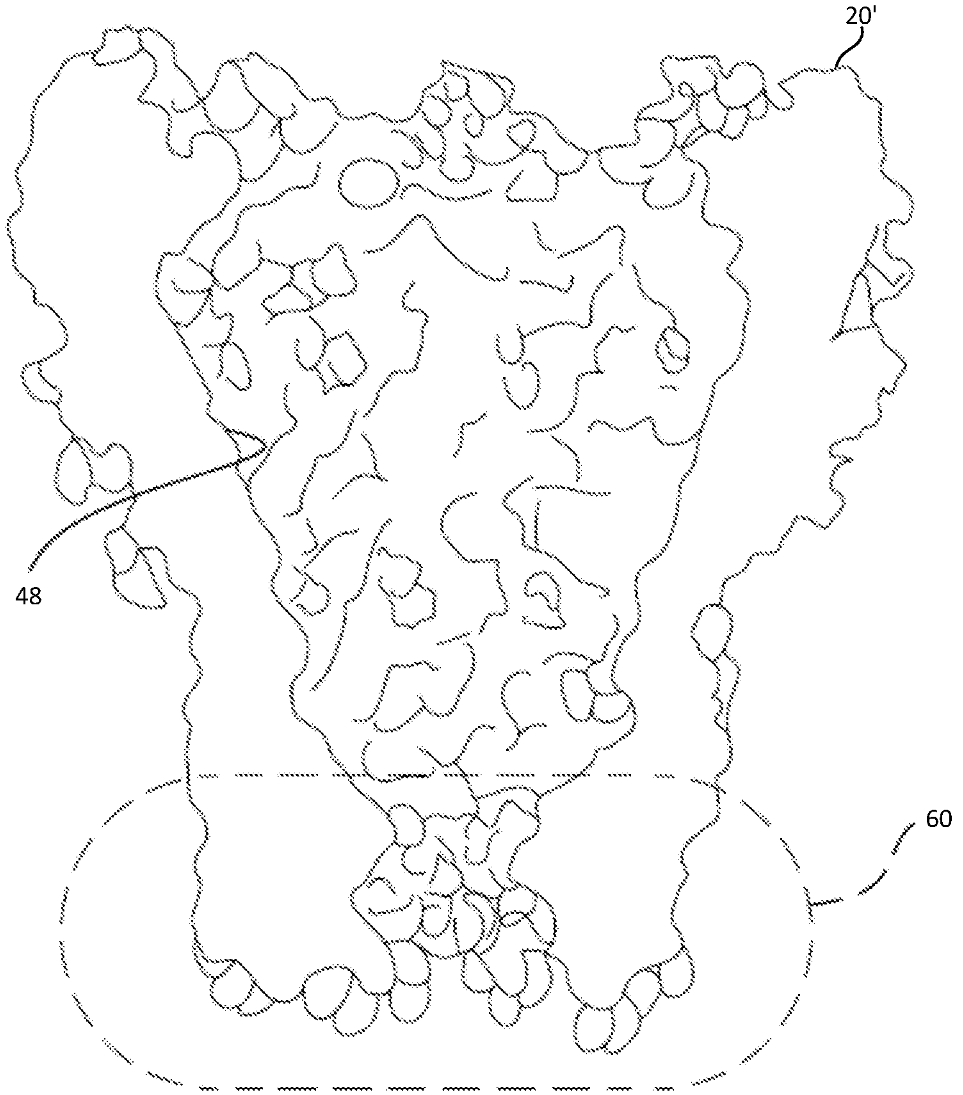
FIG. 2 is an enlarged and schematic view of a nanopore having a plurality of positively charged residues on an inner surface thereof.

In some examples, the nanopore sensor device 10 includes a modified nanopore 20' in the position of nanopore 20. An example of the modified nanopore 20' is depicted in FIG. 2.

The modified nanopore 20' may include a protein (polypeptide) the inner surface 48 of which has been modified to introduce at least one fixed positive charge (referred to as positively charged residues) in place of a negative charge or a neutral charge. In protein nanopores, the positive charges may be introduced in the form of positively charged amino acid residues, such as arginine and lysine. Negatively charged amino acid residues and/or neutral amino acid residues can be mutated to the positively charged amino acid residues. The positive charges may also be introduced by mutating selected amino acid residues to cysteine, and then functionalizing the cysteine residues with a positive charge using a cysteine-reactive linker, such as maleimide. Non-limiting examples of the manner in which residues on polypeptide nanopores may be functionalized with positive charges are described below with reference to FIGS. 3A-3C, 4A-4B, 5A-5C, 6A-6C, 7A-7C, 8A-8C, 9A-9C, 10, and 11.

The introduction of the positively charged residues to the inner surface 48 may exclude or reduce cations 160, such as reactive electrolyte species $C^+$, from transporting through the modified nanopore 20' in similar manner as positively charged species 30 inhibits transport of cations 160 through nanopore 20 as described with reference to FIG. 1.

Nanopore 20 or modified nanopore 20' may have any suitable structure. In some examples, the modified nanopore 20' is a modified protein nanopore in which one or more negatively charged residues, one or more neutral charged resides, or both negatively charged residues and neutral charged residues are mutated to one or more positively charged residues. Similarly, in some examples, nanopore 20 is a modified protein nanopore in which one or more negatively charged residues, one or more neutral charged resides, and/or one or more positively charged residues are mutated to one or more reactive residues that may be coupled to positively charged species in a manner such as will be described in greater detail with reference to FIGS. 4A-4B, 5A-5C, 6A-6C, 7A-7C, 8A-8C, 9A-9C, 10, and 11.

Many protein nanopores exhibit at least 7-fold symmetry, meaning that they are composed of seven or more identical polypeptide chains that assemble as a ring with symmetry determined by the number of individual chains. This symmetry can allow for the simultaneous mutation of each subunit of a single type of amino acid residue to completely alter the charge of the inner surface 48 (in the case of nanopore 20') or to couple positively charged species 30 to each subunit (in the case of nanopore 20). In some instances, however, it may be desirable to mutate less than each subunit of the single type of amino acid residue, thus introducing fewer charges to the modified nanopore 20' or coupling fewer positively charged species 30 to nanopore 20. In these instances, it may be desirable to mutate some subunits (but not all 7, 8, etc.) of a particular residue, or by appropriately mutating a single-chain of the protein nanopore (e.g., point mutations). Nonlimiting examples of the manner in which identically or differently mutated subunits of a protein nanopore may be coupled together in order to provide a desired number of positively charged species 30 at desired respective locations in the assembled nanopore are described further below with reference to FIGS. 5A-5C, 6A-6C, 7A-7C, 8A-8C, and 9A-9C.

As one example, the protein nanopore is MspA, which is octameric, i.e., has 8-fold symmetry. In nonlimiting examples of nanopore 20', the positively charged residues 48 may carry a charge of +1 or +2, which enables from 8 positive charges to 16 positive charges to be introduced at the inner surface 48 per residue type that is mutated (assuming all 8 of the residues are mutated, one per MspA subunit). Similarly, in nonlimiting examples of nanopore 20, positively charged species 30 may carry a charge of +1 or +2, which enables from 8 positive charges to 16 positive charges to be coupled to nanopore 20 per residue type that is mutated (assuming all 8 of the residues are mutated, one per MspA subunit). The assembled MspA protein has an ultra-narrow (e.g., ~1 nm) and ultra-short (~2 nm) channel, and thus the addition of about 2.8 positive charges may be desirable for substantially reducing or eliminating transport of cations 160, e.g., reactive electrolyte species $C^+$ (see Example 1).

In one example, the negatively charged aspartic acid residues D139 and D118 of the MspA nanopore may be mutated to positively charged arginine or lysine. This positioning may aid in attracting a nucleotide sample to the modified nanopore 20' and also electrostatically repel cations, e.g., reactive electrolyte species $C^+$, that are present in the cis well 12. Alternatively, such residues may be mutated to include a reactive moiety that can be used to couple nanopore 20 to positively charged species 30, e.g., in a manner such as described in greater detail below with reference to FIGS. 4A-4B, 5A-5C, 6A-6C, 7A-7C, 8A-8C, 9A-9C, 10, and 11.

In another example, the negatively charged aspartic acid residues D90, D91, and/or D93 of the MspA nanopore may be mutated to positively charged arginine or lysine. These residues reside at the narrow constriction zone 60 of the MspA nanopore. Thus, in some examples, the plurality of positively charged residues on the inner surface 48 is located at the constriction zone 60 of the modified nanopore 20'. As examples, the negatively charged aspartic acid residues D90, D91, and/or D93 may be respectively mutated to D90R, D91R, and/or D93R, which would introduce 1 or 2 positive charges per subunit. In other examples, the negatively charged aspartic acid residues D90, D91, and/or D93 may be respectively mutated to D90K, D91K, and/or D93K or D90H, D91H, and/or D93H. Any combinations of the D90, D91, and/or D93 mutations may also be made. Residues D90 and D91 are the most solvent-exposed, and thus may be the greatest determinant of cation repulsion when mutated to include the positively charged residues. Alternatively, any of such residues may be mutated to include a reactive moiety that can be used to couple nanopore 20 to positively charged species 30, e.g., in a manner such as described in greater detail below with reference to FIGS. 4A-4B, 5A-5C, 6A-6C, 7A-7C, 8A-8C, 9A-9C, 10, and 11.

Table 1 sets forth additional examples of protein nanopores and proposed inner surface modifications that may provide repulsion of cation 160, e.g., reactive electrolyte species $C^+$, when used as the modified nanopores 20' in the nanopore sensor device 10. Alternatively, the noted residues may be mutated to include a reactive moiety that can be used to couple nanopore 20 to positively charged species 30, e.g., in a manner such as described in greater detail below with reference to FIGS. 4A-4, 5A-5C, 6A-6C, 7A-7C, 8A-8C, 9A-9C, 10, and 11; in such options, the residue may be mutated to include a residue other than that stated in Table 1. The proposed net charge equals the charge introduced if the proposed mutation, e.g., positively charged mutation, were performed at each subunit of the negatively or neutrally charged residue being replaced. As such, it may be desirable to mutate some subunits (but not all 7, 8, or 9) of a particular residue, or to mutate a single-chain or two chains of the protein nanopore (e.g., point mutations). Nonlimiting examples of preparing nanopores in which only a portion of the subunits are modified are described with reference to FIGS. 6A-6C, 7A-7C, 8A-8C, and 9A-9C. In such examples the net charge may be reduced from that shown in Table 1 based on the number of subunits which are modified).

TABLE 1

| Protein NP | X-fold Symm. | Diameter/ Height (nm/nm) | Const. Zone Area ($nm^2$) | Net Charge Density for cation (e.g., $C^+$) Repulsion | Proposed + Mutation | Proposed Net Charge (where all subunits are modified) |
|---|---|---|---|---|---|---|
| CsgG | 9 | 1.3/0.3 | 1.2 | 0.4 | F56R or F56K | +9 |
| #CsgG/ CsgF | 9 | 1.5/1 | 4.7 | 1.4 | N17R | +9 |
| Fragaceatoxin C | 8 | 1.6/1 | 5.0 | 1.5 | D10R | +8 |
| Aerolysin | 7 | 1.3/9.3 | 38.0 | 11.4 | D216N and D222N and E258Q and E254Q | +14 |
| *aerolysin | 7 | 1.3/1.3 | 5.3 | 1.6 | (D216N and D222N) or (E254Q and E258Q) | +7 |

TABLE 1-continued

| Protein NP | X-fold Symm. | Diameter/ Height (nm/nm) | Const. Zone Area ($nm^2$) | Net Charge Density for cation (e.g., $C^+$) Repulsion | Proposed + Mutation | Proposed Net Charge (where all subunits are modified) |
|---|---|---|---|---|---|---|
| aHL | 7 | 1.2/5.5 | 20.7 | 6.2 | E111Q and D127N | +14 |
| *aHL | 7 | 1.2/1.3 | 4.9 | 1.5 | E111Q or D127N | +7 |
| MspA | 8 | 2.2/1.2 | 8.3 | 2.5 | (D90R and D91N) or (D90N and D91R) | +8 |

#Denotes second constriction zone conferred by CsgF binding the CsgG nanopore
*Denotes calculation of only a small section of the overall constriction zone area Note that the net charge density of a given constriction zone within a nanopore was calculated using the surface area of just the sides of a cylinder (Area=π×Diameter×Height). A net charge of 0.3 charges per $nm^2$ is estimated to be needed to achieve ion selectivity. Taking MspA for example, the constriction zone is approximately 2.2 nm in height (H) and approximately 1.2 nm in diameter (D), so the surface area was calculated to be about π×D×H=3.14×1.2×2.2 which is ~8.3 $nm^2$. For a net charge of 0.3 charges per $nm^2$ (which is estimated to be needed to achieve ion selectivity) the total net charge is estimated to be 0.3 charges/$nm^2$×8.3 $nm^2$=a net charge of approximately +2.5. It will be appreciated that the estimation of the constriction zone's surface area is fairly subjective, and as such the values shown in Table 1 are intended to reflect addition of significantly more charge in the constriction than is believed to be needed to ensure ion selectivity.

The CsgG protein nanopore shares a narrow constriction zone 60 defined by residues N55 and F56, although this constriction happens within the middle of the larger nanopore where the surface is defined by the loop of residues 46-61. The measured dimensions of this nanopore are 1.3 nm diameter and 0.3 nm in height. A net charge of 0.4 may be sufficient to effect cation repulsion in this tiny channel (1.2 $nm^2$). If CsgF peptides are added to the CsgG nanopore (resulting in CsgG/CsgF, which also may be referred to as CsgGF), a second constriction zone is formed approximately 3 nm below the first (going from cis to trans). This constriction zone is defined by residue N17. In this example, ion selectivity may be imparted at one or both constriction zones using the positive amino acid mutations disclosed herein.

The fragaceatoxin C nanopore is unique among ssDNA threading nanopores due to the alpha-helical nature of the transmembrane portion, which also defines the narrow constriction zone 60 where residue D10 imparts a negative charge. Cation repulsion may be achieved by mutating one or more of the eight D10 negatively charged residues.

Each of aerolysin and alpha-hemolysin (aHL) has a long and narrow barrel constriction zone 60 that, via symmetry, is defined by two-beta-strands. The internal surface charge of the barrel could be modulated to impart a net positive charge at any point throughout. Even with the 9.3 nm barrel height of the aerolysin nanopore, an overall net charge of >+11 could be achieved with two modest mutations, D216N and E254Q, which neutralize two negatively charged side chains on the barrel interior surface and effectively cap the barrel with two positive rings made by R282 and K242. The alpha-hemolysin barrel is smaller, about 5.5 nm in height, but could similarly be modulated to have positively charged rings on the entry and exit by neutralizing mutations, E111Q and D127N. In this example, the positive rings may be defined by residues K147 and K131.

For MspA, there are two wild type residues that are negatively charged within the constriction zone, D90 and D91. In order to provide a net+charge it may be insufficient to change just one of these two residues to a positive charge; the other charged residue may be neutralized. The two options are shown in parentheses in Table 1, in which one option puts a positive charge at D90 to R and neutralizes D91 to N, and the other option neutralizes D90 to N and adds the charge on D91 to R. So in Table 1, if "and" is used it means the mutations relative to wild type are combined, and if "or" is used it means either option will provide the desired net charge. The first letter in the mutations listed in Table 1 refers to the wild type residue, and the second letter is the mutation.

An example of a method of detecting an ionic current to analyze a biological compound includes providing a nanopore 20' or nanopore 20 within a membrane 18 separating a cis well 12 and a trans well 16, the nanopore 20' having a plurality of positively charged residues on an inner surface 48 of the nanopore 20', or nanopore 20 having a plurality of positively charged residues 30 coupled thereto; providing an electrolyte fluid 24 within the cis well 12 and the trans well 16; and applying an electric current between a cis electrode (cathode) 14 at least partially exposed to the cis well 12 and a trans electrode (anode) 22 at least partially exposed to the trans well 16 to generate an ionic current through the nanopore 20' or 20 wherein the plurality of positively charged residues of the nanopore 20' or 20 inhibits translocation of a cation 160, e.g., reactive electrolyte species $C^+$, from the trans well 16 to the cis well 12 during application of the electric current.

In some examples of this method, the electrolyte solution 24 may include any reactive electrolyte species 160, 170 ($C^+$, $A^-$) that is capable of dissociating into counter ions (a cation 160 $C^+$ and its associated anion 170 $A^-$), wherein one of the counter ions, e.g., the cation $C^+$ or the anion $A^-$, participates in a half reaction at the cis electrode 14 and the trans electrode 22. This electrolyte solution 24 also includes a polar solvent, such as water.

In some examples, the cis well 12 includes an electrolyte solution with a higher concentration of cations 160 and anions 170, e.g., reactive electrolyte species $C^+$, $A^-$, and the trans well 16 includes an electrolyte solution with a lower concentration of the cations 160 and anions 170, e.g., reactive electrolytes species $C^+$, $A^-$. As such, the cis well 12 includes a higher concentration of the reactive electrolyte species $C^+$, $A^-$ than the trans well 16 during application of the electric current. When the modified nanopore 20' or nanopore 20 and the different electrolyte solutions are used together in the nanopore sensor device 10, several beneficial effects may be achieved: the magnitude of the fixed charge of the modified nanopore may be reduced (as opposed to when the same electrolyte solution 24 is used in the cis and trans wells 12, 16); the magnitude of the concentration gradient may be reduced (as opposed to when a non-modified nanopore is utilized), which reduces the osmotic pressure differential across the membrane 18; and the nanopore current may increase.

When the electrolyte 24 or the different electrolyte solutions are contained within the cis well 12 and trans wells 16, a nucleotide sample may be added to the cis well 12, e.g., via a fluid inlet (not specifically illustrated). The controller may then be used to activate the stimulus source to address trans electrode 22. The stimulus source (e.g., a current source, a voltage source) causes an ionic current to flow through the modified nanopore 20' or nanopore 20.

In this example method, the application of the electric current between the cis electrode (cathode) 14 and the trans electrode (anode) 22 may be initiated by the stimulus source, which applies a voltage bias between the cis well 12 and trans well 16 and across the membrane 18. In some examples, the applied electric current is a unipolar electric current. In other examples, the applied current is an alternating electric current between the cis electrode 14 and the trans electrode 22. In this example, the voltage polarity is typically applied such that a negatively charged element, such as a nucleotide, may be electrophoretically driven toward or into the modified nanopore(s) 20' or nanopore 20. As an example, the voltage may range from about 5 mV to about 500 mV (of either polarity).

The cis-trans voltage bias causes ionic current to flow through the modified nanopore 20' or 20. The current flow across the modified nanopore(s) 20' or 20 causes motion of one or more elements, such as nucleotides, towards the trans well, and causes translocation of anions A– through the modified nanopore 20' or nanopore 20. In some examples, the current flow forces the translocation of one or more elements, such as nucleotide(s) or a label coupled thereto, through the modified nanopore 20' or nanopore 20 along with the anions $A^-$ carrying the charge. The positively charged residues of the modified nanopore 20' or the positively charged species 30 of nanopore 20 may also help to attract the negatively charged nucleotides. Moreover, the positively charged residues may also electrostatically repel cations 160 $C^+$ of the electrolyte solution, e.g., to inhibit translocation of the cations through modified nanopore 20' or nanopore 20. Due to the cationic repulsion induced by the at least partially positively charged surface of the modified nanopore 20' or positively charged species 30 of nanopore 20, the ionic current includes an amount of anions $A^-$ of the electrolyte $C^+$, $A^-$ translocating through the modified nanopore 20' to the trans well 16 that is higher than an amount of cations $C^+$ of the electrolyte $C^+$, $A^-$ translocating through the modified nanopore 20' from the trans well 16. This effect may be enhanced when the varying concentration electrolyte solutions are used in combination with the modified nanopore 20'.

The modified nanopore 20' or nanopore 20 reduces or retards transport of the cations $C^+$ through the nanopore 20, either via drift induced by the voltage bias or diffusion. As such, the initial cation $C^+$ current at t=0 is reduced and even eliminated. In this manner, the anions $A^-$ are forced to carry the majority of the ionic current from t=0 onward, so the initial decrease in current is mitigated, and the overall current will remain more stable throughout the sensing run.

The useful life of the nanopore sensor device 10 may be extended, in part because a greater proportion of the current is forced to be carrier through the nanopore 20' or 20 by the otherwise limiting anions $A^-$.

Further details regarding preparation of nanopore 20 now will be provided with reference to FIGS. 3A-10. It will be appreciated that such preparation suitably may be modified to prepare nanopore 20'.

Figure 3A:
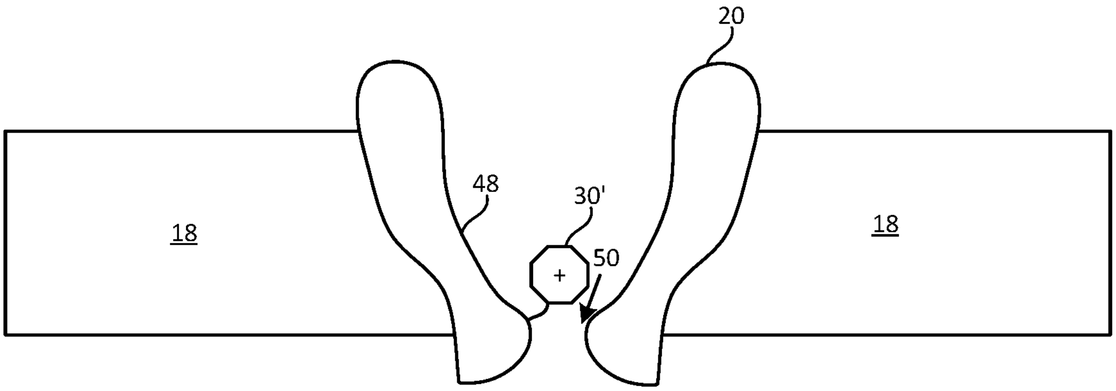
FIGS. 3A-3C schematically illustrate alternative polypeptide nanopores synthetically functionalized with one or more positively charged species.
Figure 3B:
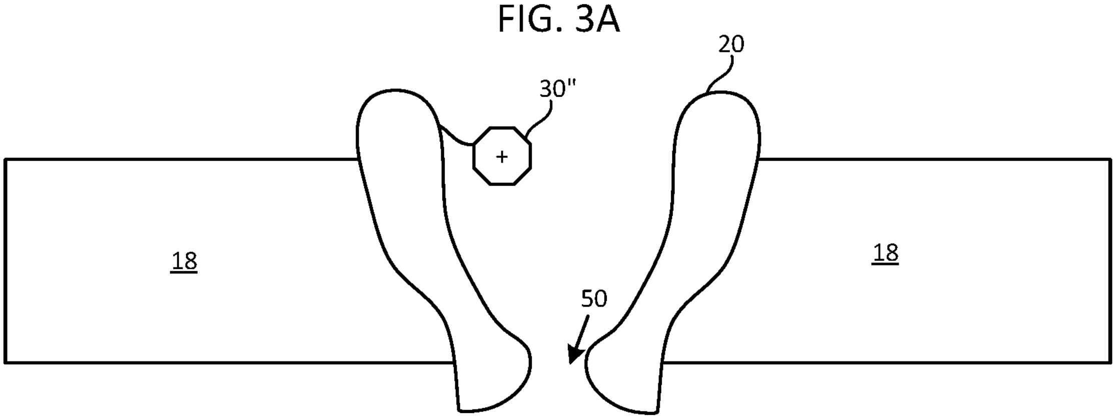
Figure 3C:
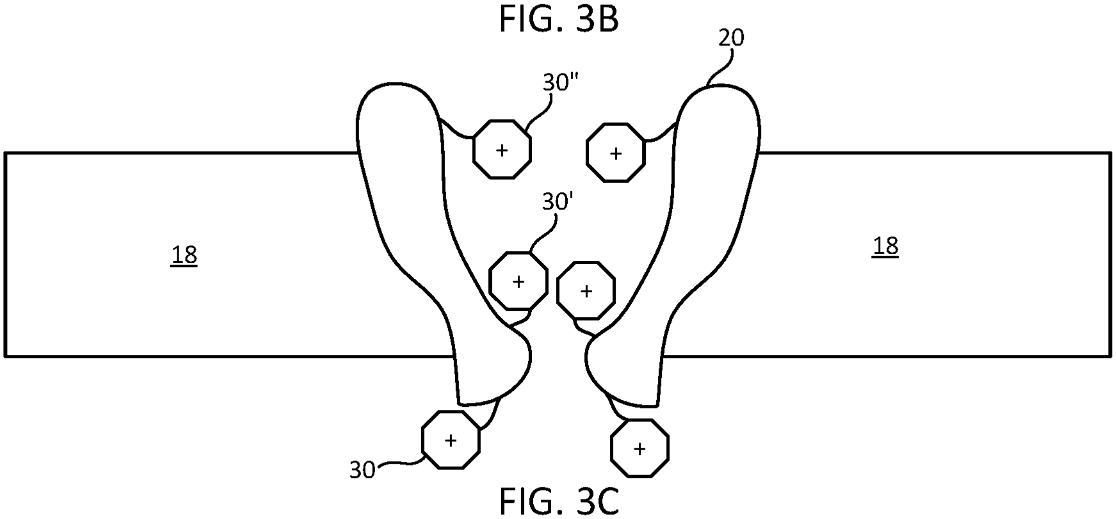

Positively charged species 30 may be coupled to nanopore 20 at any suitable location(s). For example, as illustrated in FIG. 1, positively charged species 30 may be coupled to nanopore 20 at a location which is outside of aperture 13 and is below the constriction of the nanopore (e.g., on the trans side of the nanopore in examples in which the constriction 50 is oriented toward the trans side of the device, or on the cis side of the nanopore in examples in which the constriction 50 is oriented toward the cis side of the device). Such a location disposes positively charged species 30 at a location which is sufficiently close to constriction 50 that positively charged species 30 may inhibit translocation of cations 160 through the aperture 13 of the nanopore, and in particular through constriction 50. FIGS. 3A-3C schematically illustrate alternative polypeptide nanopores synthetically functionalized with one or more positively charged species. In the nonlimiting example illustrated in FIG. 3A, positively charged species 30' is coupled to the interior surface 48 of nanopore 20 at a location which is within constriction 50, or sufficiently close to constriction 50 that positively charged species 30 may inhibit translocation of cations 160 through the aperture 13 of the nanopore, and in particular through constriction 50. In the nonlimiting example illustrated in FIG. 3B, positively charged species 30" is coupled to the interior surface 48 of nanopore 20 at a location which is spaced apart from constriction 50 and is above the constriction (e.g., on the cis side of the nanopore in examples in which the constriction 50 is oriented toward the trans side of the device, or on the trans side of the nanopore in examples in which the constriction 50 is oriented toward the cis side of the device). Although positively charged species 30" may be further from constriction 50, the species still may be sufficiently close to constriction 50 that positively charged species 30" may inhibit translocation of cations 160 through the aperture 13 of the nanopore. In some examples, nanopore 20 may be coupled to any suitable combination of positively charged species 30, 30', 30", e.g., so as to further inhibit or prevent translocation of cations 160 through the aperture 13 of the nanopore. For example, FIG. 3C illustrates an example in which nanopore 20 includes a plurality of species 30, a plurality of species 30', and/or a plurality of species 30". It will be appreciated that references elsewhere herein (such as regarding FIG. 1) to "species 30" are intended to encompass positively charged species that are coupled to any suitable location of nanopore (such as illustrated in FIGS. 3A-3C), and are not intended to be limited to the particular location specifically illustrated in FIG. 1.

Species 30, 30', and/or species 30" may be coupled to nanopore 20 via any suitably mutated residues of any suitable nanopores, e.g., residues such as described with reference to modified nanopore 20'. For example, positively charge species may be coupled to any wild type or mutant protein nanopore construct that is ionically conductive. This includes polypeptide nanopores such as MspA, FraC, α-Hemolysin, CsgG, and others. The descriptions provided henceforth will primarily focus on MspA, but readily may be adapted for use with other types of polypeptide nanopores.

Example Positions of Mutation

A number of different residues in the nanopore respectively can be mutated for use in synthetically functionalizing the nanopore with the positively charged species 30. In some examples, one or more residue(s) forming or within the constriction site 50 in the nanopore 20 may be mutated, as this site has the strongest influence on the final current through the nanopore. In MspA, residues 90, 91, and 93 are positioned in and around the inner portion of the constriction site, making these positions useful for functionalization with positively charged species 30 in a manner such as described with reference to FIG. 3A. Aside from internal residues along the constriction site, residues around the external base of the nanopore, below the constriction (e.g., the end that is in contact with the trans well in a manner such as described with reference to FIG. 1) may be modified in order to inhibit cation translocation from the trans well to the cis well. Residues in the vestibule and rim of the nanopore could also be modified, e.g., in a manner such as described with reference to FIG. 3B, although these may have a weaker influence on the electrolyte depletion issue when compared to residues near the constriction site 50.

Example Residues for Mutation

The targeted nanopore residue(s) respectively may be mutated to a natural or unnatural amino acid that may be synthetically modified after the mutation. In some examples, the mutations are or include residues that (i) are not present in other parts of the protein, and/or (ii) are uniquely reactive to the chosen chemistry used to synthetically functionalize the nanopore. Both (i) and (ii) are useful for ensuring the modification is site-selective and does not compromise other parts of the protein.

For example, mutation of select amino acids into cysteine residues may be a particularly useful route to introducing positively charged species into nanopore due to the selective reactivity of the thiol (—SH) groups in cysteine. Cysteine mutations are also attractive when seeking to introduce site-specific modifications to MspA, seeing as neither the wild type nor MspA mutants used in nanopore sequencing include cysteine residues at other positions. Mutations to other natural amino acids, including (but not limited to) lysine, tyrosine, selenocysteine, methionine, and serine may also be introduced as handles to synthetically functionalize the nanopore with positively charged species. As a relatively uncommon amino acid, selenocysteine may be useful for selectively functionalizing proteins that already have an abundance of the more common reactive residues, such as cystine. Unnatural or non-canonical amino acids (e.g., an alkyne-containing residue such as homopropargylglycine or hydroxyphenylglycine; an azide-containing residue such as azidohomoalanine; or an alkene-containing residue such as homoallylglycine) may also or alternatively be introduced into nanopore protein such that modifications to induce cation-blocking are bio-orthogonal. Accordingly, it will be appreciated that each mutated amino acid residue independently may include a natural amino acid residue such as cysteine, serine, tyrosine, lysine, phenylalanine, tryptophan, methionine, or selenocysteine, or an unnatural amino acid residue such as homopropargylglycine, hydroxyphenylglycine, azidohomoalanine, or homoallylglycine.

Example Synthetic Functionalization of the Mutated Residue

The point mutation(s) introduced into the polypeptide nanopore 20 may be used for the conjugation of positively charged species 30 at a corresponding location within the nanopore, e.g., at location(s) such as described with reference to FIGS. 1, 3A, 3B, and/or 3C. For nanopores that are composed of multiple protein subunits (such as MspA, CsgG, CsgG/CsgF, Fragacea-toxin C, Aerolysin, and aHL), the coupling of the positively charged species to mutated residues can be performed on the individual protein subunits prior to the assembly of the nanopore, e.g., in a manner such as will be described with reference to FIG. 4A-4B, or may be performed after the subunits have assembled into the final nanopore complex, e.g., in a manner such as will be described with reference to FIG. 5A-5C, 6A-6C, 7A-7C, 8A-8C, or 9A-9C. Optionally, the positively charged species may be coupled to the nanopore or to one or more subunits thereof as a neutral species to which a positive charge subsequently is added, e.g., in a manner such as will be described with reference to FIG. 10. Nonlimiting options of positively charged species that can be coupled to nanopores, or to subunit(s) thereof, are described further below.

Figure 4A:
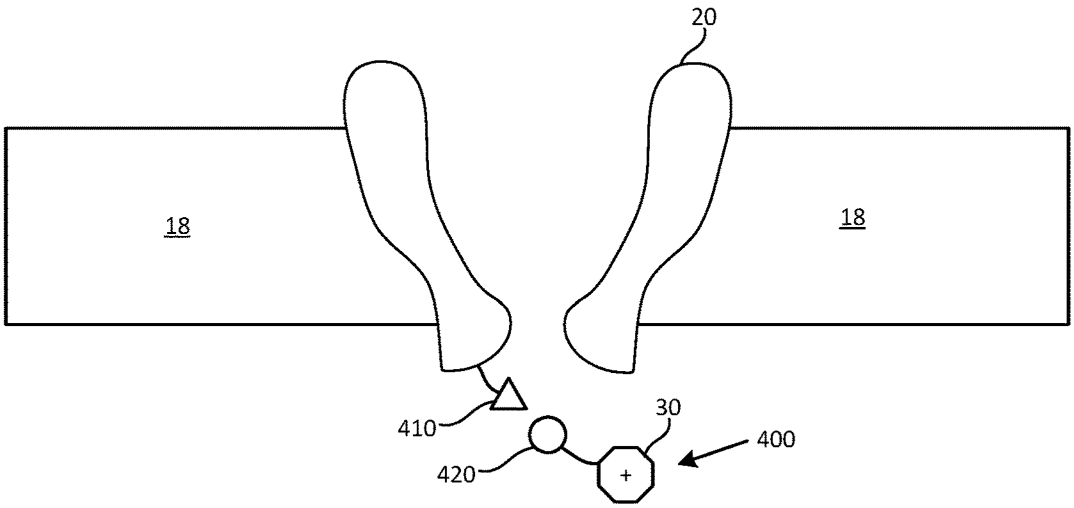
FIGS. 4A-4B schematically illustrate operations in an example method for synthetically functionalizing a polypeptide nanopore with a positively charged species.
Figure 4B:
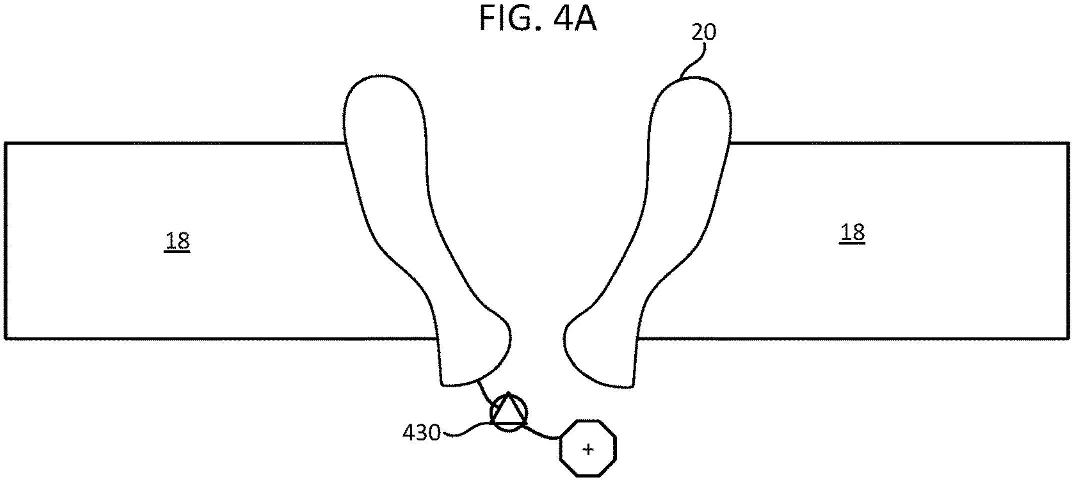
Figure 10:
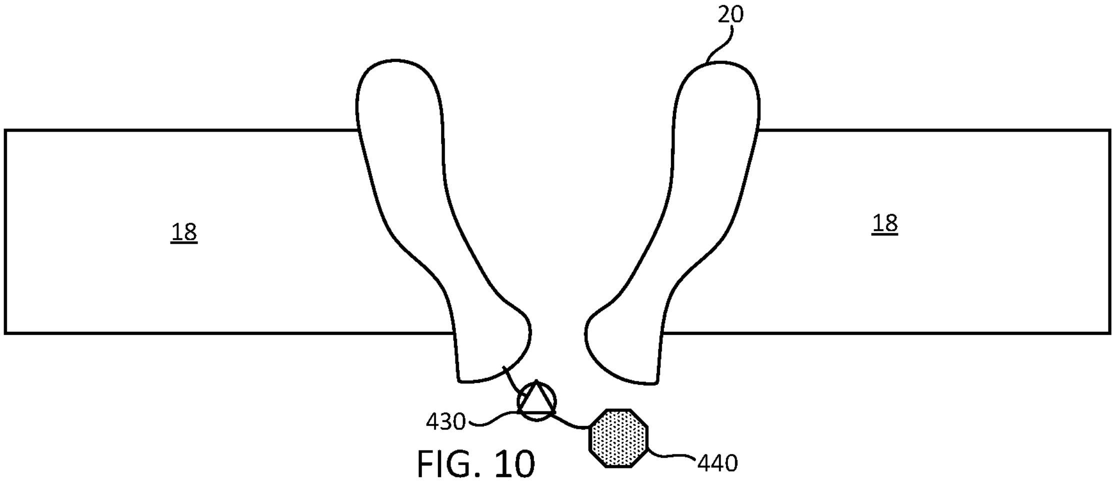
FIG. 10 schematically illustrates an alternative operation in an example method for synthetically functionalizing a polypeptide nanopore with a positively charged species.

FIGS. 4A-4B schematically illustrate operations in an example method for synthetically functionalizing a polypeptide nanopore with a positively charged species. In the nonlimiting example illustrated in FIG. 4A, any suitable residue of nanopore 20 is mutated so as to include first reactive moiety 410. The nanopore may be contacted with bifunctional molecule 400 including positively charged species 30 coupled to second reactive moiety 420. In a manner such as illustrated in FIG. 4B, first reactive moiety 410 may react with second reactive moiety 420 so as to generate reaction product 430 coupling positively charged species 30 to nanopore 20. FIG. 10 schematically illustrates an alternative operation in an example method for synthetically functionalizing a polypeptide nanopore with a positively charged species. In the nonlimiting example illustrated in FIG. 10, molecule 400 may include a precursor 440 coupled to second reactive moiety, and first reactive moiety 410 may react with second reactive moiety 420 so as to generate reaction product 430 coupling the precursor to nanopore 20. Precursor 440 subsequently may be converted to positively charged species 30 using one or more additional operations. In one nonlimiting example, precursor 440 coupled to nanopore 20 via reaction product 430 includes a neutral species, and a positive charge may be installed in the neutral species following such coupling to provide positively charged species 30. Accordingly, unless indicated otherwise, it is intended herein that any reference to synthetically functionalizing (or coupling) a nanopore, or subunit thereof, to a positively charged species also encompasses the option in which the nanopore is synthetically functionalized to a precursor that then is converted into positively charged species 30, e.g., by installing a positive charge in a neutral species.

Depending on the chemical functionality of the chosen mutation, a number of different reactions can be employed to covalently install the desired positively charged species. That is, there are many different options for first reactive moiety 410 and second reactive moiety 420 the reaction product 430 of which may be used to synthetically functionalize nanopore 20 with positively charged species 30. For example, the thiol (—SH) groups (first reactive moiety 410) in cysteine can be selectively modified through a multitude of chemistries (options for second reactive moiety 420) owing to the nucleophilic character of the sulfur atom. The chemoselective reaction of thiols and maleimides is a classic example of this, where a functionalized maleimide (second reactive moiety 420) can be grafted onto the exposed cysteine group via a Michael addition. Cysteine residues can also be modified through a radical thiol-ene "click" reaction, aminoethylation, disulfide bond formation with other functionalized thiols, or even converted into an alkene for subsequent modifications. For further details regarding options for reactions with amino acid residues such as cysteine, see Spicer et al., "Selective chemical protein modification," Nature Communications 5, Article Number: 4740 (2014), the entire contents of which are incorporated by reference herein. Treatment of cysteine residues with certain organometallic catalysis may also be used to selectively couple the protein to aromatic rings that are substituted with cationic species. For further details regarding such an approach, see Vinogradova et al., "Organometallic palladium reagents for cysteine bioconjugation," Nature 526(7575): 687-691 (2015), the entire contents of which are incorporated by reference herein.

The introduction of serine, tyrosine, lysine, phenylalanine, tryptophan, methionine, selenocysteine, and other natural amino acid mutations may also be used as a handle for synthetically functionalizing the nanopore using chemistries (reactions between first reactive moieties 410 and second reactive moieties 420) such as described in the following references, the entire contents of each of which are incorporated by reference herein: Vantourout et al., "Serine-selective bioconjugation," J. Am. Chem. Soc. 142 (41): 17236-17242 (2020); Sato et al., "Site-selective protein chemical modification of exposed tyrosine residues using tyrosine click reaction," Bioconjugate Chem. 31(5): 1417-1424 (2020); Griffiths et al., "Site-selective modification of peptides and proteins via interception of free-radical-mediated dehalogenation," Angew. Chem. Int. Ed. 59(52): 23659-23667 (2020); Cohen et al., "An Umpolung approach for the chemoselective arylation of selenocysteine in unprotected peptides," J. Am. Chem. Soc. 137(31): 9784-9787 (2015); and Krall et al., "Site-selective protein-modification chemistry for basic biology and drug development," Nature Chemistry 8: 103-113 (2016). Illustratively, like cystine, selenocysteine may be modified using a series of reactions involving oxidation and a metal-mediated cross-coupling (e.g., in a manner such as described in Cohen et al.), or a radical-mediated dehalogenation (e.g., in a manner such as described in Griffiths et al.)

It will be appreciated that wide range of chemistries may be used to selectively functionalize canonical amino acids (first reactive moiety 410) with positively charged species (via reaction between first reactive moiety 410 and second reactive moiety 420 coupled to the positively charged species. For example, these reactions can fall in the one or more of the following categories: reaction with an oxidizing or reducing agent, treatment with an acid or base, nucleophilic addition, metal-mediated cross-coupling, photo- or redox-catalyzed homolysis or heterolysis, metathesis, ether or esterification, amination or amidation, aromatic substitution, dehydroalanination, ligation, cycloadditions, condensation, or various light-mediated reactions.

Alternatively, mutation to unnatural amino acids incorporating, as reactive moiety 410, azide groups (e.g. azidohomoalanine) or alkynes (e.g. hydroxyphenylglycine) allow for positively charged species or precursors thereof to be introduced via Cu(I)-catalyzed "click" chemistry (reactions between first reactive moiety 410 and second reactive moiety 420). Such an approach may be utilized for highly efficient orthogonal synthetic functionalization of the nanopore, e.g., using a reaction such as described in Besanceney-Webler et al., "Increasing the efficacy of biorthogonal click reactions for bioconjugation: a comparative study," Angew. Chem. Int. Ed. Engl. 50(35): 8051-8056 (2011), the entire contents of which are incorporated by reference herein. Alkyne moieties (first reactive moiety 410) may serve as substrates for synthetically functionalizing the nanopore via Sonogashira coupling, e.g., using a reaction such as described in Li et al., "Copper-Free Sonogashira cross-coupling for functionalization of alkyne-encoded proteins in aqueous medium and in bacterial cells," J. Am. Chem. Soc. 133(39): 15316-15319 (2011), the entire contents of which are incorporated by reference herein. In still other examples, introduction of an alkene (first reactive moiety 410) via mutation to a non-canonical amino acid (e.g. homoallylglycine) allows for synthetic functionalization of the nanopore via chemical oxidation, Heck-type couplings, and a host of other chemistries (reactions between first reactive moiety 410 and second reactive moiety 420).

Installation of the desired cationic species can be accomplished through either a single-step process (e.g., such as described with reference to FIG. 4A-4B) or a multistep synthetic process (e.g., such as described with reference to FIG. 10). In some examples of the latter, the mutated site may first be transformed into one or more intermediate species—any of which may be reacted in subsequent steps to access a tethered cationic species, cationic complex, or a precursor thereof.

Note that the present compositions, devices, and methods need not be used with any particular chemistry for site-selective synthetic functionalization of the nanopore, e.g., any specific reactions between any particular first reactive moiety 410 and second reactive moiety 420. Indeed, it will be appreciated that any suitable chemistry may be used to synthetically functionalize polypeptide nanopore 20 with a positively charged species 30 (or precursor thereof) so as to provide a nanopore that inhibits translocation of cations 160 through the aperture of the nanopore and thus improves signal stability and mitigates electrolyte depletion.

Example Positively Charged Species

Various mutation strategies, as well as the various chemistries that can be performed on mutated residues to install the desired positively charged species or precursor thereof, are provided herein. It will be appreciated that the identity of this positively charged species or precursor thereof similarly may vary in size, composition, functionality, and reactivity. Below, a variety of example ionic groups or ionophores are described that may be used to provide a synthetically functionalized nanopore with charge characteristics suitable to inhibit translocation of cations 160 and permit translocation of anions 170.

Nonmetal Cations

In some examples, the positively charged species 30 may include a covalently linked nonmetal cation. These nonmetal cations are relatively common functionalities in organic chemistry, and they can be covalently bound to the mutated site on the protein in a manner such as described with reference to FIGS. 4A-4B and 10. Illustratively, such ions may include a non-metal heteroatom (e.g. nitrogen, sulfur, phosphorus, boron, etc.). The heteroatom may be substituted by any suitable number of R groups which confer a positive charge. Nonlimiting examples of such nonmetal cations are provided below:

(1)

Ammonium (2)

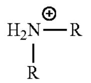

-continued (3)

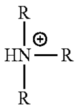

(4)

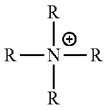

(5)

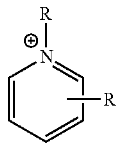

(6)

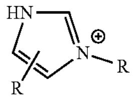

(7)

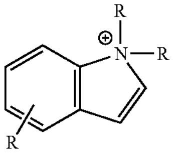

(8)

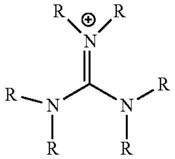

(9)

Sulfonium (10)

Phosphonium (11)

Boronium (12)

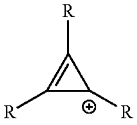

Cyclopropenium (13)

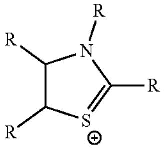

Thiazonium

-continued (14)

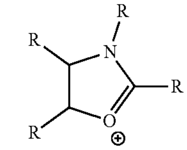

Oxazonium

Note that the R groups in the above structures may be the same or different. At least one of the R groups may be covalently bonded to the mutated residue—either directly through a single covalent bond or indirectly through a series of multiple covalent bonds.

A particular, nonlimiting example of a nonmetal cation that may be used as positively charged species 30 is the ammonium group (structures 1-8 above). The ammonium may be primary, secondary, or tertiary (respectively structure 1, 2, or 3 above). Here, the cationic character of the amine may be induced by the pH of the working buffer, which may protonate the amine to an ammonium ion (provided $pK_a$>pH). At least one of the R groups shown in structures 1-4 may be covalently linked to the mutated residue through one or more bonds, e.g., in a manner such as described with reference to FIGS. 4A-4B and 10. For the ammonium ions presented in structures 1-4 above, the R groups may include any covalent linkage of nonmetals, provided that at least one of them is covalently bound to the point mutation. Illustratively, one or more of the R groups may include a carbon-based functionality such as a saturated or unsaturated alkyl group or an aromatic species. Alternatively, or additionally, one or more of the R groups may include carbon and/or one or more heteroatom(s), such as oxygen, nitrogen, silicon, sulfur, boron, phosphorus that are capable of forming a covalent bond with the amine. For example, one or more of the R groups may include a combination of bound carbon, hydrogen, sulfur, and/or and one or more of the heteroatoms. Additionally, or alternatively, one or more of the R groups may include a thiol or may be derived from an ester, amide, amine, or carbonyl. Additionally, or alternatively, one or more of the R groups may include a heterocycle that may or may not be aromatic. Additionally, or alternatively, one or more of the R groups may include an oligo(siloxane) or oligo(ethylene oxide). Additionally, one or more of the R groups may include another amino acid, a nucleobase, a reactive handle for further bioconjugation, or photo- or redox-active label or dye.

Another particular, nonlimiting example of a nonmetal cation that may be used as positively charged species 30 is a nitrogenous aromatic and pi-conjugated species. These include (but are not limited to) pyridiniums, imidazolium, indoliums, and guanidiniums (as shown in structures 5-8 above), as well as carbazolium, quinoliniums, and functionalized derivatives of pyridinium and purinium nucleobases. For these species, the R groups may be either hydrogen or one of the functionalities described for amines, so long as at least one of the R groups is directly or indirectly bound to the point mutation in the nanopore 20.

Yet another particular, nonlimiting example of a nonmetal cation that may be used as positively charged species 30 is a substituted sulfonium, phosphonium, and/or boronium group (structures 9-11 above). For these species, the R groups may be either hydrogen or one of the functionalities described above, so long as at least one of the R groups is covalently tethered to the point mutation in the nanopore. In the case of the boronium ion depicted as structure 11, the boron atom may or may not have additional non-covalent ligands associated to it.

Another particular, nonlimiting example of a nonmetal cation that may be used as positively charged species 30 is an aromatic hydrocarbon, such as cyclopropenium (structure 12), or aromatic species containing multiple different heteroatoms, such as thiazoniums or oxazoniums (structures 13-14 above). Again, the R groups may be either hydrogen or one of the functionalities described above, so long as at least one of the R groups is linked to the mutated residue.

Note that for structures 5-14 above, the linkage to nanopore 20 may be through any suitable position in the structure so long as the overall substitution pattern on the heteroatom confers a net positive formal charge. This includes the use of zwitterions, which contain both cationic and anionic components, as long as the final net charge of the species is positive.

Additionally, the functionality introduced at the point mutation preferably does not disrupt the folding or assembly of the nanopore construct, and preferably does not interfere with the nanopore's ability to generate a signal based upon which nucleotides in a sequence respectively may be identified, illustratively based on the location of nucleotides or labels, and/or translocation of anions through the channel of the nanopore. Because MspA may be mutated to have cationic, anionic, or neutral species in its constriction site while still maintaining an appropriate channel structure, it is expected that the positively charged species 30 similarly will not detrimentally affect the nanopore channel, e.g., will not detrimentally impact the nanopore's ability to generate signal based on the locations of nucleotides or labels, and/or translocation of anions. In examples in which positively charged species 30 is coupled within or adjacent to the constriction 50 of the nanopore (e.g., in a manner such as illustrated in FIG. 3A), the final total size of positively charged species 30 may be selected so as to be smaller than the diameter of the nanopore at the site of the mutation so as to inhibit the positively charged species from sterically obstructing any elements besides the cations 160 from translocating through the construction that are needed to obtain a suitable signal. Illustratively, in the case of MspA, which is an octameric nanopore construct with a constriction site approximately 1.2 nm in diameter, it would be desirable for the overall size of the positively charged species 30 (including R groups) be no more than 1 nm in length and 0.5 nm in width. This size corresponds to approximately 10 linearly bound atoms in length and 5 linearly bound atoms in width, depending on how many of the octameric units are functionalized. In examples in which the positively charged species is coupled to other regions of the nanopore (e.g., below the constriction as illustrated in FIG. 1 or spaced apart from and above the constriction as illustrated in FIG. 3B), there may be less or no constraint on the size of the positively charged species.

Metal Coordination Complexes

In some examples, positively charged species 30 may include a cationic metal coordination complex. Such coordination complex may include at least one metal ion (M) complexed to one or more nonmetal ligands (L) in a manner such as shown schematically below:

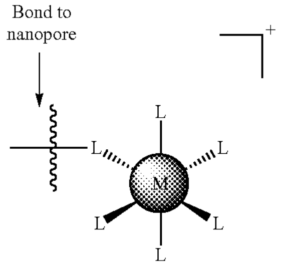

In some examples, the metal center M may include a transition metal or noble metal cation. Nonlimiting examples of metals that may be used in such a coordination complex include Ru, Pt, Os, Ni, Pd, Mn, Ir, Fe, Co, and Cu. The ligands L may form one or more bonds to the metal center, and these bonds may be covalent or non-covalent. The ligands independently may include a single element or a combination of elements, such as carbon, nitrogen, sulfur, oxygen, hydrogen, or a halide. The formal charge on each of ligands L may be negative, positive, or zero formal charge. If multiple ligands are bound to the metal center, the ligands may either be the same or different. These ligands may serve the purpose of (i) stabilizing the metal center through steric and electronic effects, (ii) modulating the formal charge on the overall coordination complex, and (iii) providing a functional group (second reactive moiety 420) for synthetically functionalizing the mutated residue of the nanopore. The ligands may be mono-, bi-, tri-, or poly-dentate. At least one of the ligands may be covalently bound to the point mutation so that the metal complex is tethered to the nanopore. The bond may be formed through any of the various chemistries described above.

In a manner such as described in greater detail elsewhere herein, the net charge on the overall coordination complex is positive, e.g., so as to electrostatically inhibit cations 160 from translocating through the nanopore. Nonlimiting examples of such coordination complexes include metal-macrocycle complexes, metals chelated by macrocycles, porphyrins, and the like. A nonlimiting example of a functional metal coordination complex with a ruthenium metal center is shown below, in which the metal center is decorated by polycyclic aromatic ligands.

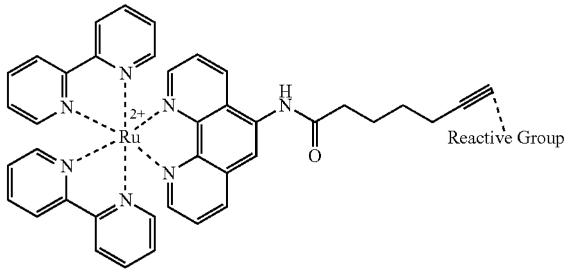

In this example, one of the ligands is functionalized with a reactive group, such as a terminal reactive alkyne group that can participate in azide-alkyne click chemistry in a manner similar to that described in the following references, the entire contents of each of which are incorporated by reference herein: Cheng et al., "Synthesis of a novel fluorescent ruthenium complex by an appended $Ac_4GlcNAc$ moiety by click reaction," Molecules, 23(7): 1649, 10 pages (2018); and Wang et al., "Single-molecule DNA detection using a novel SP1 protein nanopore," Chem. Commun., 49(17):1741-1743 (2013).

Ionophores

In some examples, positively charged species 30 may include an ionophore that binds to a cation 160 in electrolyte 24. In these examples, the nanopore is synthetically functionalized with a neutral or even negatively charged species in a manner such as described with reference to FIG. 10. The neutral or negatively charged species then binds to a cation 160 in the electrolyte 24, forming a complex that has an overall positive charge, that is, positively charged species 30. The cation may be bound to the ionophore through covalent or noncovalent interactions. The cation optionally may be divalent (e.g., calcium or magnesium)

The positively charged species formed using this approach is similar to that described above with regards to "Metal Coordination Complexes" because in both cases, the positive charge may be introduced by a metal ion bound by one or more nonmetal groups linked to the nanopore. However, the present approach differs in several ways. First, in the present approach, the nanopore is not initially functionalized with a positively charged species. Instead, the nanopore initially is synthetically functionalized with a precursor, such as an ionophore, that later binds to a cation that is present in the electrolyte. Furthermore, the ionophore may bind a Group I or Group II metal ion (e.g., $K^+$, $Na^+$, $Ca^{2+}$, or $Mg^{2+}$), which is found in the electrolyte, while the coordination complex may bind to other metals (e.g. transition metals or noble metals) that are not found in the electrolyte.

Nonlimiting examples of ionophores that may be conjugated to the nanopore to bind cations 160 include (macro) cyclic polyamines and polyethers that have a high affinity to electrolyte cations. Examples of these include crown ethers, cryptands, calixarenes, and valinomycin. Examples of suitable crown ethers include 15-crown-5, 18-crown-6, and 21-crown-7,

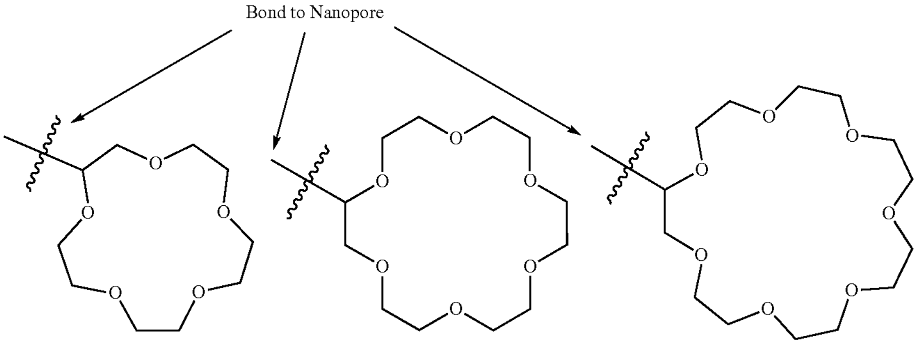

15-crown-5 18-crown-6 21-crown-7

Note that although example positions of the "bond to nanopore" are shown above, the bonds may be provided using any atom of the structure and not necessarily those which are illustrated. It is to be understood that derivatives of these crown ethers may also be used, such as benzo- or dibenzo-15-crown-5, benzo- or dibenzo-18-crown-6, benzo- or dibenzo-21-crown-7, dicyclohexano-18-crown-6, dicyclohexano-21-crown-7, or the like. Azacrowns (e.g., aza-15-crown-5) or thiacrowns may also be used. Examples of suitable calixarenes include and $C_3$Cal-5, $C_3$Cal-6, and calix[4]arene tetraesters. Valinomycin is shown below:

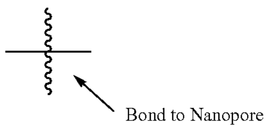

Nonlimiting examples of matching cations and cation complexing agents are shown in Table 2.

TABLE 2

| Cation | Cation Diameter | Crown Ethers (center cavity diameter) | Calixarenes | Valinomycin |
|---|---|---|---|---|
| $K^+$ | ~266 pm | 18-crown-6 (from about 260 pm to about 320 pm) | $C_3$Cal-5 $C_3$Cal-6 | Can complex both, but has greater selectively for $K^+$ over $Na^+$ |
| $Na^+$ | from about 194 pm to about 204 pm | 15-crown-5 (from about 170 pm to about 220 pm) | Calix[4]arene tetraesters | |

In one nonlimiting example, the cyclic polyether 18-crown-6 has a high binding affinity to potassium ions and is conjugated to a nanopore such as MspA through a functional point mutation in a manner such as described with reference to FIG. 10. The ionophore may bind a potassium ion in the electrolyte solution 24 and may electrostatically block the translocation of other cations 160 in the solution.

Although example ionophores are provided above, it will be appreciated that the ionophore may have any suitable structure. For example, the ionophore may be a discrete molecule, an oligomer, or polymer. Additionally, or alternatively, the ionophore may have a linear, branched, monocyclic, bicyclic, macrocyclic, or cage-like structure. The ionophore may bind to one or more metal cations, e.g., cation 160 in electrolyte 24. In various examples, the ionophore may be synthetically derived (e.g., crown ether) or naturally occurring (e.g., valinomycin, nystatin A, or monensin A).

Role of Counterions

For nanopores that are functionalized with a cationic species, such as the nonmetal cations and the metal coordination complexes, one or more anionic counterions may be present to stabilize the covalently bound cation. These anions may be monovalent or multivalent. The anions may not be covalently bound to the complex or to the nanopore, but instead may be electrostatically associated with the positively charged group 30, at least until the nanopore is immersed in a high dielectric media (e.g. the aqueous working electrolyte buffer 24) at which time the anions may dissociate and dissolve into the electrolyte. The anion(s) may include a single atom (e.g. $Cl^-$), a polyatomic complex (e.g. $PF_6^-$ or $BF_4^-$), or a combination thereof. Illustratively, the chloride anion may be readily hydrated in aqueous environments and commonplace in most biological buffers. In the case of the ionophores, the counterion already exists dissolved in the electrolyte.

Approaches to Control Nanopore Charge

The previous sections in this invention describe (i) the manner in which positively charged species can be synthetically installed into a nanopore through point mutations, and (ii) the variety of species that may be used to confer this desired positive charge. Next, various manners will be described in which the magnitude of the positive charge can be controlled.

Use of Multivalent Cations

In some examples, the magnitude of the positive charge added to the nanopore may be increased by synthetically functionalizing the mutated nanopore with a multivalent species. This may be achieved, for example, by installing a single species with a formal charge equal to or greater than +2, such as in a divalent rhodium complex described above with regards to "Metal Coordination Complexes". Alternatively, a single mutated site may be functionalized with a species that contains two or more separate monovalent species in the same covalently bound group of atoms. For example, the cationic species attached to the mutation may branch into two distinct segments, each terminated by a quaternary ammonium group (e.g., $NR_4^+$, structure 4 described above). In the case of MspA that has been mutated at a single site, use of a divalent species over a monovalent species would increase the overall added charge from +8 to +16 for the final octameric nanopore.

Multi-Site Mutation

Additionally, or alternatively, the magnitude of the positive charge added to the nanopore may be controlled by mutating in multiple different positions in the nanopore and functionalizing each with a positively charged species, e.g., in a manner such as described with reference to FIG. 3C. In one nonlimiting example, synthetically functionalizing two different locations of the nanopore with a given positively charged species may double the positive charge relative to synthetically functionalizing just one location of the nanopore with that positively charged species. In another nonlimiting example, synthetically functionalizing two different locations of a given subunit with a given positively charged species may double the positive charge relative to synthetically functionalizing just one location of that subunit with that positively charged species. Depending on the number of such subunits which are assembled to form the nanopore, the positive charge may be further multiplied in a manner such as will now be described.

Hybrid Nanopores

For nanopores that include multiple protein subunits, the final charge of the nanopore additionally or alternatively may be modulated by forming nanopores using a mixture of modified and unmodified protein subunits in any suitable ratio. The resulting collection of nanopores, on average, would have a net charge corresponding to the ratio of modified and unmodified protein subunits that were mixed together to form the nanopores. Each individual nanopore may have an integer-valued net charge corresponding to the particular number of modified and unmodified subunits that combined to form that nanopore. This technique provides a straightforward manner to tune the final electrostatic properties of the nanopore.

Figure 5A:
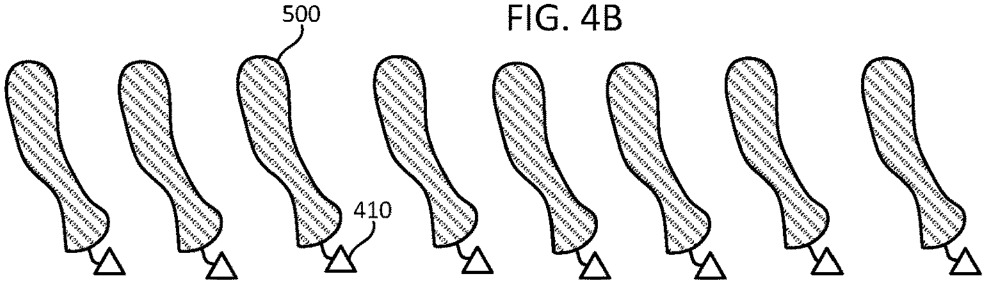
FIGS. 5A-5C schematically illustrate alternative operations in an example method for synthetically functionalizing a polypeptide nanopore with a positively charged species.
Figure 5B:
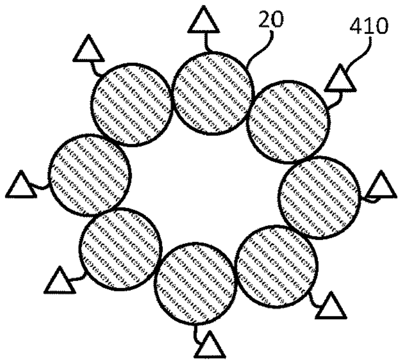
Figure 5C:
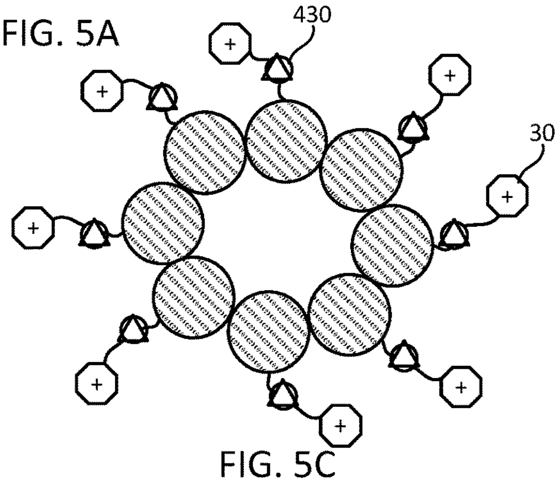

For example, FIGS. 5A-5C schematically illustrate alternative operations in an example method for synthetically functionalizing a polypeptide nanopore with a positively charged species. As illustrated in FIG. 5A, a plurality of protein subunits 500 are provided, each of which includes first reactive moiety 410. As illustrated in FIG. 5B (the view of which is rotated relative to that of FIG. 5A), a number of the subunits 500 assemble to form nanopore 20, depending on the particular type of nanopore being formed. The first reactive moieties 410 of the subunits respectively may be reacted with the second reactive moieties 420 of respective molecules 400 in a manner such as described with reference to FIGS. 4A-4B, yielding respectively reaction products 430 coupling a number of positively charged species 30 to nanopore 20 that is approximately equal to the number of subunits 500 in the nanopore in a manner such as illustrated in FIG. 5C. As an example, if every subunit of MspA (which is octameric) is mutated and functionalized with a monovalent species, combining these modified subunits yields a nanopore with an additional charge of +8.

Figure 6A:
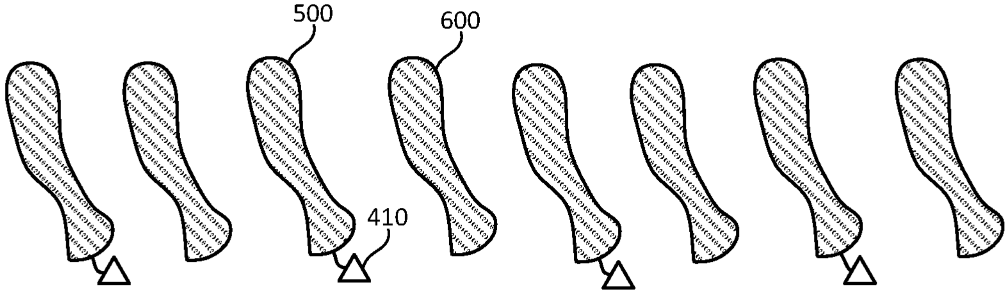
FIGS. 6A-6C schematically illustrate alternative operations in an example method for synthetically functionalizing a polypeptide nanopore with a positively charged species.
Figure 6B:
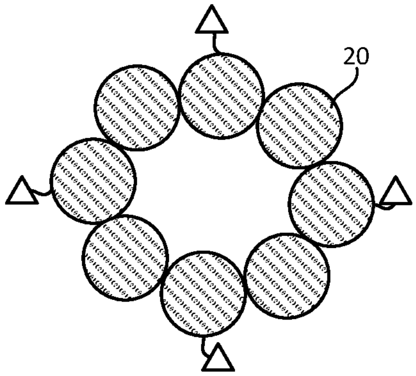
Figure 6C:
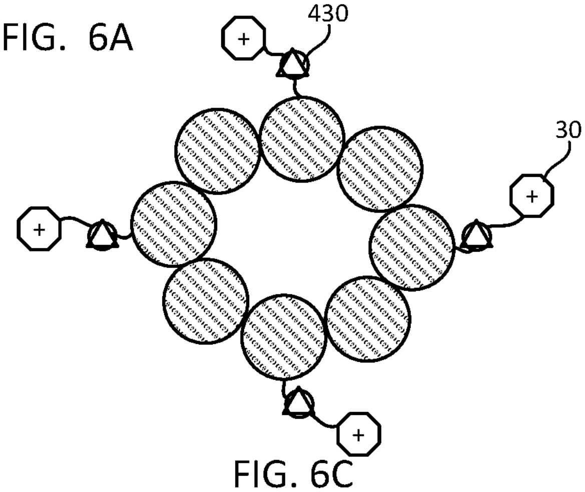

In comparison, mixing modified (charged) subunits with unmodified (uncharged) subunits may result in an average additional charge which is less than the number of subunits in the nanopore (in the case of monovalent species). For example, FIGS. 6A-6C schematically illustrate alternative operations in an example method for synthetically functionalizing a polypeptide nanopore with a positively charged species. As illustrated in FIG. 6A, a plurality of protein subunits 500 are provided, each of which includes first reactive moiety 410 in a manner such as described with reference to FIG. 5A. Additionally, a plurality of protein subunits 600 are provided which do not include the first reactive moiety 410. Protein subunits 500 and protein subunits 600 may be mixed together in any suitable ratio and may self-assemble into nanopores 20.

As illustrated in FIG. 6B (the view of which is rotated relative to that of FIG. 6A), a number of the subunits 500 and a number of the subunits 600 self-assemble to form nanopore 20, depending on the particular type of nanopore being formed. The first reactive moieties 410 of the subunits 500 respectively may be reacted with the second reactive moieties 420 of respective molecules 400 in a manner such as described with reference to FIGS. 4A-4B, yielding respectively reaction products 430 coupling a number of positively charged species 30 to nanopore 20 that is approximately equal to the number of subunits 500 in the nanopore in a manner such as illustrated in FIG. 6C. However, because subunits 600 lack reactive moiety 410, the overall charge added to nanopore 20 is lower than that described with reference to FIGS. 5A-5C.

Note that while a collection of nanopores 20 formed by mixing subunits 500 and 600 may, on average, have a net charge corresponding to the ratio of modified and unmodified protein subunits that were mixed together to form the nanopores, each individual nanopore may have numbers of modified and unmodified subunits that differ from the statistical average. As such, although the nonlimiting example illustrated in FIGS. 6A-6C may suggest that the modified subunits 500 regularly alternate with unmodified subunits 600 (corresponding to a 1:1 ratio of subunits 500 to subunits 600), it will be appreciated that any given nanopore 20 may have a ratio of subunits 500 to subunits 600 that differs from the statistical average, that is, that differs from the ratio of subunits 500 to subunits 600 that was initially mixed together. As such, any given nanopore 20 may have a charge which differs somewhat from the average charge of the collection of nanopores formed, e.g., that differs by about 1-40%, or by about 1-30%, or by about 1-20%, or by about 1-10%, from the average charge of the collection of nanopores formed. For example, for a 1:7 mixture for an octamer, the probability of exactly 1 and 7 assembly is about 0.4. Moreover, subunits 500 and subunits 600 within any given nanopore 20 may not necessarily be located at regular intervals as suggested in FIG. 6C, but instead may assemble with one another to form the nanopore in a manner that is dictated by the particular mixture of subunits which come into contact with one another while the nanopore is forming. Nonetheless, the collection of nanopores 20 resulting from assembly of subunits 500 and subunits 600 may have a well-characterized average charge based on the ratio of subunits 500 to subunits 600. Illustratively, mixing a 50/50 ratio of modified (charged) subunits 500 with unmodified (uncharged) subunits 600 would result in an average additional charge of +4 per nanopore, in the nonlimiting example in which each subunit 500 is associated with a monovalent cation.

Figure 7A:
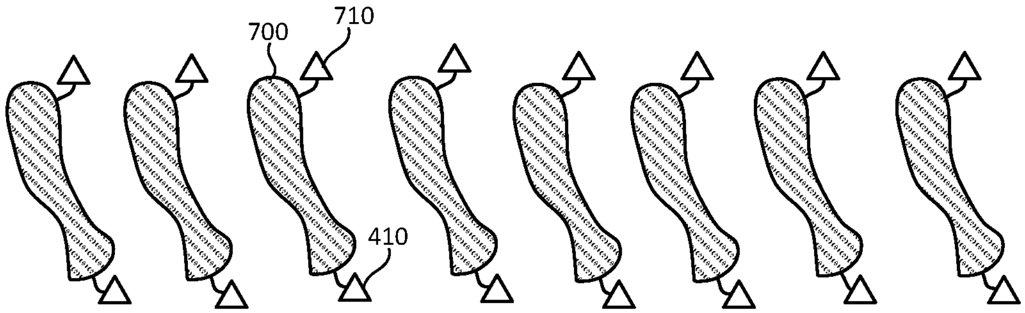
FIGS. 7A-7C schematically illustrate alternative operations in an example method for synthetically functionalizing a polypeptide nanopore with a positively charged species.
Figure 7B:
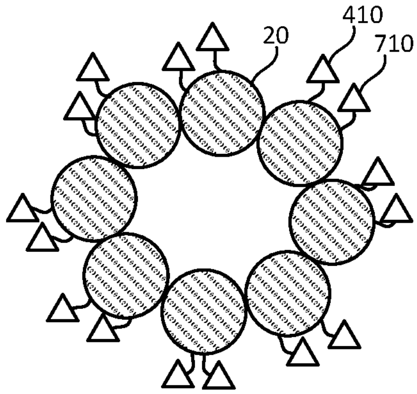
Figure 7C:
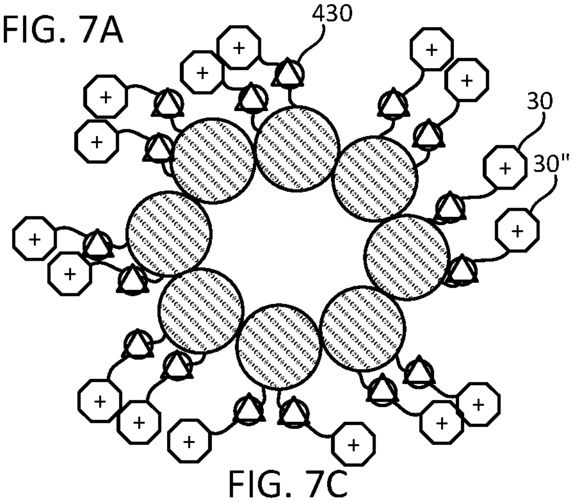

The number of positive charges coupled to a nanopore further may be adjusted in a manner such as described elsewhere herein, for example by using positively charged species 30 which include divalent cations, and/or by respectively coupling positively charged species to multiple mutation sites in a given subunit. For example, FIGS. 7A-7C schematically illustrate alternative operations in an example method for synthetically functionalizing a polypeptide nanopore with a positively charged species. As illustrated in FIG. 7A, a plurality of protein subunits 700 are provided, each of which includes reactive moiety 410 at a first location in the subunit and reactive moiety 710 at a second location in the subunit. In this example, reactive moieties 410 and 710 are of the same type as one another, although it will be appreciated that the moieties instead may be different than one another so that different chemistries may be used to independently couple elements (such as positively charged species) to reactive moieties 410 and 710. As illustrated in FIG. 7B (the view of which is rotated relative to that of FIG. 7A), a number of the subunits 700 assemble to form nanopore 20, depending on the particular type of nanopore being formed. The reactive moieties 410 and 710 of the subunits respectively may be reacted with the second reactive moieties 420 of respective molecules 400 in a manner such as described with reference to FIGS. 4A-4B, yielding respectively reaction products 430 coupling a number of positively charged species 30 to nanopore 20 that is approximately equal to two times the number of subunits 700 in the nanopore in a manner such as illustrated in FIG. 7C (species 30 and species 30" being illustrated in FIG. 7C to distinguish those which are coupled below the constriction from those which are coupled above the constriction in a manner such as described with reference to FIG. 3C). As an example, if every subunit of MspA (which is octameric) is mutated and functionalized with a monovalent species, combining these modified subunits yields a nanopore with an additional charge of +16, in the nonlimiting example in which positively charged species 30 is monovalent. Having options to add any suitable number of charges at any suitable locations within any suitable number of subunits of the nanopore allows the positive charge distribution to be tuned throughout the nanopore as may be appropriate for a particular application, e.g., particular electrolyte system 24 used within the nanopore sensing device.

Linked Protein Subunits

Figure 8A:
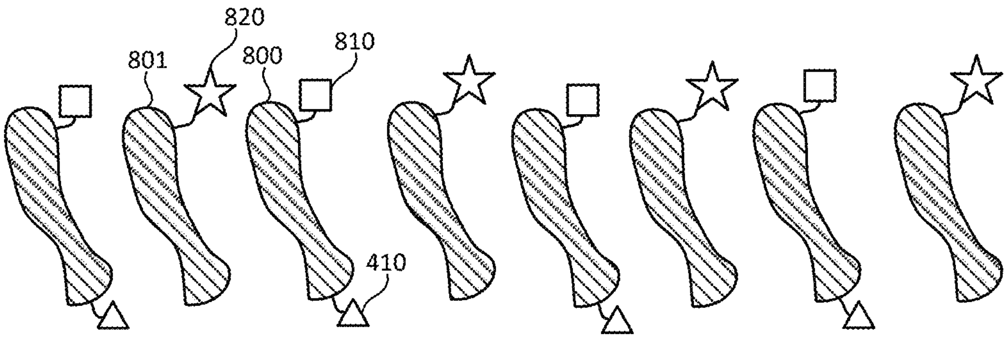
FIGS. 8A-8C schematically illustrate alternative operations in an example method for synthetically functionalizing a polypeptide nanopore with a positively charged species.
Figure 8B:
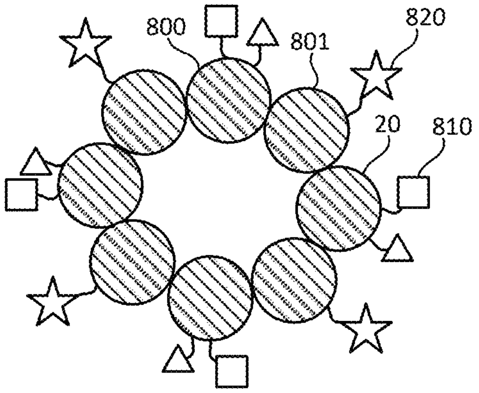
Figure 8C:
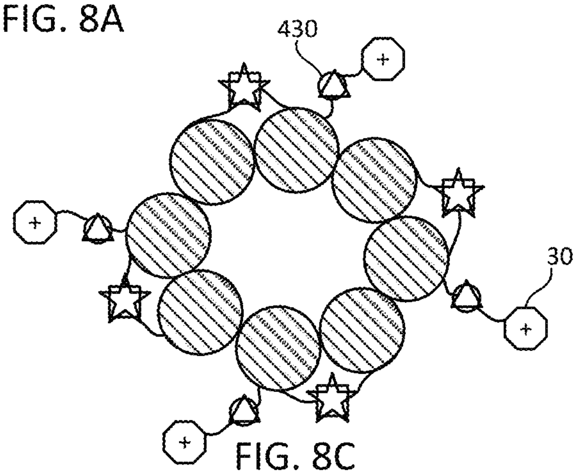

In some examples, neighboring or adjacent protein subunits may be synthetically functionalized with a positively charged species while also crosslinked with each other. For example, FIGS. 8A-8C schematically illustrate alternative operations in an example method for synthetically functionalizing a polypeptide nanopore with a positively charged species. As illustrated in FIG. 8A, a plurality of protein subunits 800 are provided, each of which includes reactive moiety 410 in a manner such as described with reference to FIG. 5A, as well as reactive moiety 810 coupled to a different location of the subunit 800. Additionally, a plurality of protein subunits 801 are provided which do not include the reactive moiety 410 or reactive moiety 810, but instead include reactive moiety 820 which is capable of becoming coupled to reactive moiety 810 after the nanopore is assembled (e.g., is coupled to the same or similar location of subunit 801 as is moiety 810 in subunit 800 and has a chemistry which can react directly or indirectly with moiety 810). Protein subunits 800 and protein subunits 801 may be mixed together in any suitable ratio and may self-assemble into nanopores 20.

As illustrated in FIG. 8B (the view of which is rotated relative to that of FIG. 8A), a number of the subunits 800 and a number of the subunits 801 self-assemble to form nanopore 20, depending on the particular type of nanopore being formed. The first reactive moieties 410 of the subunits 800 respectively may be reacted with the second reactive moieties 420 of respective molecules 400 in a manner such as described with reference to FIGS. 4A-4B, yielding respectively reaction products 430 coupling a number of positively charged species 30 to nanopore 20 that is approximately equal to the number of subunits 800 in the nanopore in a manner such as illustrated in FIG. 8C. However, because subunits 801 lack reactive moiety 410, the overall charge added to nanopore 20 is lower than that described with reference to FIGS. 5A-5C. Additionally, moieties 810 and 820 react with one another to cross-link subunits 800 to respective subunits 801. Such reaction may be direct, or may be indirect (e.g., may use a bifunctional molecule one portion of which couples to moiety 810 and another portion of which couples to moiety 820). In a similar manner as described with reference to FIGS. 6A-6C, the net charge of a collection of nanopores thus formed may correspond to the ratio of protein subunits 800 and 801 that were mixed together to form the nanopores, although each individual nanopore may have numbers such subunits that differ from the statistical average. Additionally, subunits 800 and subunits 801 within any given nanopore 20 may not necessarily be located at regular intervals as suggested in FIG. 8C, but instead may assemble with one another to form the nanopore in a manner that is dictated by the particular mixture of subunits which come into contact with one another while the nanopore is forming.

Figure 9A:
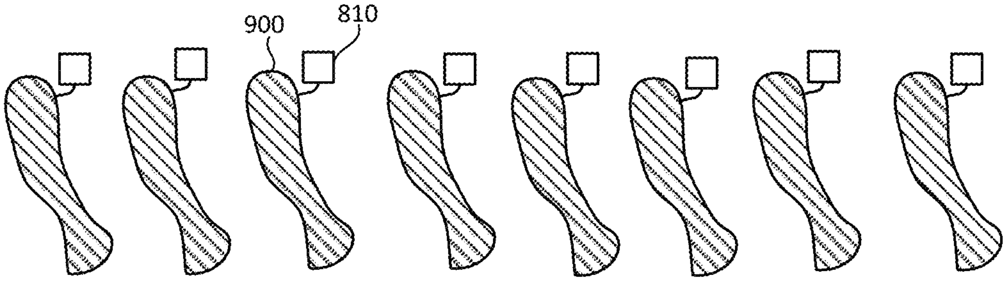
FIGS. 9A-9C schematically illustrate alternative operations in an example method for synthetically functionalizing a polypeptide nanopore with a positively charged species.
Figure 9B:
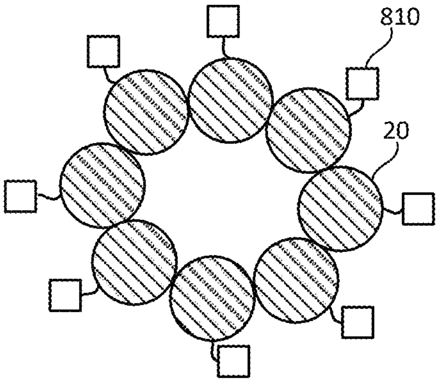
Figure 9C:
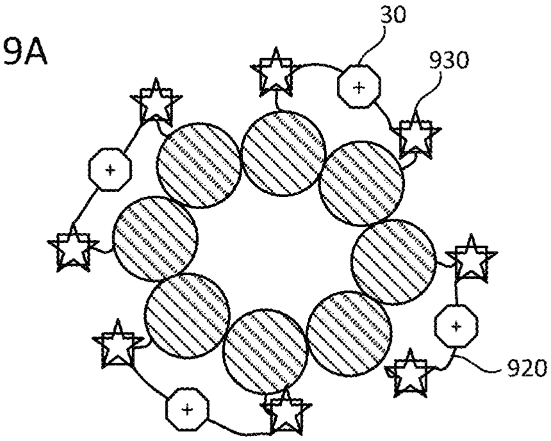

It will be appreciated that any suitable type of chemistr(ies) may be used to couple subunits of a nanopore to one another and/or to couple positively charged specie(s) to the nanopore. Such arrangements may further increase the stability of the nanopore complex and reduce noise. For example, FIGS. 9A-9C schematically illustrate alternative operations in an example method for synthetically functionalizing a polypeptide nanopore with a positively charged species. As illustrated in FIG. 9A, a plurality of protein subunits 900 are provided, each of which includes reactive moiety 910 in a manner such as described with reference to FIG. 9A. Reactive moieties 810 are capable of becoming coupled to one another after the nanopore is assembled (e.g., are coupled to the same or similar locations of subunits 800 as one another and have a chemistry which can react directly or indirectly with one another). Optionally, subunits 900 may include the reactive moiety 410, and as such may not be coupled to molecules 400 via reaction with reactive moiety 420 in a manner such as described with reference to FIGS. 5A-5C. Instead, in this option, subunits 900 may be coupled to one another using molecules which include positively charged species. Additionally, or alternatively, subunits 900 optionally may additionally include any suitable reactive moieties (e.g., 410 and/or 710, not specifically illustrated in FIGS. 9A-9C) via which positively charged species may be coupled to the subunits in a manner such as described elsewhere herein.

As illustrated in FIG. 9B (the view of which is rotated relative to that of FIG. 9A), a number of the subunits 900 9 self-assemble to form nanopore 20, depending on the particular type of nanopore being formed. As illustrated in FIG. 9C, moieties 810 may be used to cross-link subunits 900 to one another. Such reaction may be direct, or may be indirect via molecules 920, e.g., bifunctional molecules including two moieties 930, one of which couples to one moiety 810 and the other of which couples to another moiety 810). In the illustrated option, molecules 920 further include positively charged species 30. Accordingly, reaction of moieties 930 with moieties 810 both couples the positively charged species 30 to nanopore 20 and cross-links subunits in the nanopore. In the illustrated example, nanopore 20 is coupled to approximately half the number of molecules 920 (and thus to approximately half the number of positively charged species) as the number of subunits 900 in the nanopore.

In one nonlimiting example, molecules 920 are or include telechelic cross-linking agent that (i) can form covalent bonds at each end with neighboring or adjacent subunits, and (ii) maintains a net positive charge after reacting with the subunits. One example cross-linking agent for this would be dipropargyl amine, which includes a secondary amine flanked by two terminal alkynes. This cross-linking agent may undergo a "click" cycloaddition reaction with azide-based mutations (e.g., azidohomoalanine) to join two protein subunits together. The amine in dipropargyl amine would be mostly protonated at pH=7.5 and therefore would simultaneously confer positive charge to the nanopore.

It will be appreciated that any of the approaches described with reference to FIGS. 5A-5C, 6A-6C, 7A-7C, 8A-8C, and 9A-9C may be combined to tune the ion selective properties of the nanopore, enhance signal fidelity and stability, and mitigate the electrolyte depletion issue. Any of such approaches further may be combined with any of the approaches described with reference to FIGS. 1, 2, 3A-3C, 4A-4B, and 10.

Figure 11:
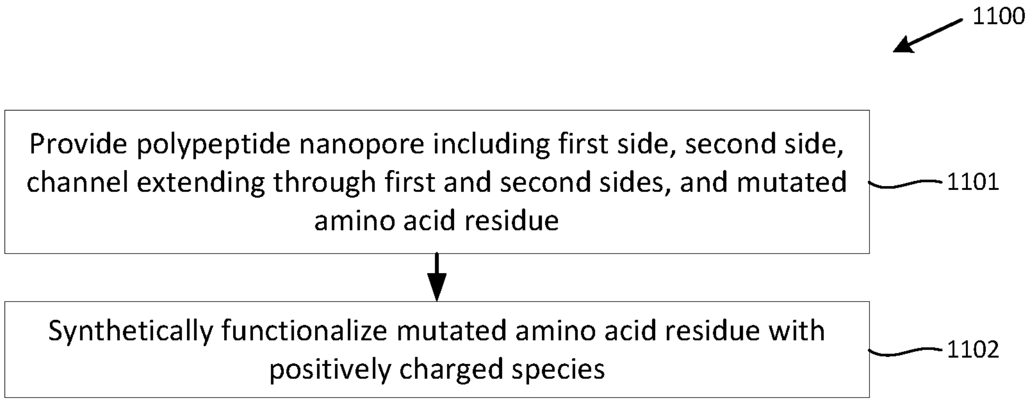
FIG. 11 illustrates a flow of operations in an example method of making a nanopore.

For example, FIG. 11 illustrates a flow of operations in an example method 1100 of making a nanopore. Method 1100 may include providing a polypeptide nanopore including a first side, a second side, a channel extending through the first and second sides, and a mutated amino acid residue (operation 1101). For example, in a manner such as described with reference to FIGS. 2 and 3A-3C, any suitable number of residues in the nanopore may be mutated in such a manner as to include a reactive moiety. Optionally, in a manner such as described with reference to FIG. 5A-5C, 6A-6C, 7A-7C, 8A-8C, or 9A-9C, providing the polypeptide nanopore may include providing a plurality of polypeptide nanopore subunits, at least one of which includes the mutated amino acid residue. The subunits that self-assemble to form the nanopore may have the same mutation as one another, and/or may have different mutation(s) than one another, and/or some of the subunits may not necessarily have any mutations. The subunits optionally may be crosslinked, e.g., in a manner such as described with reference to FIGS. 8A-8C and 9A-9C, and such crosslinking optionally may be via the positively charged species, e.g., in a manner such as described with reference to FIGS. 9A-9C.

Method 1100 also may include synthetically functionalizing the mutated amino acid residue with a positively charged species (operation 1102). Nonlimiting examples of first reactive moieties that may be included in the mutated amino acid residue, and of second reactive moieties that may be reacted with the first reactive moieties to synthetically functionalize the mutated amino acid residue are described with reference to FIGS. 4A-4B and 10. Nonlimiting examples of positively charged species that may be coupled to the mutated amino acid residue via the products of such reactions are described further above.

It will be appreciated that any of the approaches provided herein suitably may be adapted for use with different redox couples used in nanopore sequencing. For example, in an Ag/AgCl system, nanopore 20 or nanopore 20' may be used to restrict the translocation of electrolyte cations (e.g., $K^+$, $Na^+$, and the like), while permitting the translocation of the redox-active anion ($Cl^-$). These nanopores may be used with other electrochemical systems in which the anion is the redox-active ion, such as the ferri/ferrocyanide redox system. In such example, nanopore 20 or nanopore 20' may permit the translocation of both redox-active anion complexes (ferricyanide and ferrocyanide) while inhibiting translocation of electrolyte cations (e.g., $K^+$). In any such system, by permitting anion translocation while inhibiting cation translocation, the present nanopores 20, 20' may mitigate electrolyte depletion and accordingly promote a more stable signal and prolong the device lifetime.

Figure 12:
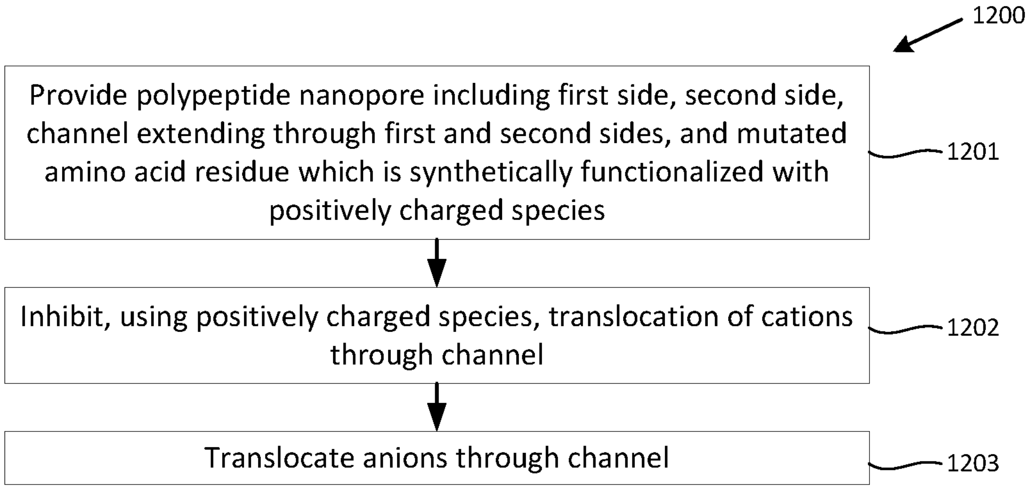
FIG. 12 illustrates a flow of operations in an example method of using a nanopore.

Devices and Methods Using Modified Nanopores 20, 20' for Nanopore Sequencing It will further be appreciated that the present nanopores 20, 20' may be used in any suitable device or application. For example, FIG. 12 illustrates a flow of operations in an example method 1200 of using a nanopore. Method 1200 includes providing a polypeptide nanopore including a first side, a second side, a channel extending through the first and second sides, and a mutated amino acid residue which is synthetically functionalized with a positively charged species (operation 1201). Details, options, and nonlimiting examples of such a nanopore, and methods of providing the same, are described with reference to FIGS. 1-11. Method 1200 includes inhibiting, using the positively charged species, translocation of cations through the channel (operation 1202). For example, in a manner such as described elsewhere herein, the positively charged species 30 may electrostatically repel cations from entering and/or translocating through channel 13 of the nanopore. Method 1200 includes translocating anions through the channel (operation 1203). For example, positively charged species 30 may not inhibit anions from translocating through channel 13 of the nanopore.

Figure 13:
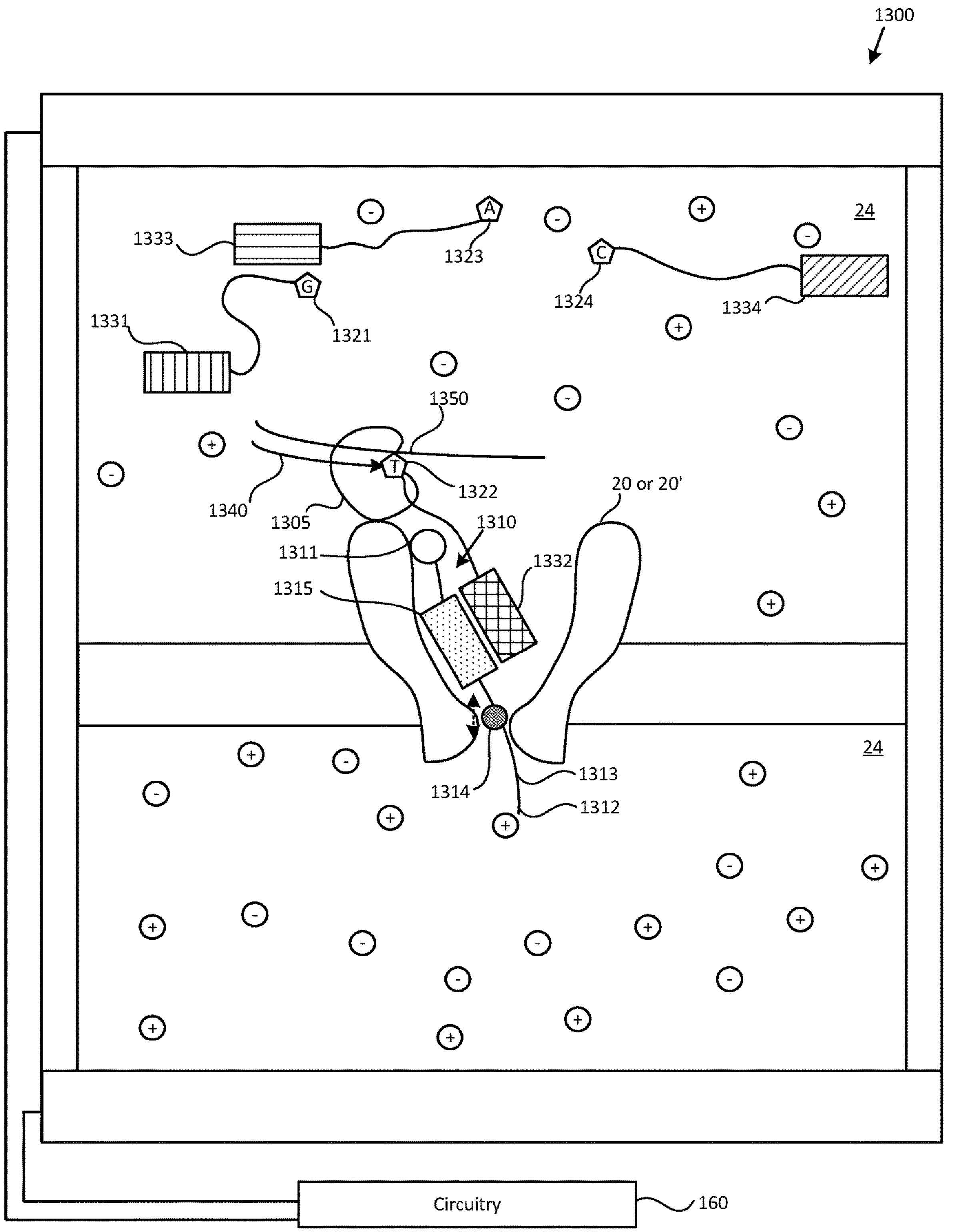
FIG. 13 schematically illustrates a cross-sectional view of an example use of the composition and device of FIG. 1.

Nanopores 20 and modified nanopores 20' are compatible with a wide variety of nanopore sequencing methods. FIG. 13 schematically illustrates a cross-sectional view of an example use of the composition and device of FIG. 1. Device 1300 illustrated in FIG. 13 may be configured similarly as device 10 described with reference to FIG. 1, and may include nanopore 20 or 20' in a manner such as described with reference to FIGS. 1-11. In the nonlimiting example illustrated in FIG. 13, electrolyte 24 in the cis well optionally may include a plurality of each of nucleotides 1321, 1322, 1323, 1324, e.g., G, T, A, and C, respectively. Each of the nucleotides 1321, 1322, 1323, 1324 in second fluid 120' optionally may be coupled to a respective label 1331, 1332, 1333, 1334 coupled to the nucleotide via an elongated body (elongated body not specifically labeled). Optionally, device 1300 further may include polymerase 1305. As illustrated in FIG. 13, polymerase 1305 may be in the cis well. Optionally, polymerase 1305 may be coupled to nanopore 20, 20' or to barrier 1301, e.g., via a suitable elongated body (not specifically illustrated). Device 1300 optionally further may include first and second polynucleotides 1340, 1350 in a manner such as illustrated in FIG. 13. Polymerase 1305 may be for sequentially adding nucleotides of the plurality to the first polynucleotide 1340 using a sequence of the second polynucleotide 1350. For example, at the particular time illustrated in FIG. 13, polymerase 1305 incorporates nucleotide 1322 (T) into first polynucleotide 1340, which is hybridized to second polynucleotide 1350 to form a duplex. At other times (not specifically illustrated), polymerase 1305 sequentially may incorporate other of nucleotides 1321, 1322, 1323, 1324 into first polynucleotide 1340 using the sequence of second polynucleotide 1350.

Circuitry 160 illustrated in FIG. 13 may be configured to detect changes in an electrical characteristic of the aperture responsive to the polymerase sequentially adding nucleotides of the plurality to the first polynucleotide 1340 using a sequence of the second polynucleotide 1350. In the nonlimiting example illustrated in FIG. 13, nanopore 20, 20' may be coupled to permanent tether 1310 which may include head region 1311, tail region 1312, elongated body 1313, reporter region 1314 (e.g., an abasic nucleotide), and moiety 1315. Head region 1311 of tether 1310 is coupled to nanopore 1310 via any suitable chemical bond, protein-protein interaction, or any other suitable attachment that is normally irreversible. Head region 1311 can be attached to any suitable portion of nanopore 1310 that places reporter region 1314 within aperture 13 and places moiety 1315 sufficiently close to polymerase 1305 so as to interact with respective labels 1331, 1332, 1333, 1334 of nucleotides 1321, 1322, 1323, 1324 that are acted upon by polymerase 1305. Moiety 1315 respectively may interact with labels 1331, 1332, 1333, 1334 in such a manner as to move reporter region 1314 within aperture 13 and thus alter the rate at which ions in electrolyte 24 move through aperture 13, and thus may detectably alter the electrical conductivity of aperture 13 in such a manner as to be detected by circuitry 160. For further details regarding use of permanent tethers coupled to nanopores to sequence polynucleotides, see U.S. Pat. No. 13,708,655, the entire contents of which are incorporated by reference herein. In a manner such as described elsewhere herein, nanopore 20 may be synthetically functionalized to include positively charged species 30, or modified nanopore 20' may include positively charged residue(s), which inhibit the translocation of cations through the aperture of the nanopore.

Figure 14:
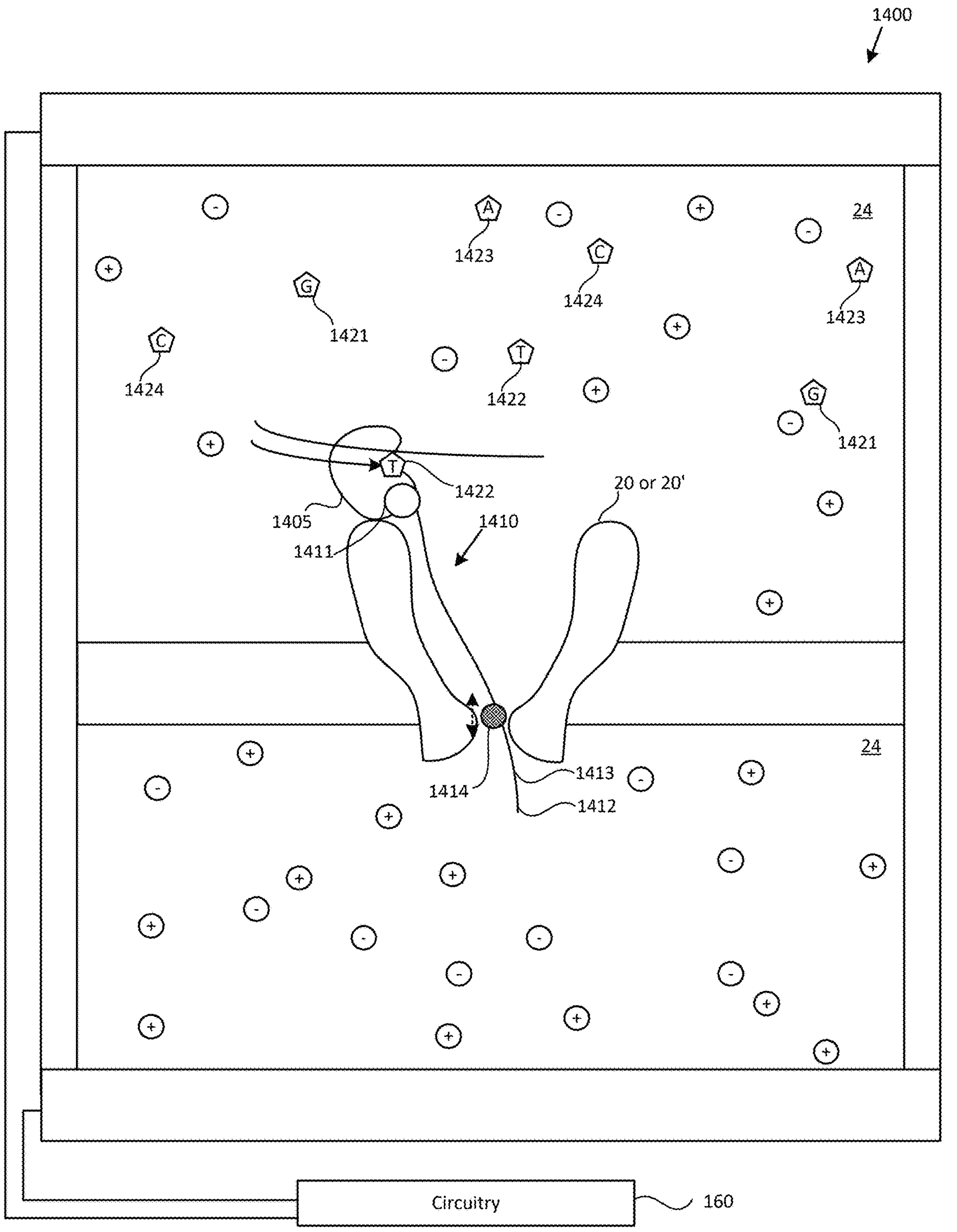
FIG. 14 schematically illustrates a cross-sectional view of another example use of the composition and device of FIG. 1.

FIG. 14 schematically illustrates a cross-sectional view of another example use of the composition and device of FIG. 1. Device 1400 illustrated in FIG. 14 may be configured similarly as device 1300 described with reference to FIG. 13. However, in the nonlimiting example illustrated in FIG. 14, nucleotides 1421, 1422, 1423, 1424 in electrolyte 24 in the cis well need not necessarily be coupled to respective labels. Polymerase 1405 may be coupled to nanopore 20, 20' and may be coupled to permanent tether 1410 which may include head region 1411, tail region 1412, elongated body 1413, and reporter region 1414 (e.g., an abasic nucleotide). Head region 1411 of tether 1410 is coupled to polymerase 1405 via any suitable chemical bond, protein-protein interaction, or any other suitable attachment that is normally irreversible. Head region 1411 can be attached to any suitable portion of polymerase 1405 that places reporter region 1414 within aperture 13. As polymerase 1405 interacts with nucleotides 1421, 1422, 1423, 1424, such interactions may cause polymerase 1405 to undergo conformational changes. Such conformational changes may move reporter region 1414 within aperture 13 and thus alter the rate at which ions in electrolyte 24 move through aperture 13, and thus may detectably alter the electrical conductivity of aperture 13 in such a manner as to be detected by circuitry 1460. For further details regarding use of permanent tethers coupled to polymerases to sequence polynucleotides, see U.S. Pat. No. 9,708,655, the entire contents of which are incorporated by reference herein. In a manner such as described elsewhere herein, nanopore 20 may be synthetically functionalized to include positively charged species 30, or modified nanopore 20' may include positively charged residue(s), which inhibit the translocation of cations through the aperture of the nanopore.

Figure 15:
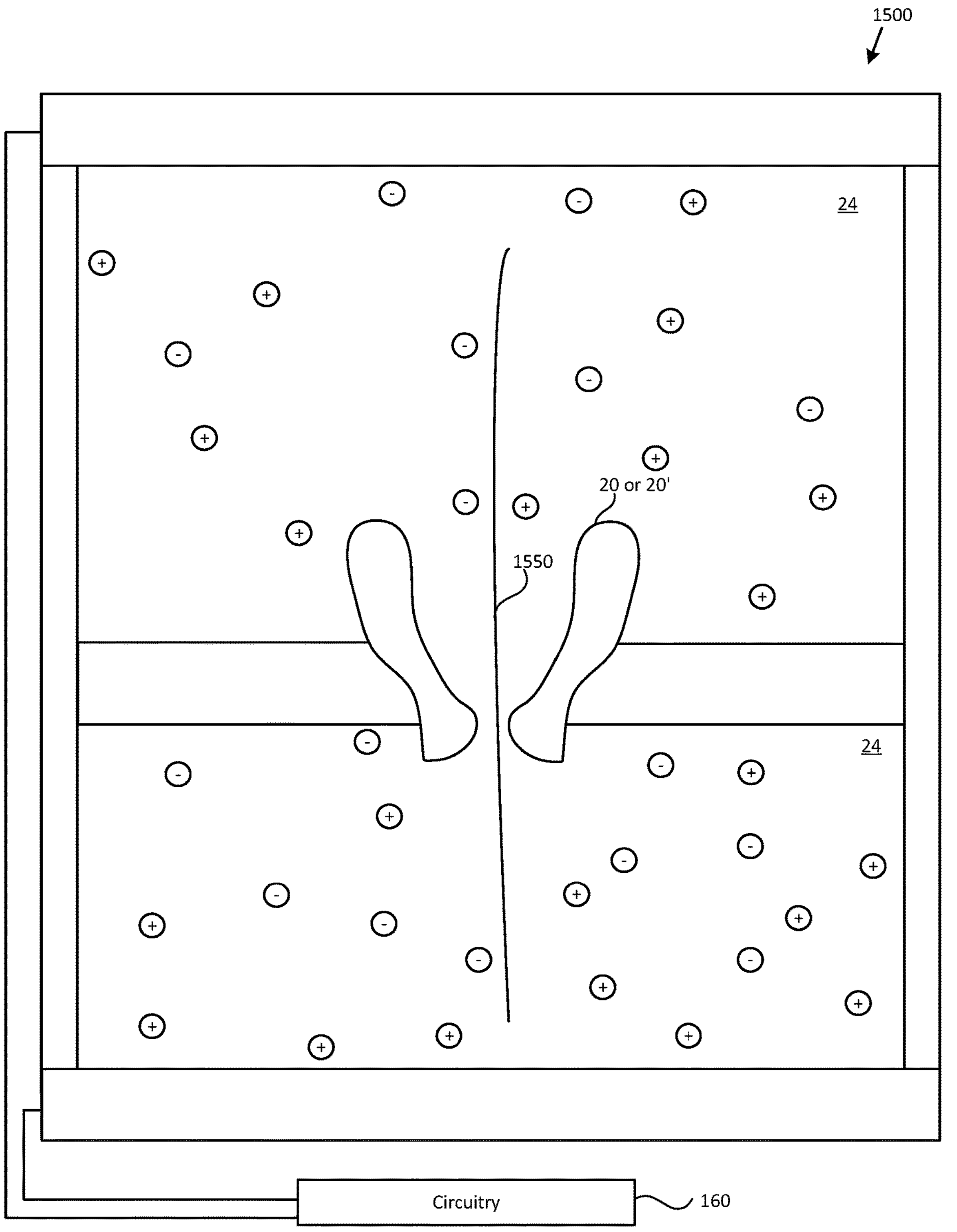
FIG. 15 schematically illustrates a cross-sectional view of another example use of the composition and device of FIG. 1.

FIG. 15 schematically illustrates a cross-sectional view of another example use of the composition and device of FIG. 1. Device 1500 illustrated in FIG. 15 may be configured similarly as device 1300 described with reference to FIG. 13. However, in the nonlimiting example illustrated in FIG. 15, polynucleotide 1550 is translocated through nanopore 20, 20' under an applied force, e.g., a bias voltage that circuitry 160 applies between the cis and trans electrodes. As bases in polynucleotide 1550 pass through nanopore 20, 20', such bases may alter the rate at which ions in electrolyte 24 move through aperture 13, and thus may detectably alter the electrical conductivity of aperture 13 in such a manner as to be detected by circuitry 160. For further details regarding use of nanopores to sequence polynucleotides being translocated therethrough, see U.S. Pat. No. 5,795,782, the entire contents of which are incorporated by reference herein. In a manner such as described elsewhere herein, nanopore 20 may be synthetically functionalized to include positively charged species 30, or nanopore 20' may include positively charged residue(s), which inhibit the translocation of cations through the aperture of the nanopore.

Figure 16:
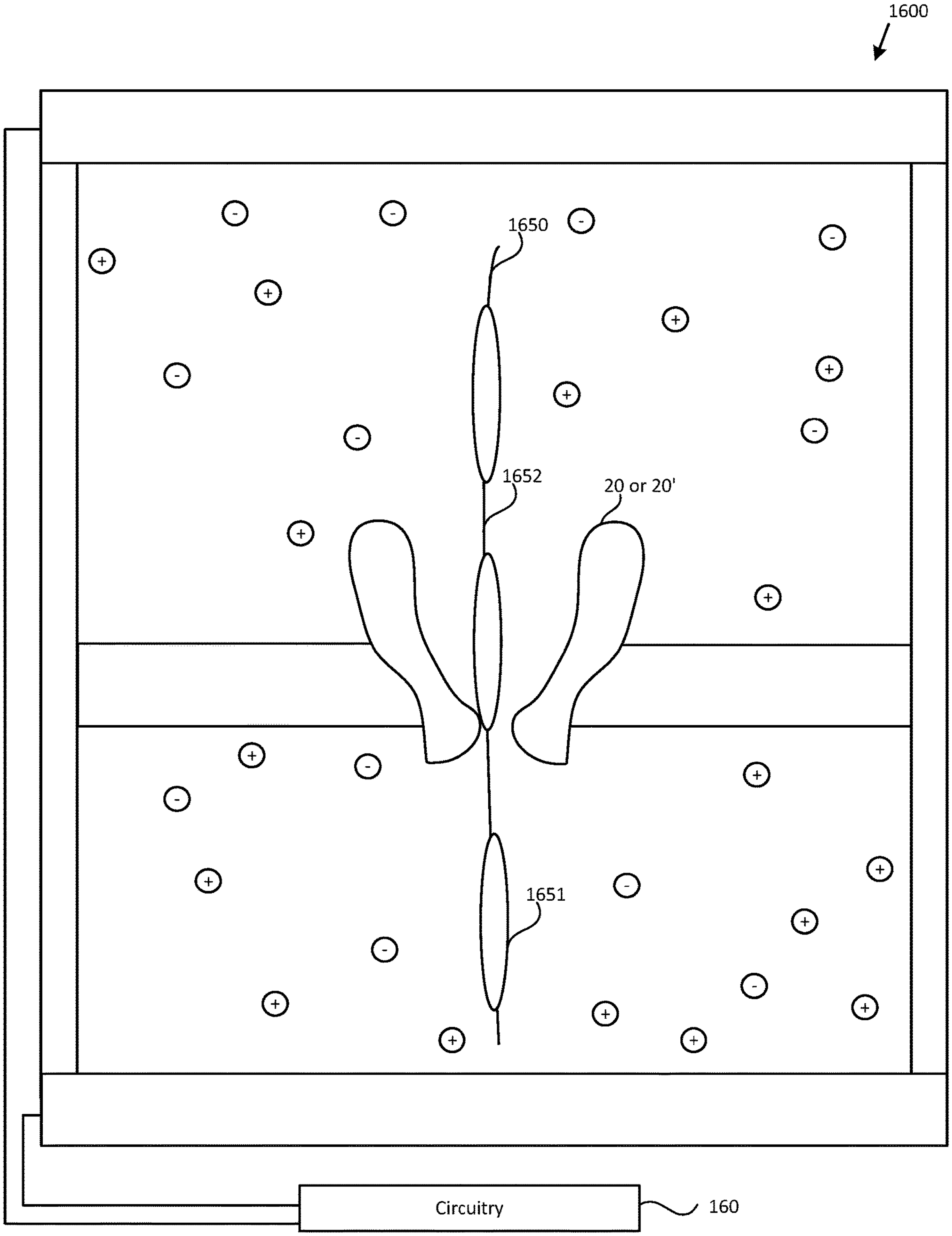
FIG. 16 schematically illustrates a cross-sectional view of another example use of the composition and device of FIG. 1.

FIG. 16 schematically illustrates a cross-sectional view of another example use of the composition and device of FIG. 1. Device 1600 illustrated in FIG. 16 may be configured similarly as device 1300 described with reference to FIG. 13. In the nonlimiting example illustrated in FIG. 16, surrogate polymer 1650 is translocated through nanopore 20, 20' under an applied force, e.g., a bias voltage that circuitry 160 applies between the cis and trans electrodes. As used herein, a "surrogate polymer" is intended to mean an elongated chain of labels 1651 having a sequence corresponding to a sequence of nucleotides in a polynucleotide. An XPANDOMER™ is a particular type of surrogate polymer developed by Roche Sequencing, Inc. (Pleasanton, CA). XPANDOMERS™ may be prepared using Sequencing By eXpansion™ (SBX™, Roche Sequencing, Pleasanton CA). In Sequencing by eXpansion™, an engineered polymerase polymerizes xNTPs which include nucleobases coupled to labels via linkers 1652, using the sequence of a target polynucleotide. The polymerized nucleotides are then processed to generate an elongated chain of the labels 1651, separated from one another by linkers 1652 which are coupled between the nucleotides, and having a sequence that is complementary to that of the target polynucleotide. As labels 1651 in surrogate polymer 1650 pass through nanopore 20, 20', such labels may alter the rate at which ions in electrolyte 24 move through aperture 13, and thus may detectably alter the electrical conductivity of aperture 13 in such a manner as to be detected by circuitry 160. For example descriptions of XPANDOMERS™, linkers (tethers), labels, engineered polymerases, and methods for SBX™, see the following patents, the entire contents of each of which are incorporated by reference herein: U.S. Pat. Nos. 7,939,249, 8,324,360, 8,349,565, 8,586,301, 8,592,182, 9,670,526, 9,771,614, 9,920,386, 10,301,345, 10,457,979, 10,676,782, 10,745,685, 10,774,105, and 10,851,405. In a manner such as described elsewhere herein, nanopore 20 may be synthetically functionalized to include positively charged species 30, or nanopore 20' may include positively charged residue(s), which inhibit the translocation of cations through the aperture of the nanopore.

To further illustrate the present disclosure, an example is given herein. It is to be understood that this example is provided for illustrative purposes and is not to be construed as limiting the scope of the present disclosure.

NON-LIMITING WORKING EXAMPLES

The following examples are intended to be purely illustrative, and not limiting of the present invention.

Example 1

Figure 17:
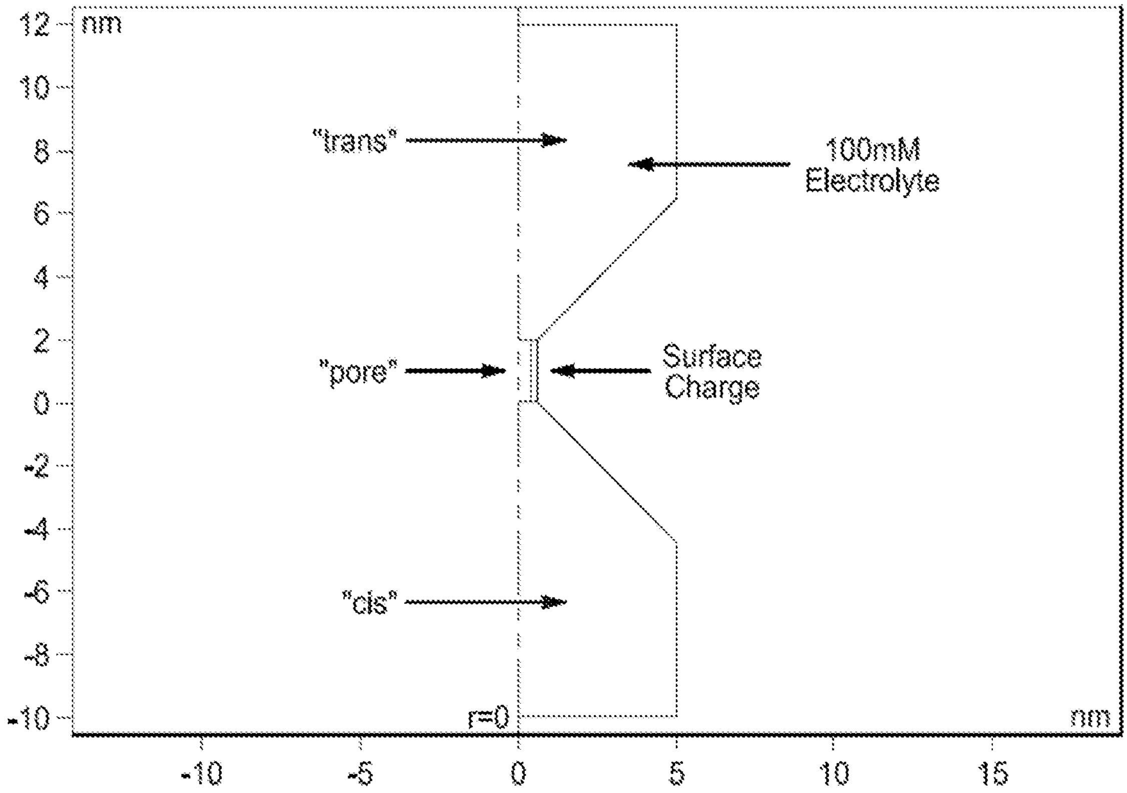
FIG. 17 is an illustration of the COSMOL simulation domain used in Example 1.

To assess whether the ultra-narrow but ultra-short channels of biological nanopores can exclude cations at desired levels, 3D finite element analysis was performed on the geometry, as shown in FIG. 17. The full structure is rotationally symmetric, and thus only half the simulation domain in shown in FIG. 17.

In this analysis, the nanopore was 1 nm wide and 2 nm tall, which approximates the dimensions of the MspA constriction. A fixed surface charge in varying amounts was placed on the surface of the constriction. The "cis" and "trans" wells were placed under boundary conditions that simulated an infinite source of $K^+$ and $Cl^-$ in order to eliminate depletion effects from the simulations.

The simulations were performed for surface charge densities (a) in the range of 0.01 q/$nm^2$ to 1 q/$nm^2$, where q is the elementary charge. This is the net charge that would be present in an idealized "dry" state in the absence of electrolytes. Such charge densities should, in principle, be achievable in protein nanopores.

Figure 18A:
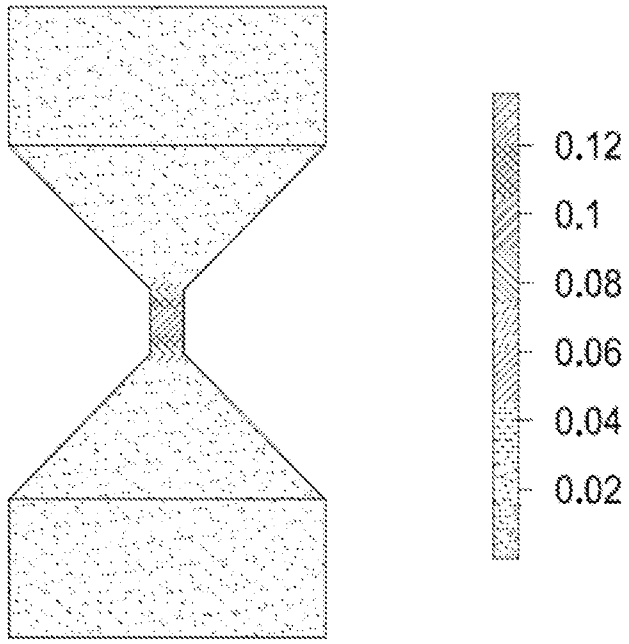
FIGS. 18A-18C depict the 3D finite element analysis results, showing the computed spatial distribution (log scale) of the Cl:K ratio in the simulation domain.
Figure 18B:
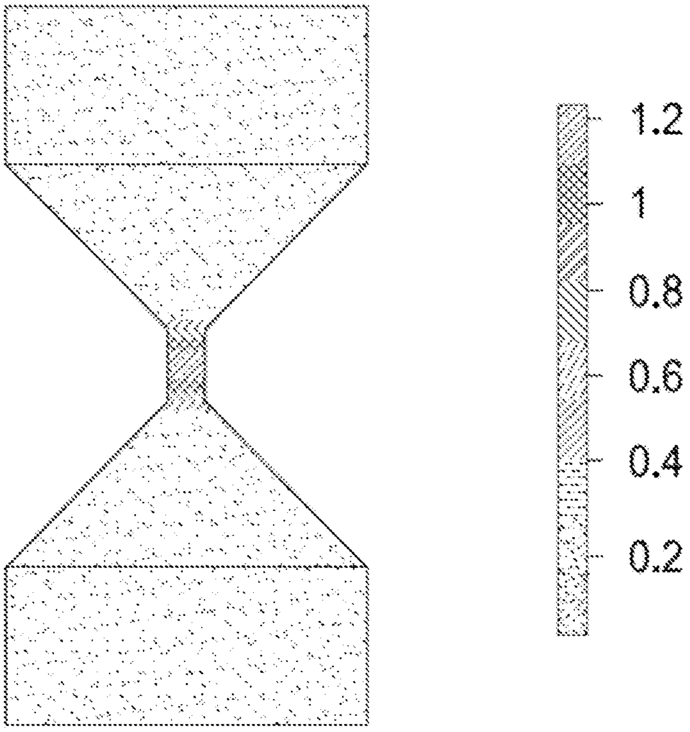
Figure 18C:
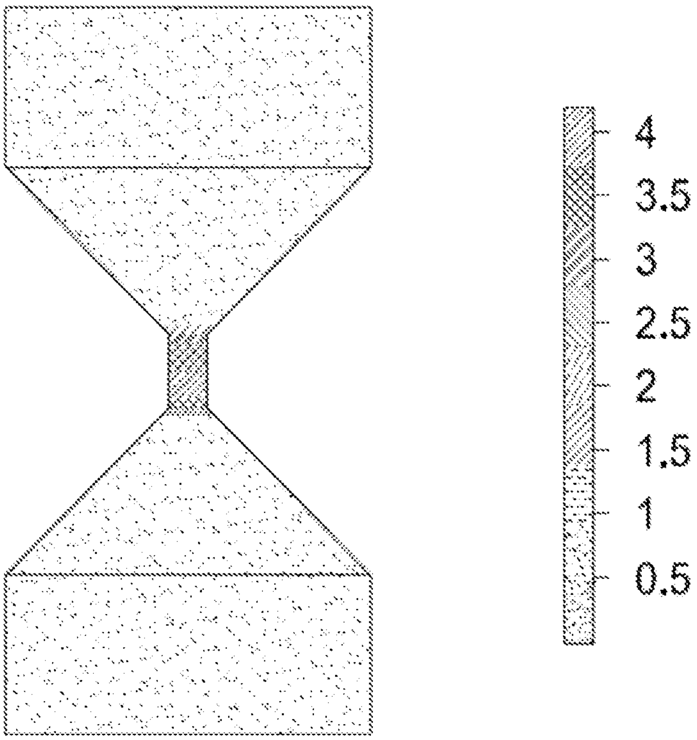
Figure 19:
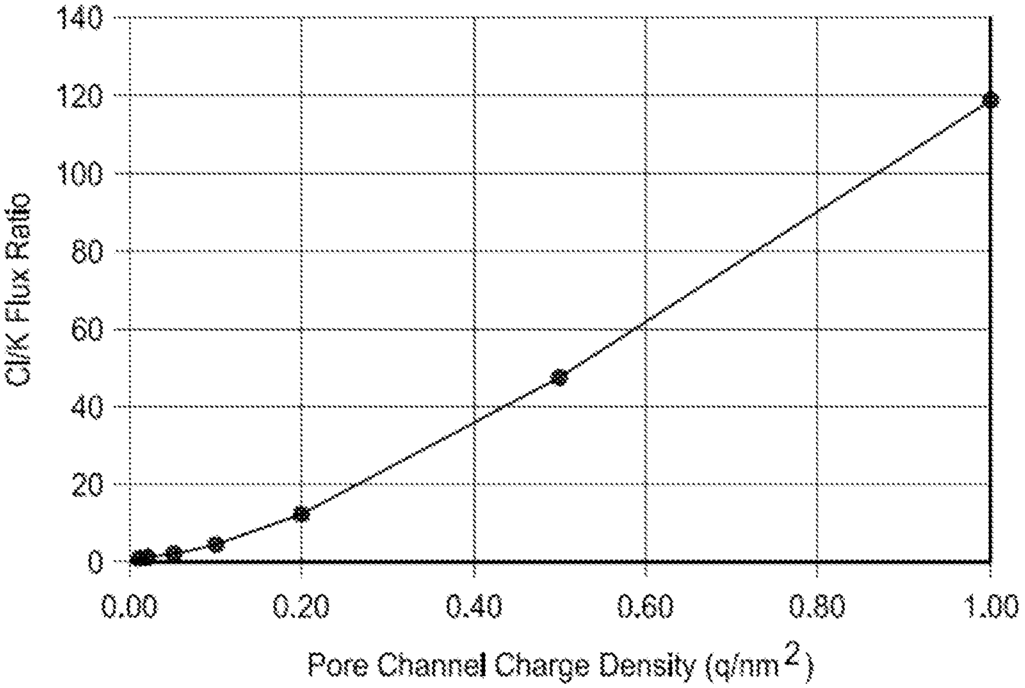
FIG. 19 is a graph depicting the computed dependence of the Cl:K flux ratio through the nanopore on the magnitude of the fixed charge density in the nanopore channel.

The results of the simulation are shown in FIGS. 18A, 18B, and 18C, respectively, for $\sigma$=0.01 q/$nm^2$, $\sigma$=0.1 q/$nm^2$, and $\sigma$=1 q/$nm^2$. More specifically, FIGS. 18A-18C illustrate the computed spatial distribution (log scale) of the Cl:K ratio in the simulation domain. The data in FIGS. 17A-17C is plotted on a log scale and a scale marker accompanies each image. While the Cl:K ratio peaks in the nanochannel for all three conditions, the magnitude of the effect is exponentially dependent on the charge density. This is more clearly visible in FIG. 19. FIG. 19 is the computed dependence of the Cl:K flux ratio through the nanopore on the magnitude of the fixed charge density in the nanopore channel.

Figure 20A:
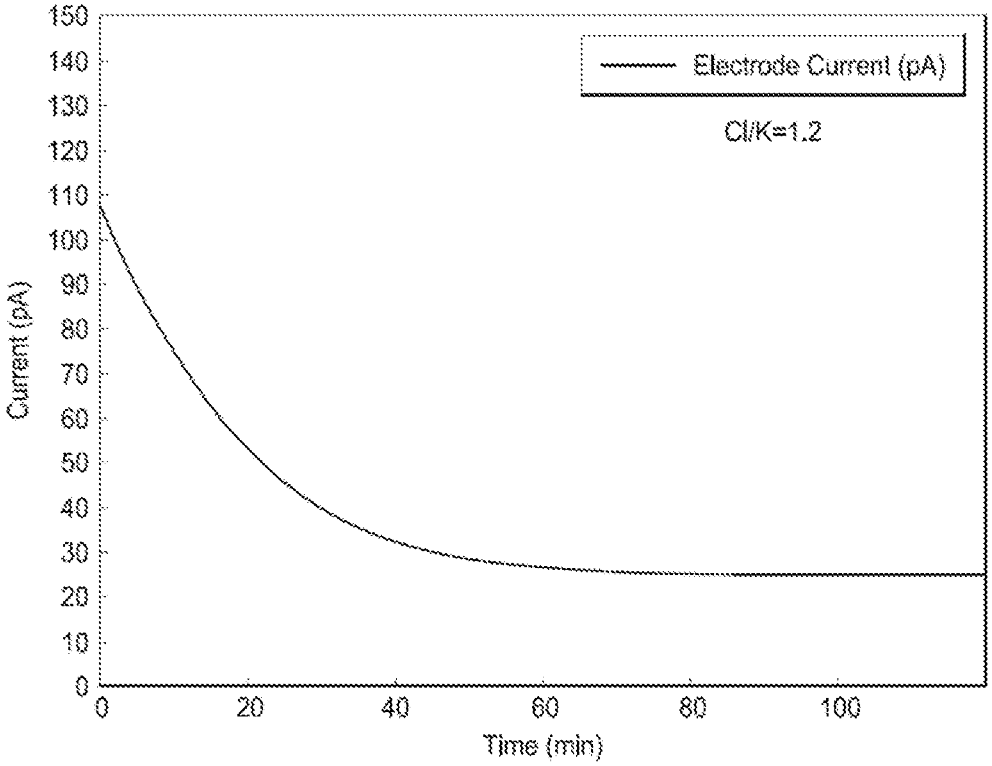
FIGS. 20A-20C are graphs depicting the computed dependence of a nanopore sensor with a modified nanopore at various Cl:K flux ratios.
Figure 20B:
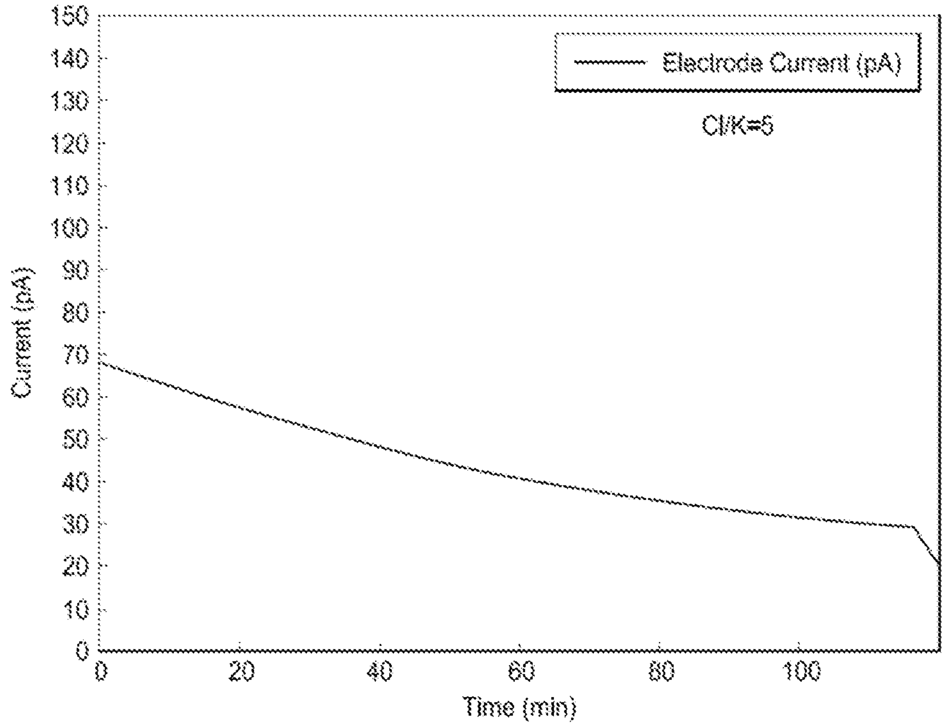
Figure 20C:
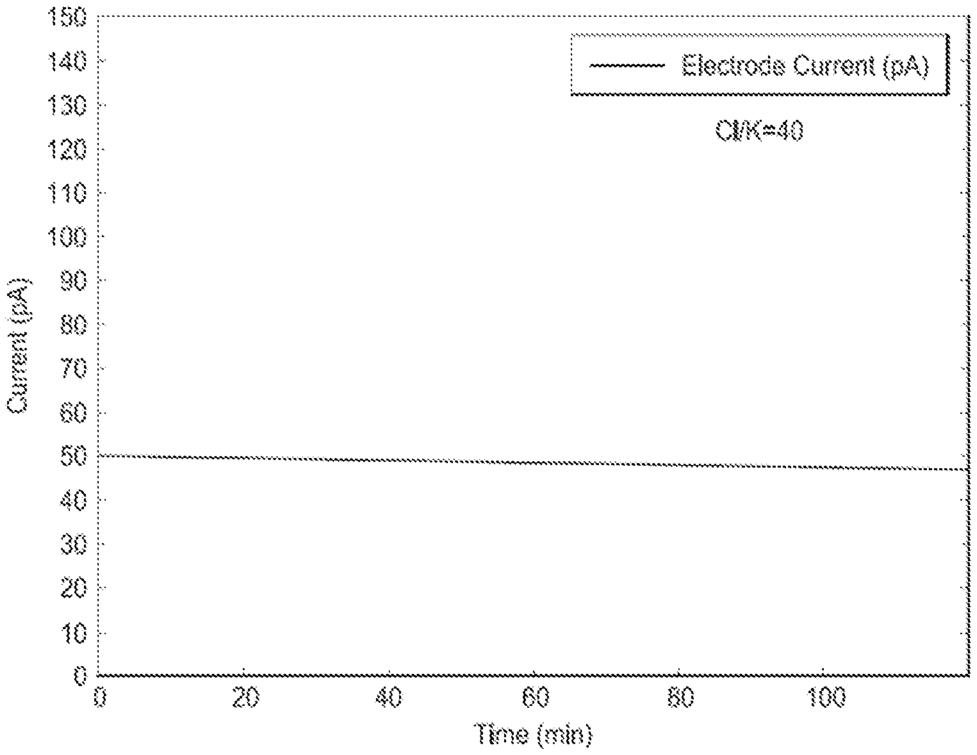

In order to characterize the beneficial effect of suppressing the total $K^+$ flux through the nanopore, additional simulations were performed. More specifically, the behavior of a nanopore sensor with the same $K^+Cl^-$ concentration in the cis and trans wells was computed. The time and species dependence of the nanopore current was obtained by numerically solving the Nernst-Planck equation in a commercial software package (COMSOL Multiphysics™, Comsol, Inc., Burlington, Mass.). The calculation was performed for a nanopore sensor with a cis well having a diameter of 200 μm and a height of 200 μm, a trans well having a diameter of 20 μm and a height of 20 μm, a $K^+Cl^-$ concentration of 100 mM in each of the well, and a cis-trans voltage bias of about 100 mV. Three different values of the Cl:K flux ratio were simulated:R=1.2 ($\sigma$=0.01 q/$nm^2$); R=5 ($\sigma$=0.1 q/$nm^2$); and R=40 ($\sigma$=0.4 q/$nm^2$). The results are shown in in FIG. 20A, FIG. 20B, and FIG. 20C, respectively. From these results, the beneficial effect of suppressing $K^+$ transport through the nanopore is clear. At R=40 ($\sigma$=0.4 q/$nm^2$) the depletion effects were nearly completely suppressed. The current drift was significantly reduced, which facilitates practical use of the nanopore sensor.

Example 2

In this example, four different types of modified MspA pores were compared. The comparative MspA pores included neutral asparagine residues at D90, D91, and D93. The first example MspA pores included neutral asparagine residues at D90 and D93 and a positively charged arginine residue at D91. The second example MspA pores included neutral asparagine residues at D91 and D93 and a positively charged arginine residue at D90. The third example MspA pores included a neutral asparagine residue at D93 and positively charged arginine residues at D90 and D91. All of the pores were tested using wells that were 5 μm deep and 16 μm wide. The data presented in this example represents the average results for ten or more of the respective pores (e.g., 19 comparative MspA pores were tested at 150 mM, 58 first example MspA pores were tested at 150 mM, 21 comparative MspA pores were tested at 300 mM, and 10 first example MspA pores were tested at 300 mM).

Figure 21B:
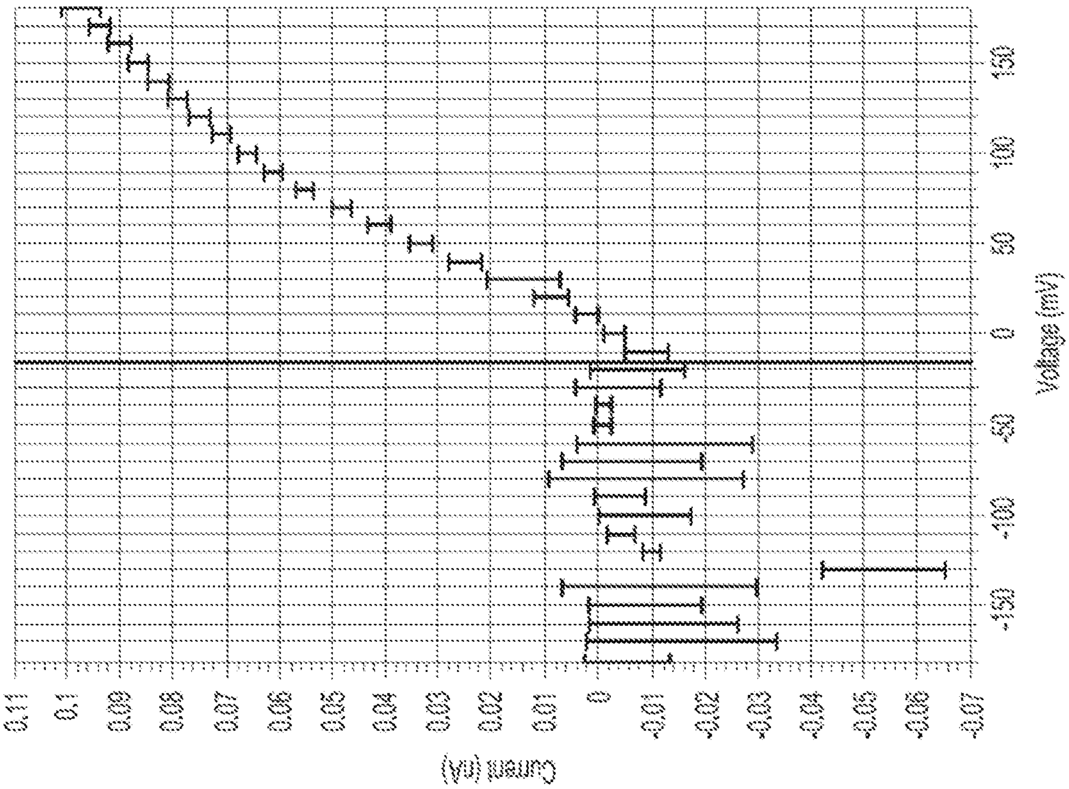
FIG. 21B is a graph depicting the current (nA, Y axis) versus voltage (mV, X axis) for first example MspA pores.
Figure 21A:
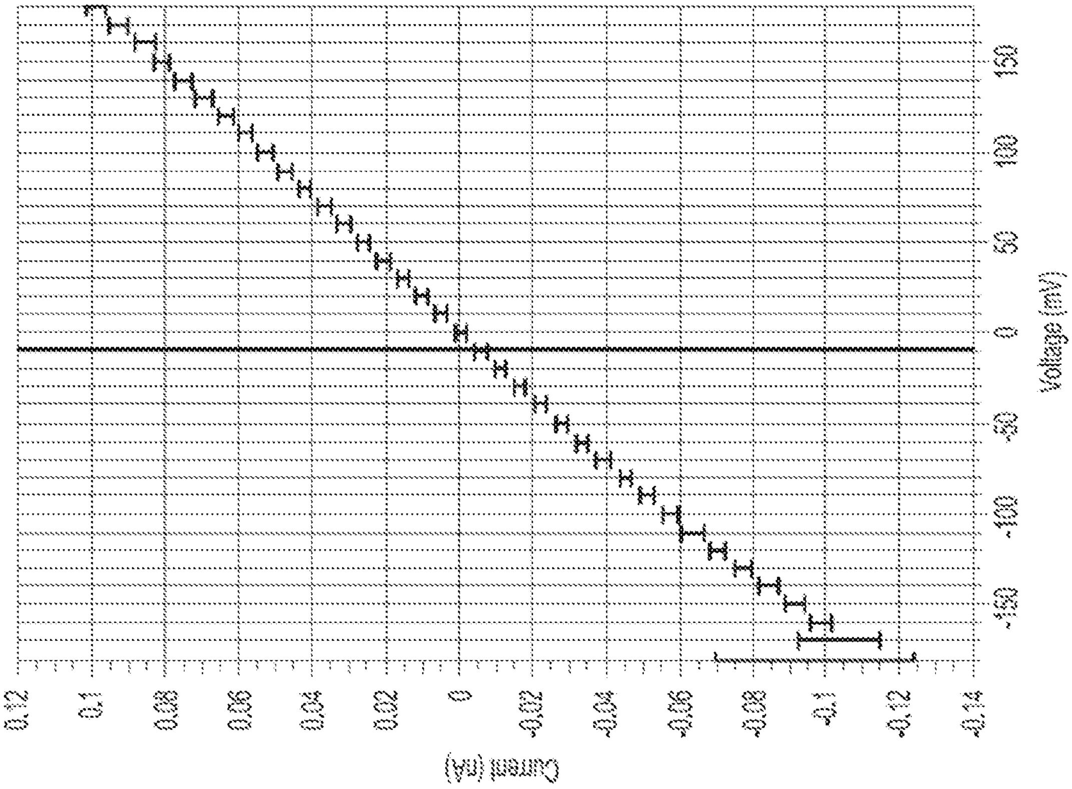
FIG. 21A is a graph depicting the current (nA, Y axis) versus voltage (mV, X axis) for comparative MspA pores.

In the first experiment, the K+Cl− concentration in the cis and trans wells was 300 mM. The cis-trans voltage bias was swept from −175 mV to 175 mV and the current (nA) was recorded. FIG. 21A depicts the current (nA, Y axis) versus voltage (mV, X axis) for the comparative MspA pores and FIG. 21B depicts the current versus voltage graph for the first example MspA pores. While the data for the second and third example MspA pores is not reproduced herein, all of the pores (comparative and example MspA pores), exhibited higher resistance at higher positive potentials. The first and second example MspA pores (each having two neutral residues) exhibited an expected rectification of current at the negative bias (see FIG. 21B for the results of the first example MspA pores). The third example MspA pores (having two positive residues) exhibited almost no conductivity until large positive potentials were used.

Figure 22:
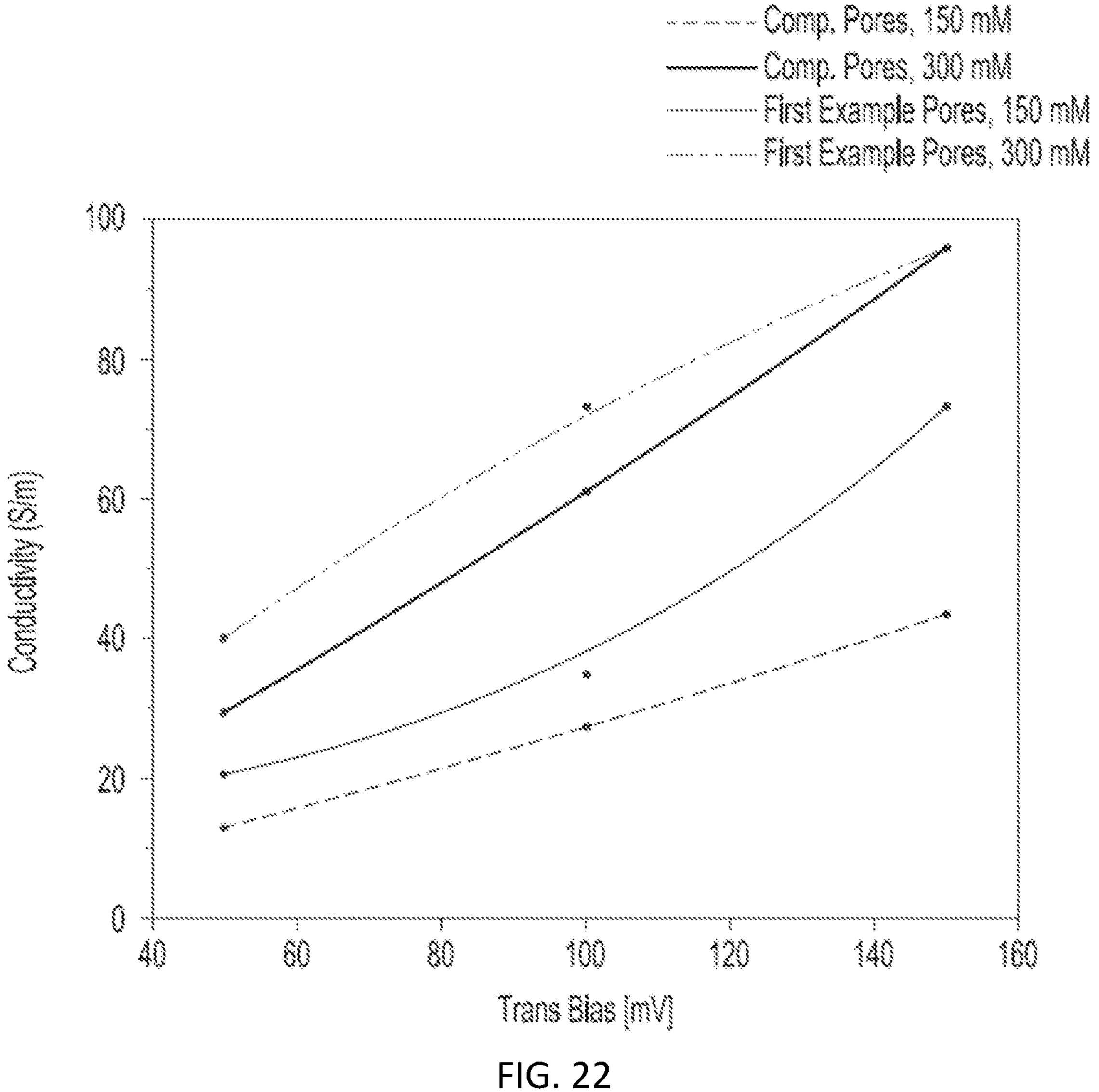
FIG. 22 is a graph depicting the average conductivity (S/m, Y axis) of the first example pores and of the comparative pores versus the cis-trans voltage bias (mV, X axis) using different concentrations of a KCl electrolyte.

In the second experiment, the comparative MspA pores and the first example MspA pores were tested with different K+Cl− concentrations, namely 150 mM and 300 mM. The bias voltage was swept from 50 mV to 150 mV and the current (pA) was recorded. FIG. 22 plots the average current (pA, Y axis) of the first example pores and of the comparative pores versus the cis-trans voltage bias (mV, X axis) in the different electrolytes. Clearly, the first example MspA pores had higher conductivity than the comparative MspA pores, regardless of the electrolyte concentration.

Figure 23A:
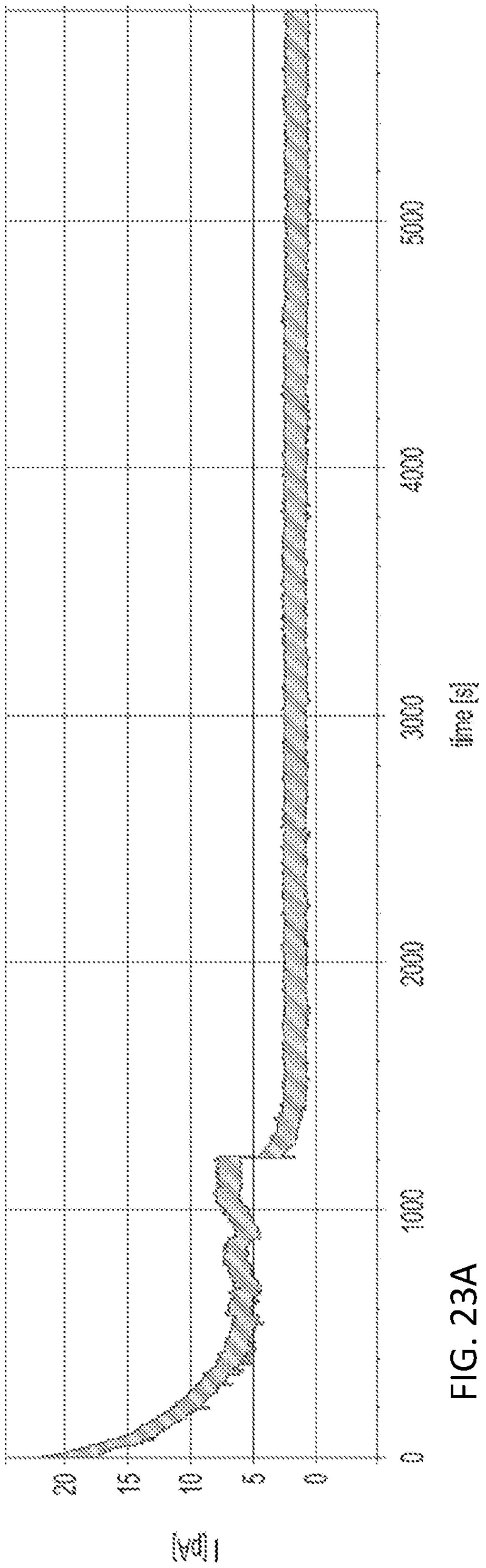
FIG. 23A is a graph depicting the current (pA, Y axis) versus time (s, X axis) for the comparative MspA pores.
Figure 23B:
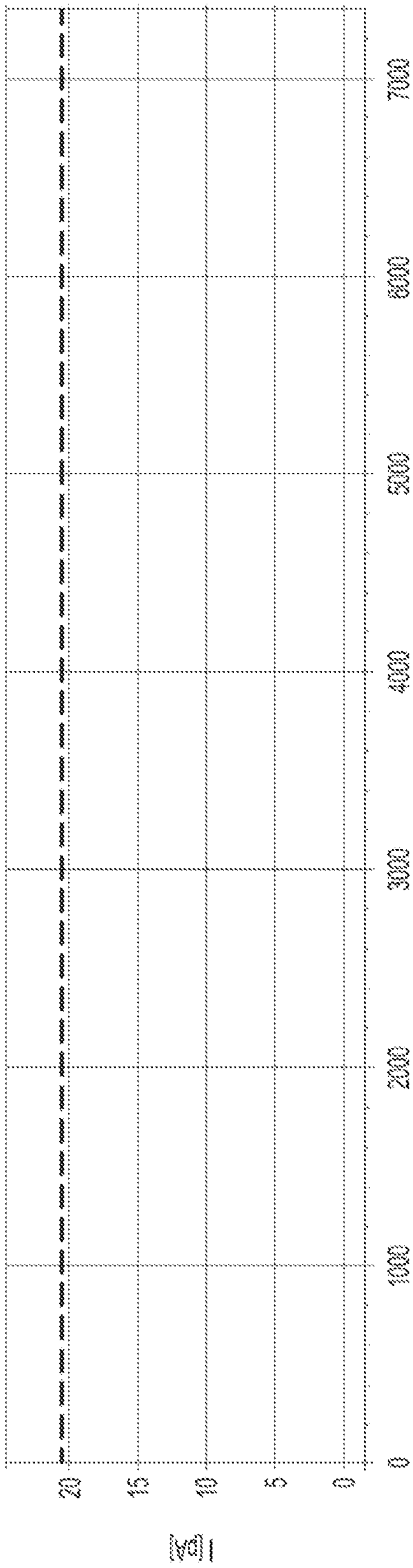
FIG. 23B is a graph depicting the current (pA, Y axis) versus time (s, X axis) for the first example MspA pores.

In the third experiment, the comparative MspA pores and the first example MspA pores were tested with 150 mM K+Cl− concentration and a cis-trans bias voltage of 50 mV. FIG. 23A plots the current (pA, Y axis) versus time (s, X axis) for the comparative MspA pores, and FIG. 23B plots the extrapolated current (pA, Y axis) versus time (s, X axis) for the first example MspA pores. The comparative pores exhibited significant current decay in the first 20 minutes, whereas the first example MspA pores exhibited no current decay.

ADDITIONAL COMMENTS

While various illustrative examples are described above, it will be apparent to one skilled in the art that various changes and modifications may be made therein without departing from the invention. The appended claims are intended to cover all such changes and modifications that fall within the true spirit and scope of the invention.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

What is claimed is:

1. A polypeptide nanopore comprising a first side, a second side, a channel extending through the first and second sides, and a mutated amino acid residue which is synthetically functionalized with a positively charged species that inhibits translocation of cations through the channel, wherein the positively charged species has a net charge of +2, wherein the mutated amino acid residue comprises a natural amino acid residue or an unnatural amino acid residue, and wherein the unnatural amino acid residue comprises an alkyne, azide, or alkene.

2. The polypeptide nanopore of claim 1, wherein the polypeptide nanopore comprises MspA, Fragaceatoxin C, α-hemolysin, aerolysin, CsgG, or CsgG/CsgF.

3. The polypeptide nanopore of claim 1, wherein the polypeptide nanopore comprises multiple polypeptide subunits.

4. The polypeptide nanopore of claim 1, comprising a plurality of the positively charged species.

5. A polypeptide nanopore comprising a first side, a second side, a channel extending through the first and second sides, and a mutated amino acid residue which is synthetically functionalized with a positively charged species that inhibits translocation of cations through the channel, wherein the polypeptide nanopore comprises MspA, and the mutated amino acid residue is located at residue 90, 91, or 93.

6. The polypeptide nanopore of claim 5, wherein the positively charged species comprises a nonmetal cation.

7. The polypeptide nanopore of claim 5, wherein the nonmetal cation comprises $NR_4$+, where each R group independently comprises hydrogen, a saturated alkyl group, an unsaturated alkyl group, an aromatic species, oxygen, nitrogen, silicon, sulfur, boron, phosphorous, a thiol, an ester derivation, an amide derivation, an amine derivation, a carbonyl derivation, a heterocycle, oligo (siloxane), oligo (ethylene oxide), an amino acid, a nucleobase, a reactive handle for further bioconjugation, a photoactive label, a photoactive dye, a redox-active label, or a redox-active dye, and at least one of the R groups is covalently linked to the mutated amino acid residue through at least one bond; or wherein the nonmetal cation comprises $C_5H_4R(NR)^+$, $C_3H_2R(NH)(NR)^+$, $C_8H_7R(NR_2)^+$, $C(NR_2)_3{}^+$, $SR_3{}^+$, $PR_4{}^+$, $BR_2{}^+$, $C_3R_3{}^+$ (cyclopropenium), $C_3R_3(NR)S^+$ (thiozonium), or $C_3R_3(NR)O^+$ (oxazonium), and where each R group independently comprises hydrogen, a saturated alkyl group, an unsaturated alkyl group, an aromatic species, oxygen, nitrogen, silicon, sulfur, boron, phosphorous, a thiol, an ester derivation, an amide derivation, an amine derivation, a carbonyl derivation, a heterocycle, oligo (siloxane), oligo (ethylene oxide), an amino acid, a nucleobase, a reactive handle for further bioconjugation, a photoactive label, a photoactive dye, a redox-active label, a redox-active dye, a nitrogenous aromatic and pi-conjugated species, apyridinium, an imidazolium, an indolium, a guanidinium, a carbazolium, a quinolinium, a functionalized derivative of a pyridinium, or a functionalized derivative of a purinium, and at least one of the R groups is covalently linked to the mutated amino acid residue through at least one bond.

8. A polypeptide nanopore comprising a first side, a second side, a channel extending through the first and second sides, and a mutated amino acid residue which is synthetically functionalized with a positively charged species that inhibits translocation of cations through the channel, wherein the positively charged species comprises a cationic metal coordination complex.

9. The polypeptide nanopore of claim 8, wherein the cationic metal coordination complex comprises at least one metal ion complexed to one or more nonmetal ligands.

10. The polypeptide nanopore of claim 9, wherein the at least one metal ion comprises a transition metal cation or a noble metal cation.

11. The polypeptide nanopore of claim 9, wherein the at least one of the one or more nonmetal ligands is covalently bound to the mutated amino acid residue.

12. A polypeptide nanopore comprising a first side, a second side, a channel extending through the first and second sides, and a mutated amino acid residue which is synthetically functionalized with a positively charged species that inhibits translocation of cations through the channel, wherein the positively charged species comprises an ionophore.

13. The polypeptide nanopore of claim 12, wherein the ionophore is covalently bound to the mutated amino acid residue.

14. A polypeptide nanopore comprising a first side, a second side, a channel extending through the first and second sides, and a mutated amino acid residue which is synthetically functionalized with a positively charged species that inhibits translocation of cations through the channel, wherein the polypeptide nanopore comprises multiple polypeptide subunits, and wherein at least one of the multiple polypeptide subunits does not comprise the mutated amino acid residue.

15. A polypeptide nanopore comprising a first side, a second side, a channel extending through the first and second sides, and a mutated amino acid residue which is synthetically functionalized with a positively charged species that inhibits translocation of cations through the channel, wherein the polypeptide nanopore comprises multiple polypeptide subunits, and wherein at least two of the polypeptide subunits are cross-linked to one another.

16. The polypeptide nanopore of claim 15, wherein the at least two of the polypeptide subunits are crosslinked through the positively charged species.

17. The polypeptide nanopore of claim 15, having an overall net charge of between about +2 and +18.

18. A polypeptide nanopore comprising a first side, a second side, a channel extending through the first and second sides, and a mutated amino acid residue which is synthetically functionalized with a positively charged species that inhibits translocation of cations through the channel, wherein the positively charged species has a net charge of +2, wherein the polypeptide nanopore comprises multiple polypeptide subunits, and wherein each of the polypeptide subunits is coupled to a respective positively charged species.

* * * * *